(12) United States Patent
Irazoqui et al.

(10) Patent No.: US 9,596,988 B2
(45) Date of Patent: Mar. 21, 2017

(54) PRESSURE SENSORS FOR SMALL-SCALE APPLICATIONS AND RELATED METHODS

(71) Applicants: Purdue Research Foundation, West Lafayette, IN (US); The Jackson Laboratory, Bar Harbor, ME (US)

(72) Inventors: Pedro P. Irazoqui, West Lafayette, IN (US); Dohyuk Ha, West Lafayette, IN (US); William J. Chappell, Vienna, VA (US); Simon W. M. John, Bar Harbor, ME (US)

(73) Assignees: Purdue Research Foundation, West Lafayette, IN (US); The Jackson Laboratory, Bar Harbor, ME (US)

(*) Notice: Subject to any disclaimer, the term of this patent is extended or adjusted under 35 U.S.C. 154(b) by 88 days.

(21) Appl. No.: 14/351,385

(22) PCT Filed: Oct. 12, 2012

(86) PCT No.: PCT/US2012/060070
§ 371 (c)(1),
(2) Date: Apr. 11, 2014

(87) PCT Pub. No.: WO2013/056130
PCT Pub. Date: Apr. 18, 2013

(65) Prior Publication Data
US 2014/0296687 A1  Oct. 2, 2014

Related U.S. Application Data

(60) Provisional application No. 61/546,324, filed on Oct. 12, 2011, provisional application No. 61/660,402, (Continued)

(51) Int. Cl.
*A61B 5/00* (2006.01)
*A61B 3/16* (2006.01)
(Continued)

(52) U.S. Cl.
CPC .............. *A61B 3/16* (2013.01); *A61B 5/686* (2013.01); *A61B 5/0215* (2013.01); *A61B 5/031* (2013.01);
(Continued)

(58) Field of Classification Search
CPC .... A61B 3/10; A61B 3/16; A61B 5/03; A61B 5/076; A61B 5/4839; A61B 5/686;
(Continued)

(56) References Cited

U.S. PATENT DOCUMENTS 6,423,001 B1 * 7/2002 Abreu ..................... 600/405
6,890,300 B2 * 5/2005 Lloyd et al. ............. 600/398
(Continued)

OTHER PUBLICATIONS

International Search Report and Written Opinion issued in PCT/US2012/060070.

*Primary Examiner* — Max Hindenburg
(74) *Attorney, Agent, or Firm* — Woodard, Emhardt, Moriarty, McNett & Henry LLP

(57) ABSTRACT

Certain pressure sensor devices are much smaller than prior art devices, yet are at least as sensitive as the prior art devices. A capacitive pressure sensor can include a flexible substrate that permits bending of a pressure sensing region without significantly affecting operation thereof. The pressure sensor can include a flexible membrane in which an electrode is sandwiched between two layers of polymeric material. The sandwiched electrode can be extremely close to a reference electrode so as to provide for highly sensitive capacitance readings, yet the membrane can be restricted from contacting the reference electrode under high pressure conditions.

17 Claims, 58 Drawing Sheets

Related U.S. Application Data filed on Jun. 15, 2012, provisional application No. 61/712,579, filed on Oct. 11, 2012.

(51) Int. Cl.
  *A61B 5/0215*  (2006.01)
  *A61B 5/03*  (2006.01)

(52) U.S. Cl.
  CPC . *A61B 2562/028* (2013.01); *A61B 2562/0247* (2013.01); *A61B 2562/12* (2013.01)

(58) Field of Classification Search
  CPC .................. A61B 5/0215; A61B 5/031; A61B 2562/0247; A61B 2562/028; A61B 2562/12; A61M 5/16804
  See application file for complete search history.

(56) References Cited

U.S. PATENT DOCUMENTS

| | | |
|---|---|---|
| 7,131,945 B2 * | 11/2006 | Fink et al. .................... 600/398 |
| 7,137,952 B2 * | 11/2006 | Leonardi et al. ............. 600/398 |
| 2008/0061799 A1 | 3/2008 | Kim et al. |
| 2008/0066557 A1 | 3/2008 | Yoshida |
| 2009/0299216 A1 | 12/2009 | Chen et al. |
| 2011/0084570 A1 | 4/2011 | Soeda et al. |

* cited by examiner

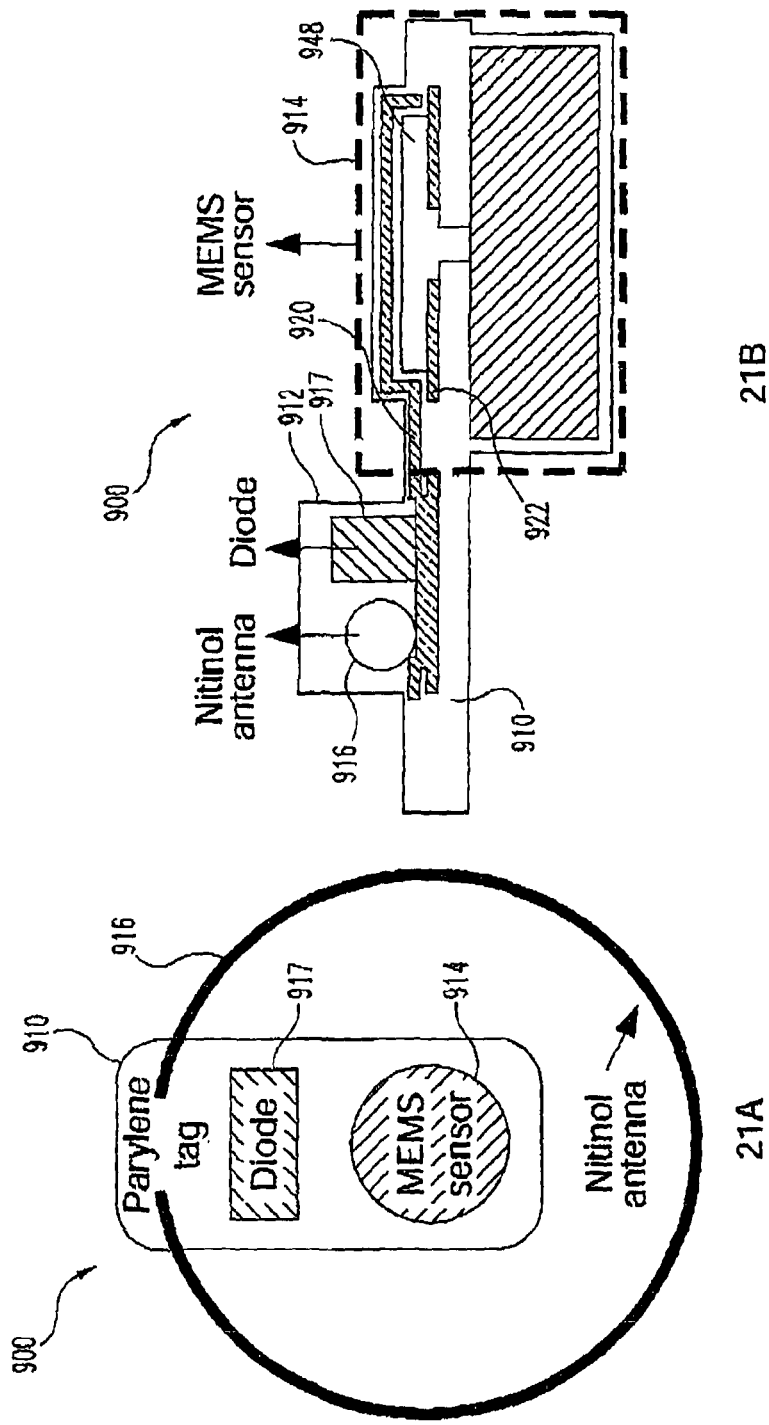
FIG. 21. Third-order harmonic passive tag for IOP monitoring (top view (left) and cross-sectional view (right)).

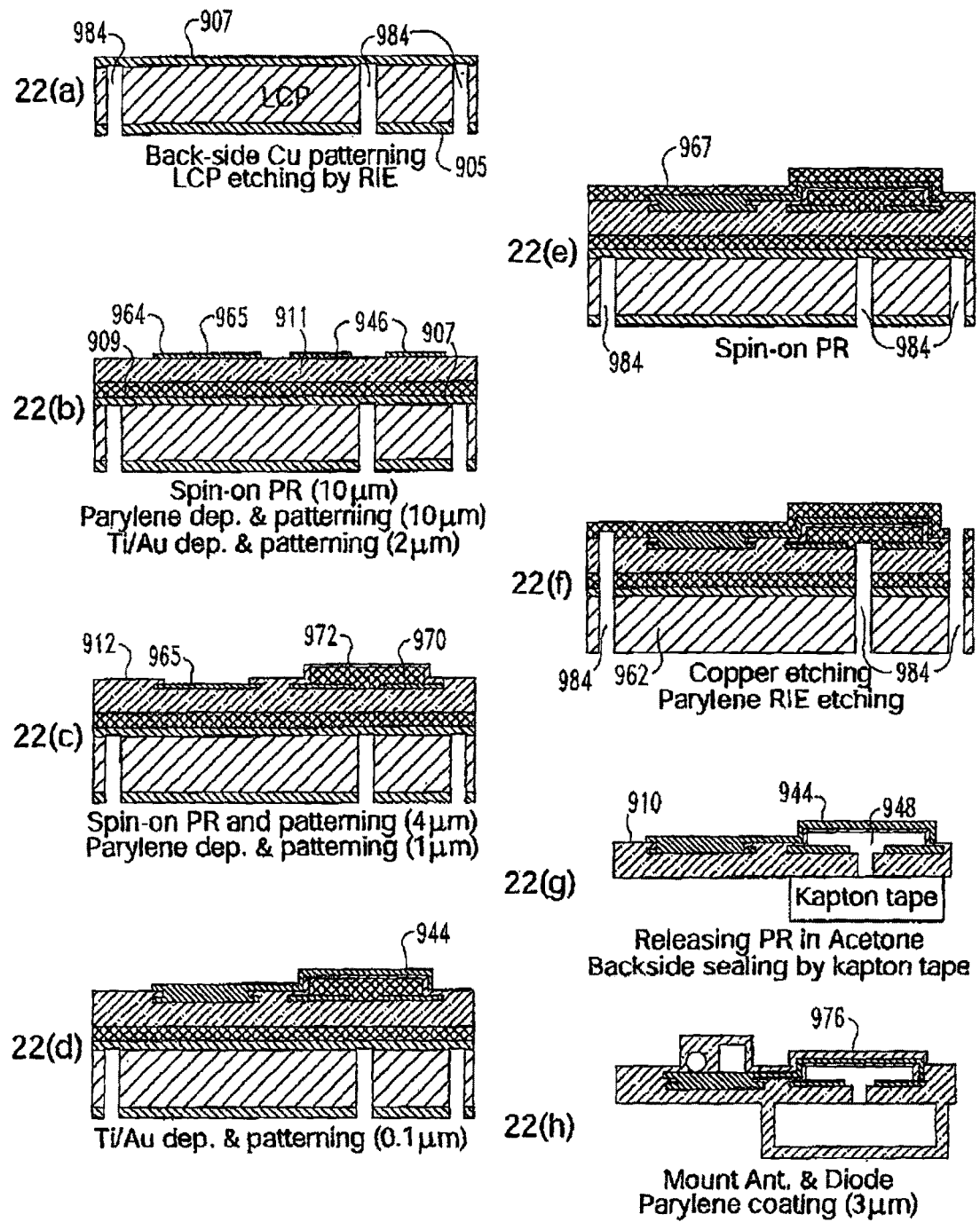
FIG. 22. Fabrication process flow of the compact-size tag for monitoring IOP inside the mouse eye.

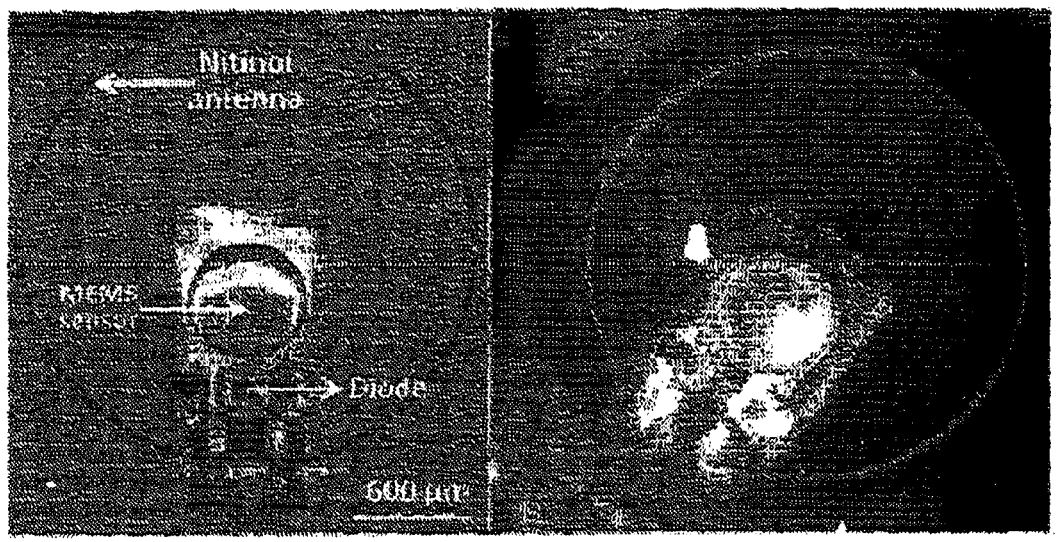
FIG. 23. The fully packaged Parylene tag (left) and its implantation inside the mouse eye (right)
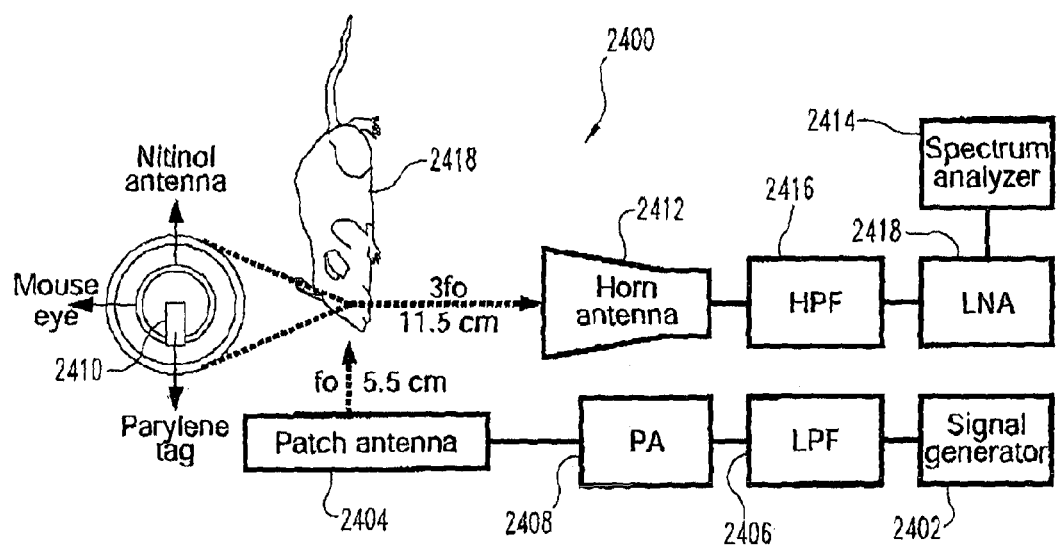
FIG. 24. Experimental set up for in-vivo testing (The image of the mouse)

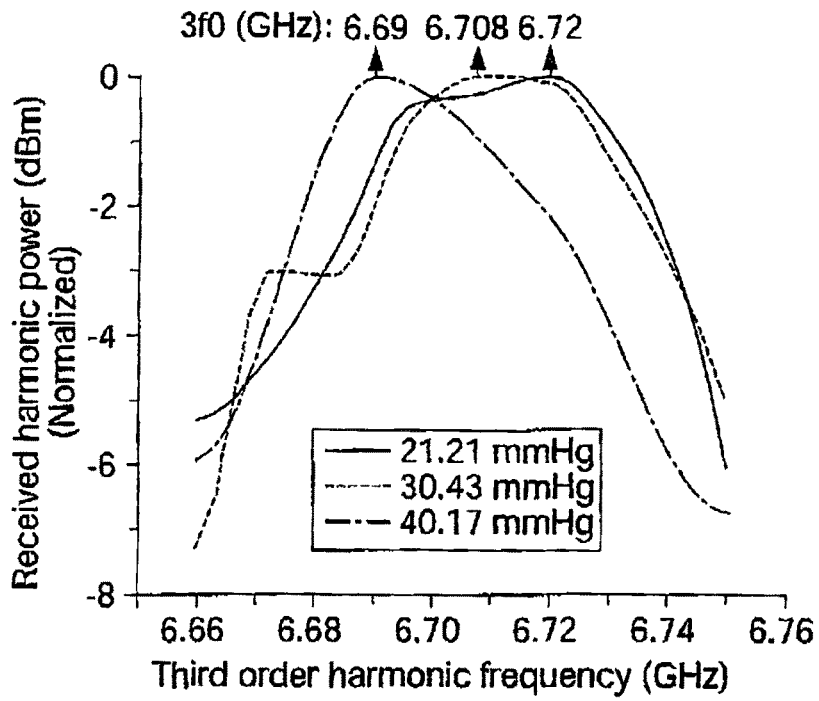
FIG. 25. Measured resonance frequency shift for the change of IOP. (Normalized and fitted from the originally corrected data)
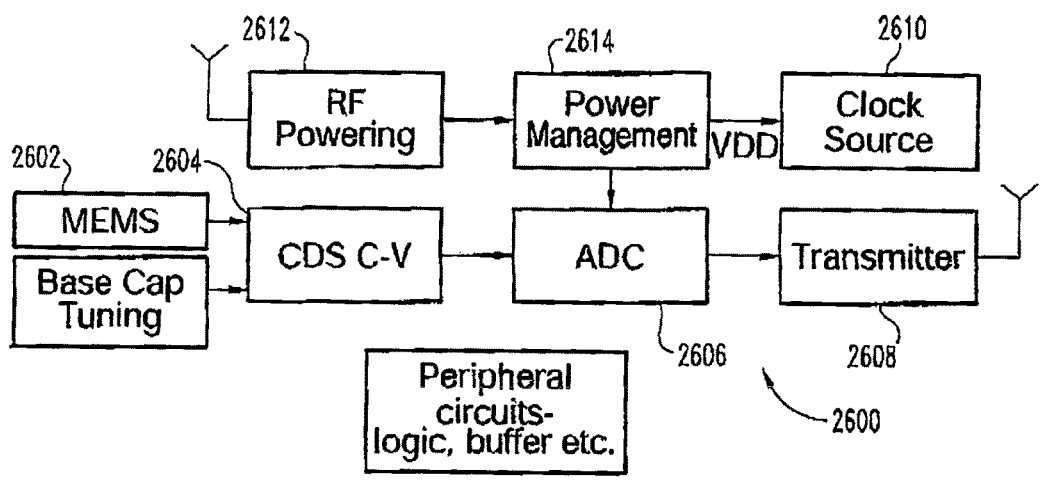
FIG. 26. Block diagram of fully wireless implantable micro-system

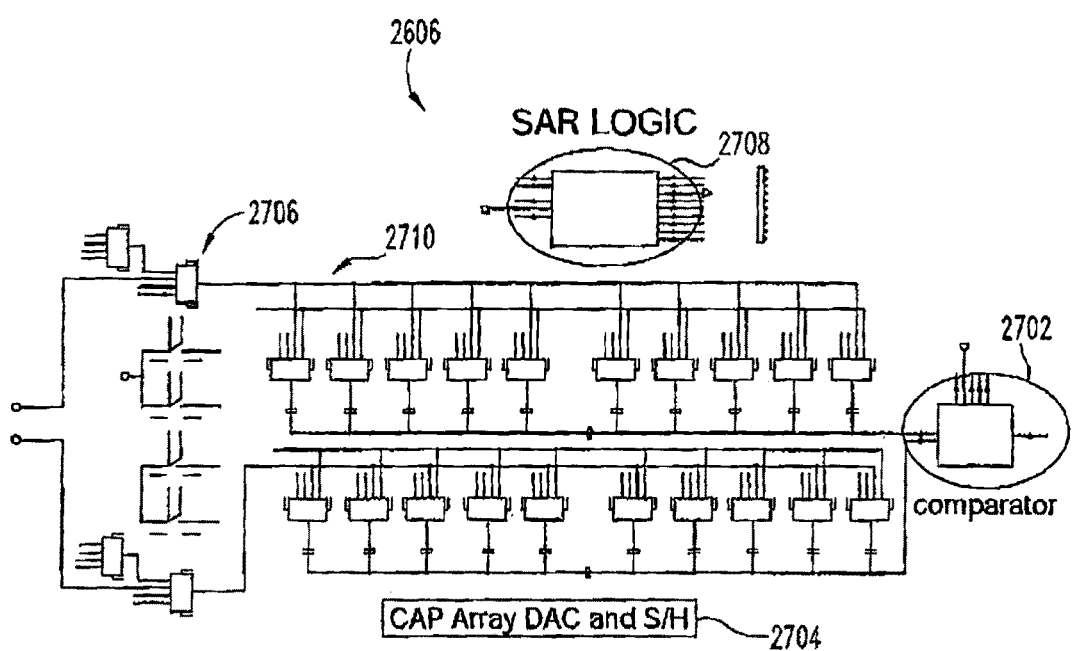
FIG. 27. Top level schematic of SAR ADC

Top Level Schematic of Comparator

Preamplifier schematic design

Auto Zeroing clock generation circuit

Schematic of Latch

Top level Schematci of 10 bit SAR Logic

FIG. 33. Top level simulation result for 10 bit SAR ADC (input=400mV peak sinusoidal of 500 Hz)

FIG. 34. SAR ADC top level layout (320 μm X 240 μm

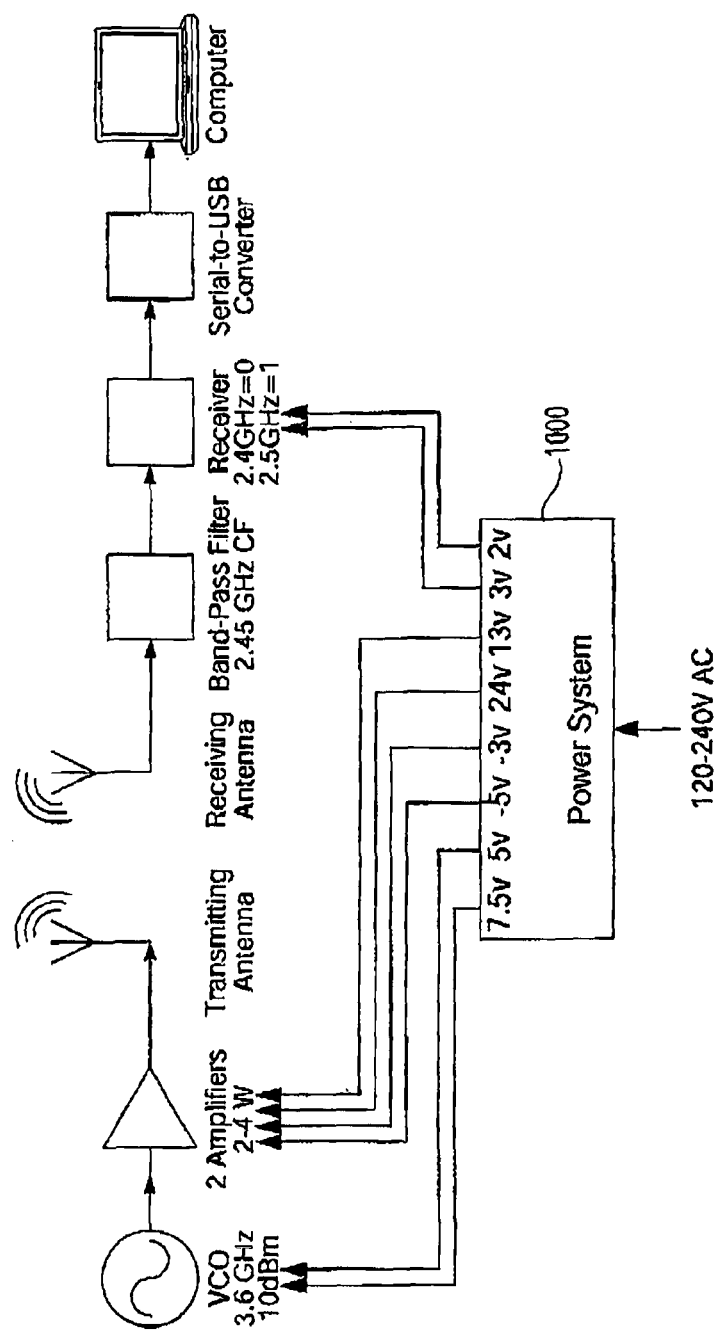
FIG. 37 Basestation functional block diagram

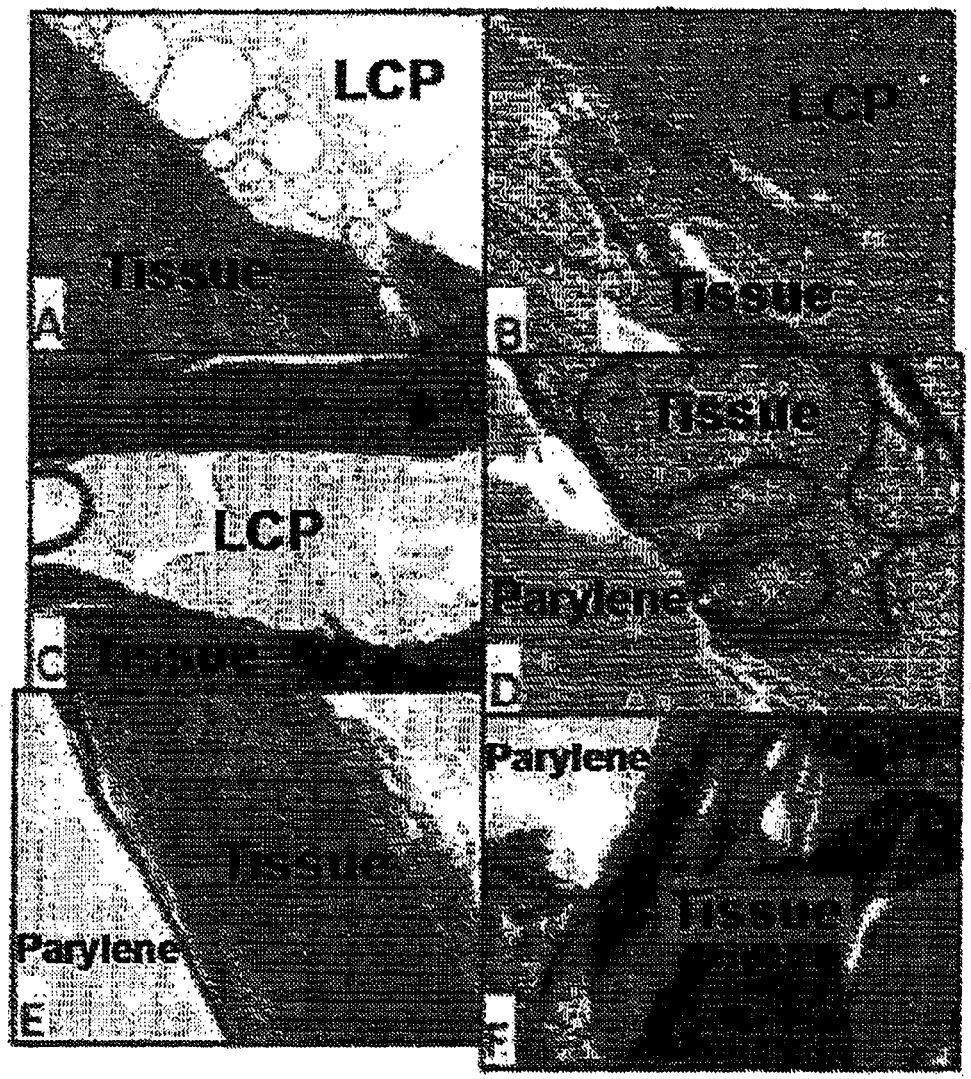
FIG. 38 Stained micrographs under 50x magnification used in histological studies of LCP (a) after 7 days, (b) after 14 days, and (c) after 28 days; and parylene coated LTCC (d) after 7 days, (e) after 14 days, and (f) after 28 days.

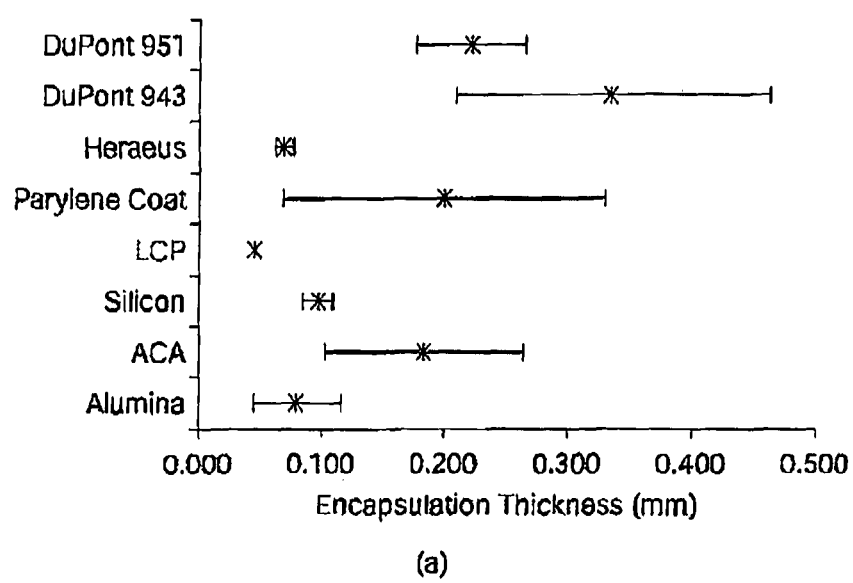
(a)
FIG. 39. Measurements of fibrous encapsulation after (a) 7 days. Data represented as mean +/- standard deviation

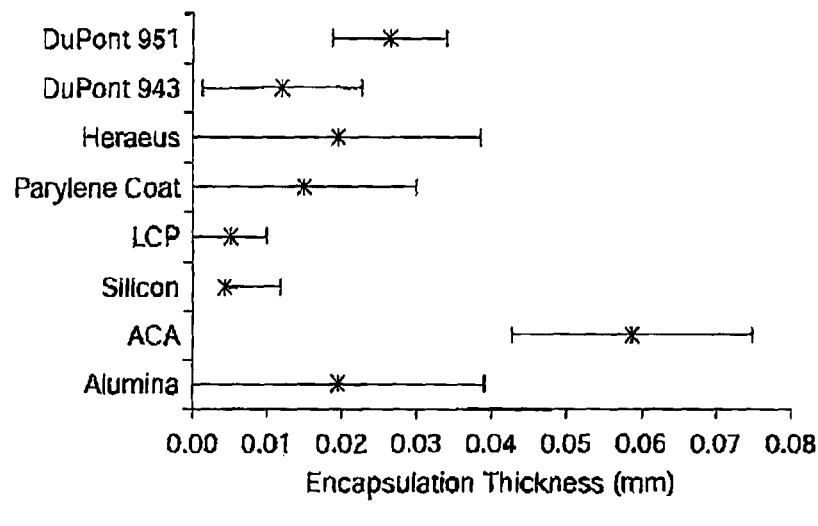
FIG. 40. Measurements of fibrous encapsulation after (b) 14 days. Data represented as mean +/- standard deviation
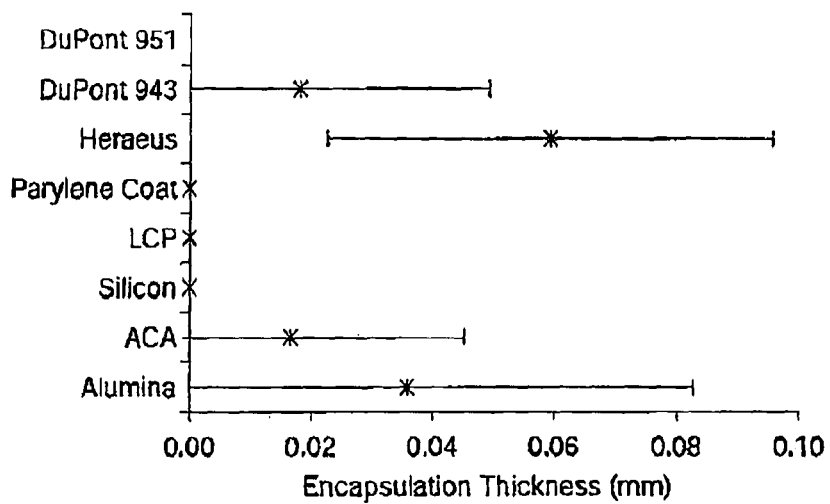
FIG. 41. Measurements of fibrous encapsulation after (c) 28 days. Data represented as mean +/- standard deviation

FIG. 42 First surgical implantation of tadpole IOP device
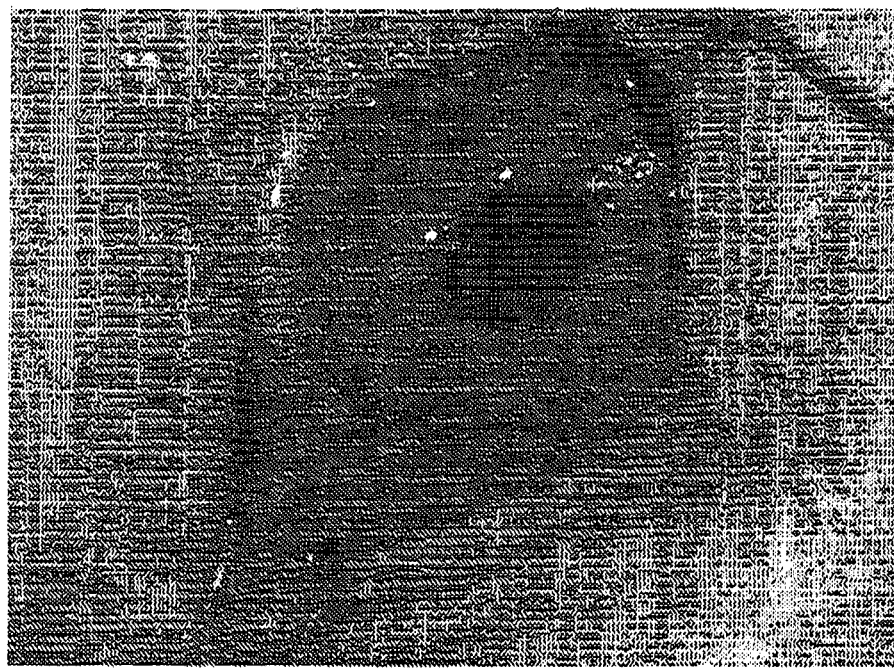
FIG. 43 First implantation of CTR IOP device

FIG. 44 Dummy device implantation
FIG. 45 LED Device active in mouse surgery

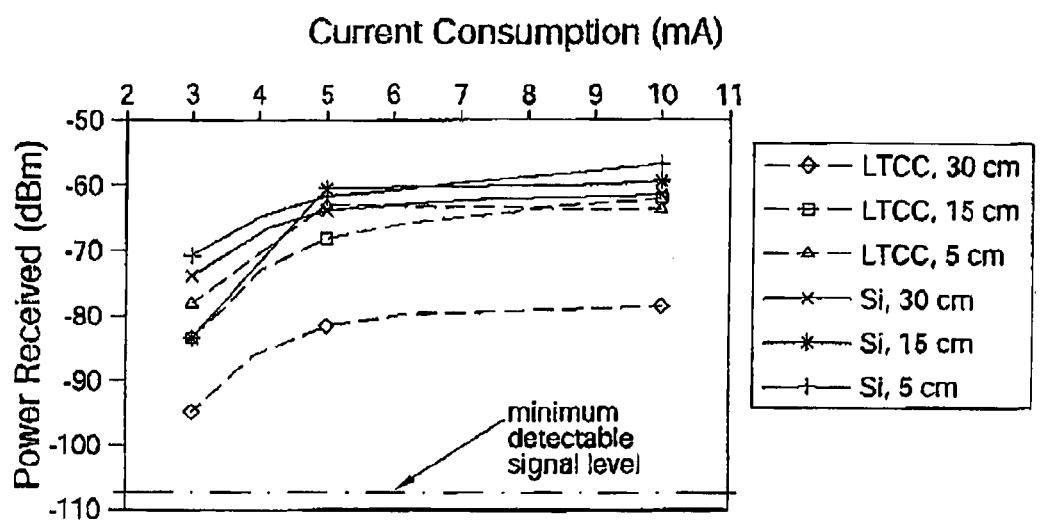
FIG. 46. LTCC and Silicon power received using RF powering.

Mouse sized IOP device with surface mount passive components

FIG. 48. Block diagram of full system device

FIG. 49. Reflection coefficient characterization of components obtaining and harvesting RF energy (a) Real Parameter (b) Imaginary parameter Radio frequency powering setup to test devices in-vivo and ex-vivo Tadpole based off human IOP design Large LED ring device of FR-4

Small LED ring device of FR-4

Further optimization onto LCP of LED device

LED device wirelessly powered

Device size comparison to O of one of a penny

IOP device above antenna

Dummy sample being compressed for implantation

Mouse animal model implanted with LED device

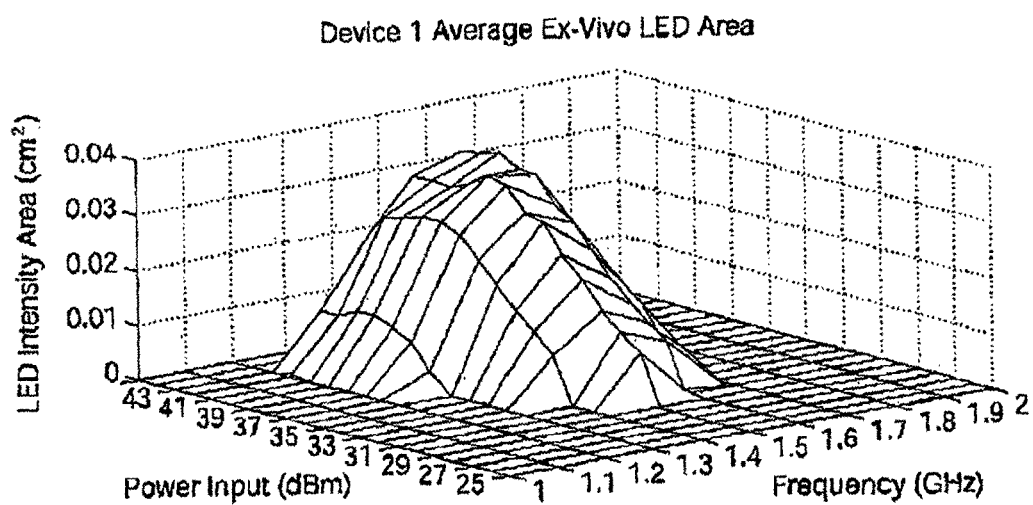
FIG. 60. Device 1 (a) LED area
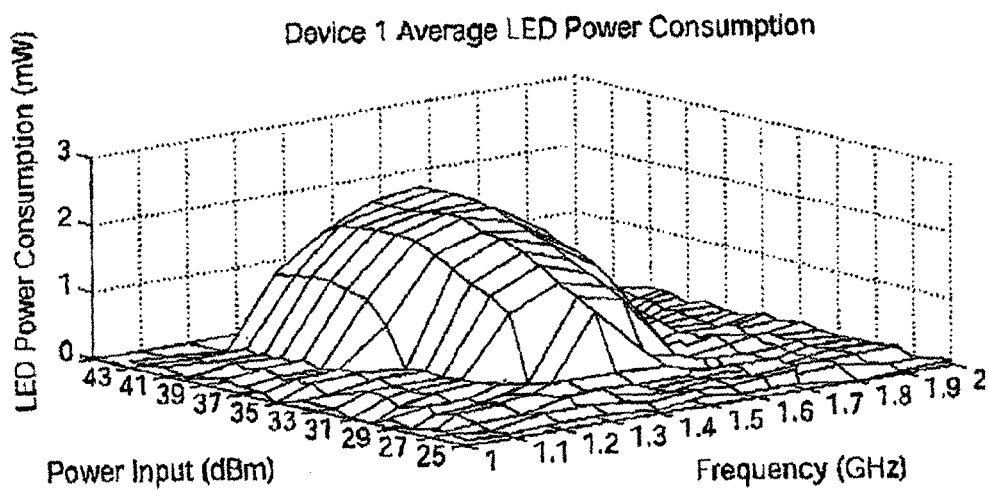
FIG. 61. Device 1 (b) LED power consumption using wireless RF powering

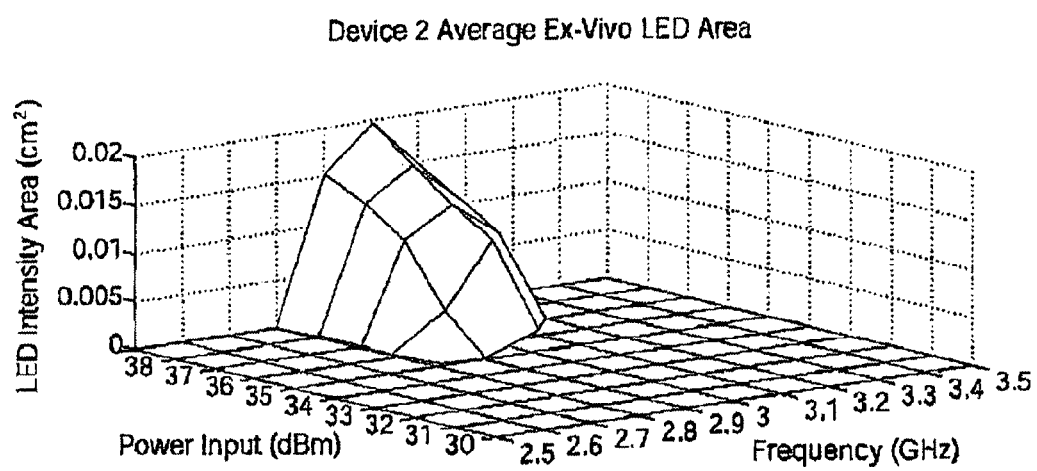
FIG. 62. Device 2 (a) LED area
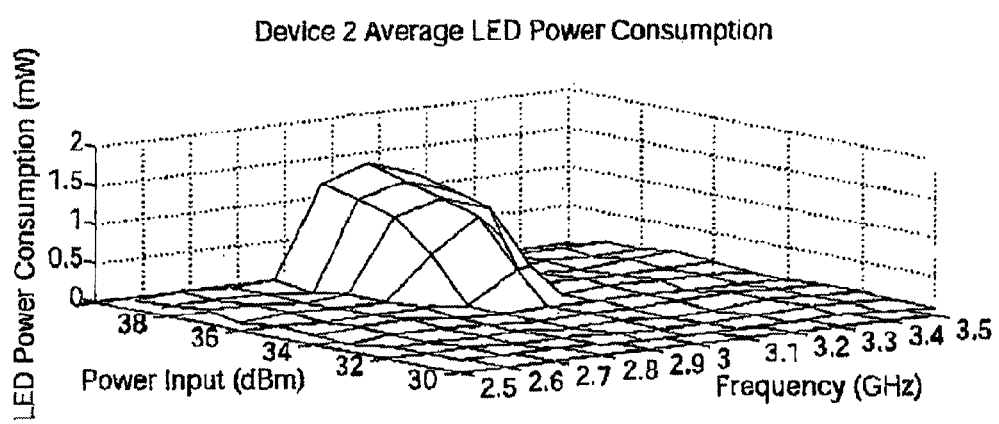
FIG. 63. Device 2 (b) LED power consumption using wireless RF powering

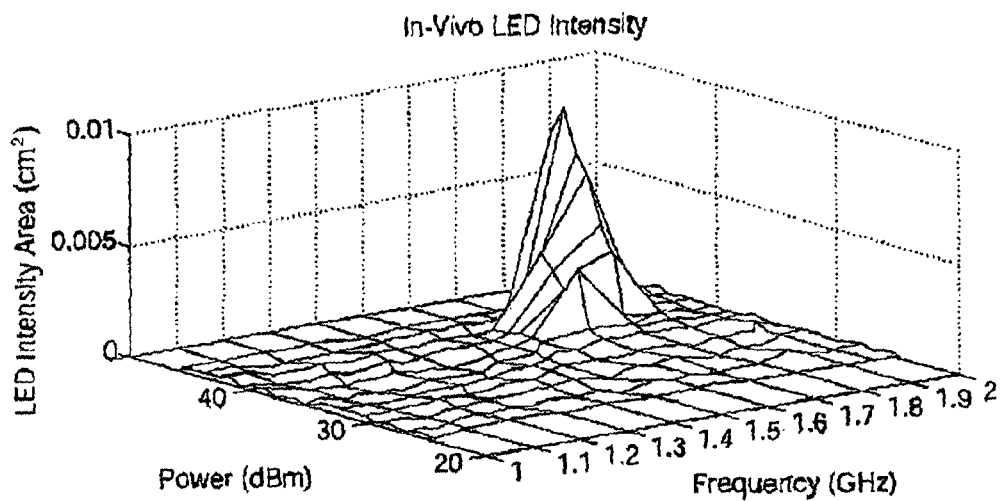
FIG. 64. Device 1 (a) LED area
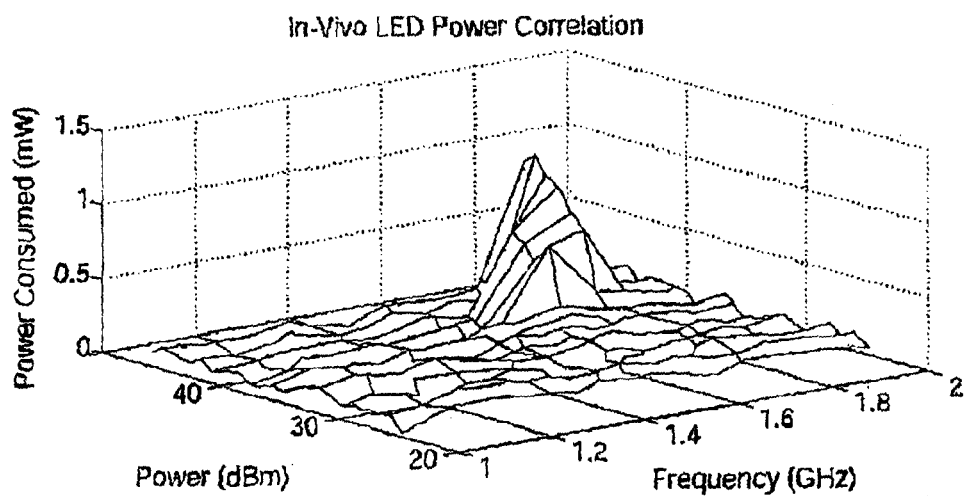
FIG. 65. Device 1 (b) LED power consumption of LED device implanted in anterior chamber of mouse eye for 1 month Vascularization of eye following implantation of LED device. Blue indicates vascularization. Purple is reflectance.

Histological response 2 weeks post-mortem.
Blue is the vascularization. Purple is reflectance.

3D recreation of 2 week implantation. Color incorporates depth. Red constitutes tope white blue is farther away from lens.

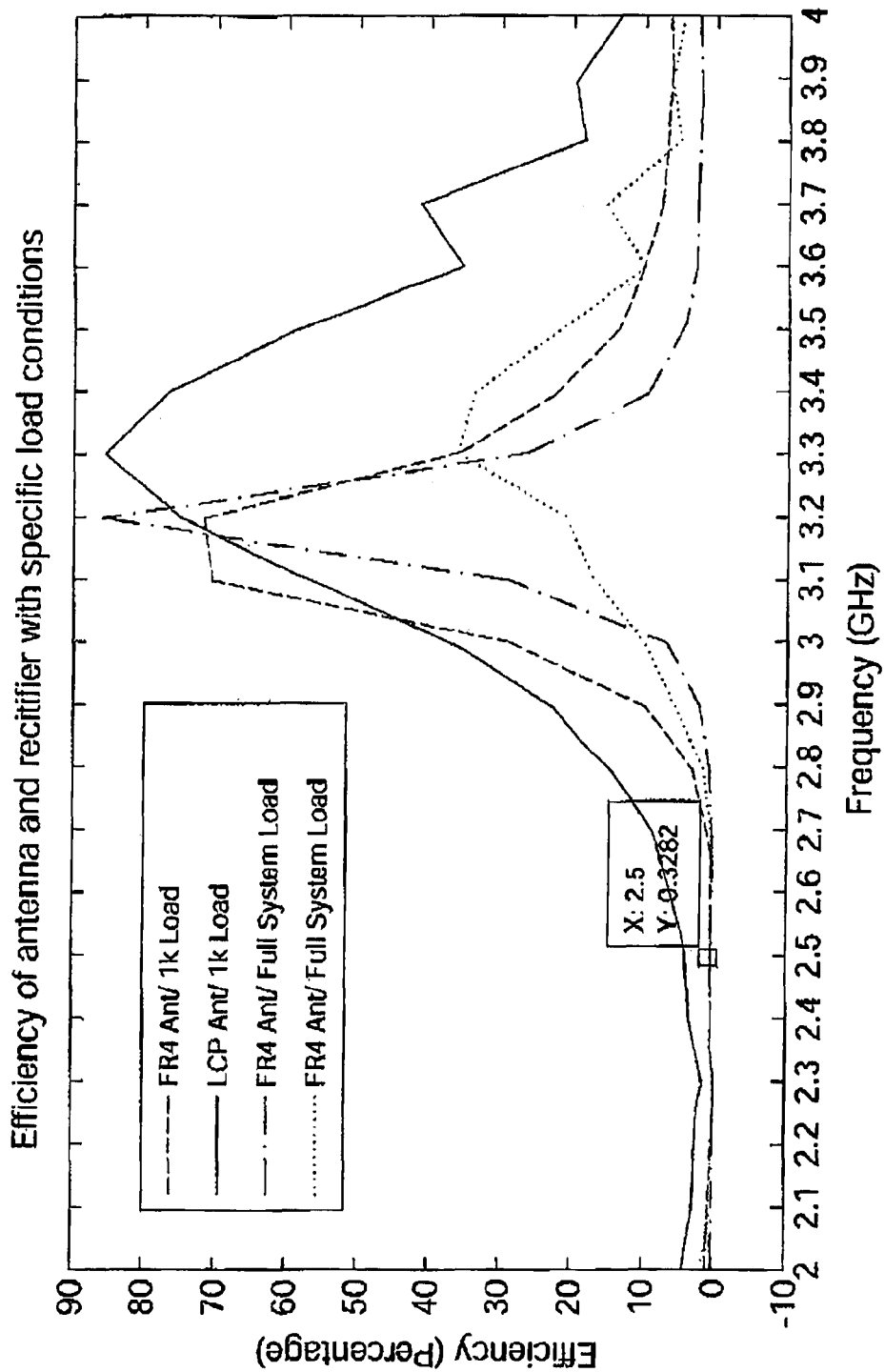
FIG. 69. Analysis of efficiency of specific antenna types connected to ASIC rectifier circuit under different load conditions

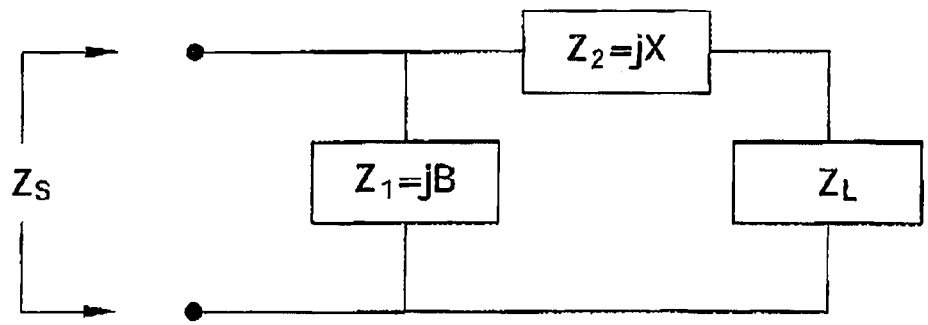
FIG. 70. Condition for matching two complex impedances that lie outside 1+jω circle. $Z_L$ and $Z_S$ are load impedance and source impedance respectively. $Z_1$ and $Z_2$ are inductors or capacitors for matching purposes.

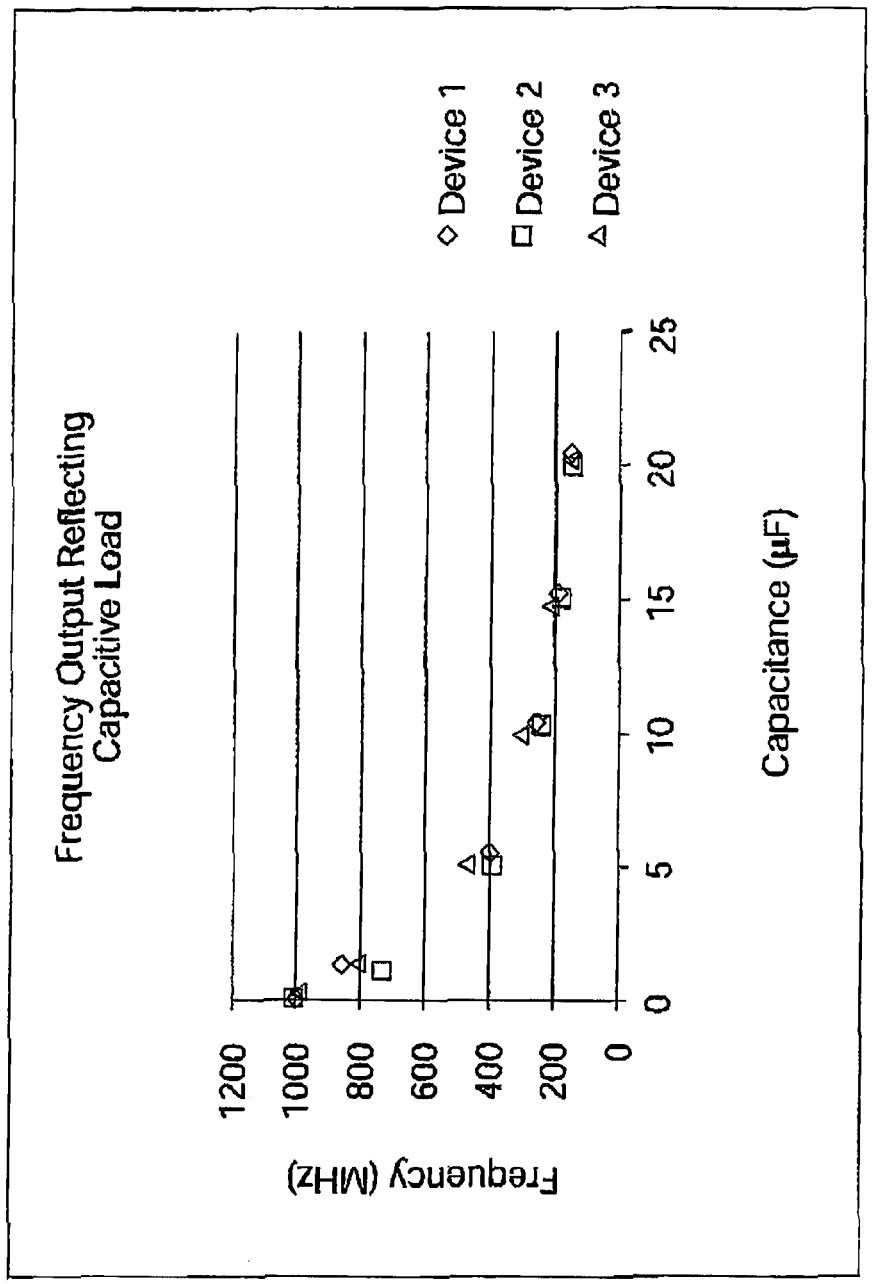
FIG. 71 Measurement circuit output. Relationship of capacitive load on frequency output

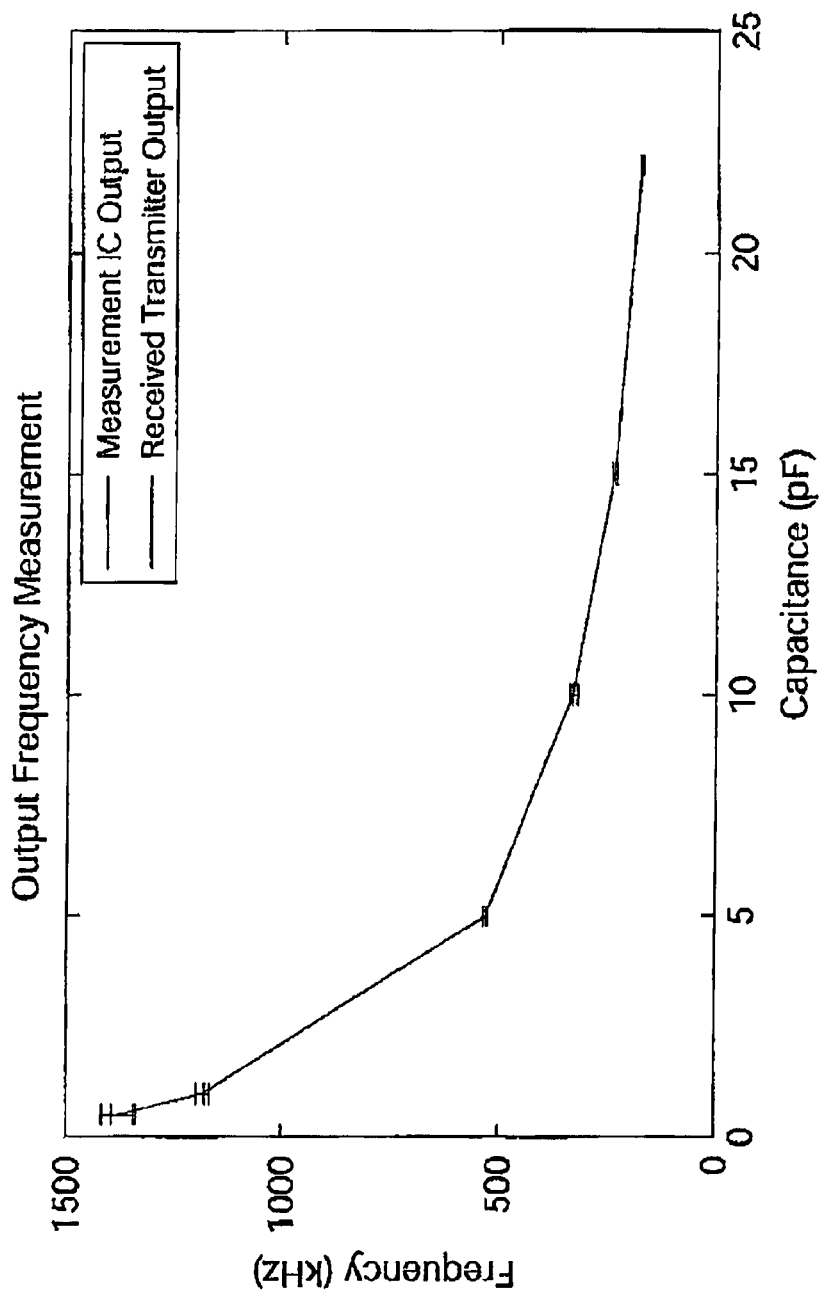
FIG. 72 Comparison Measurement output and transmission demodulation for a given output capacitance

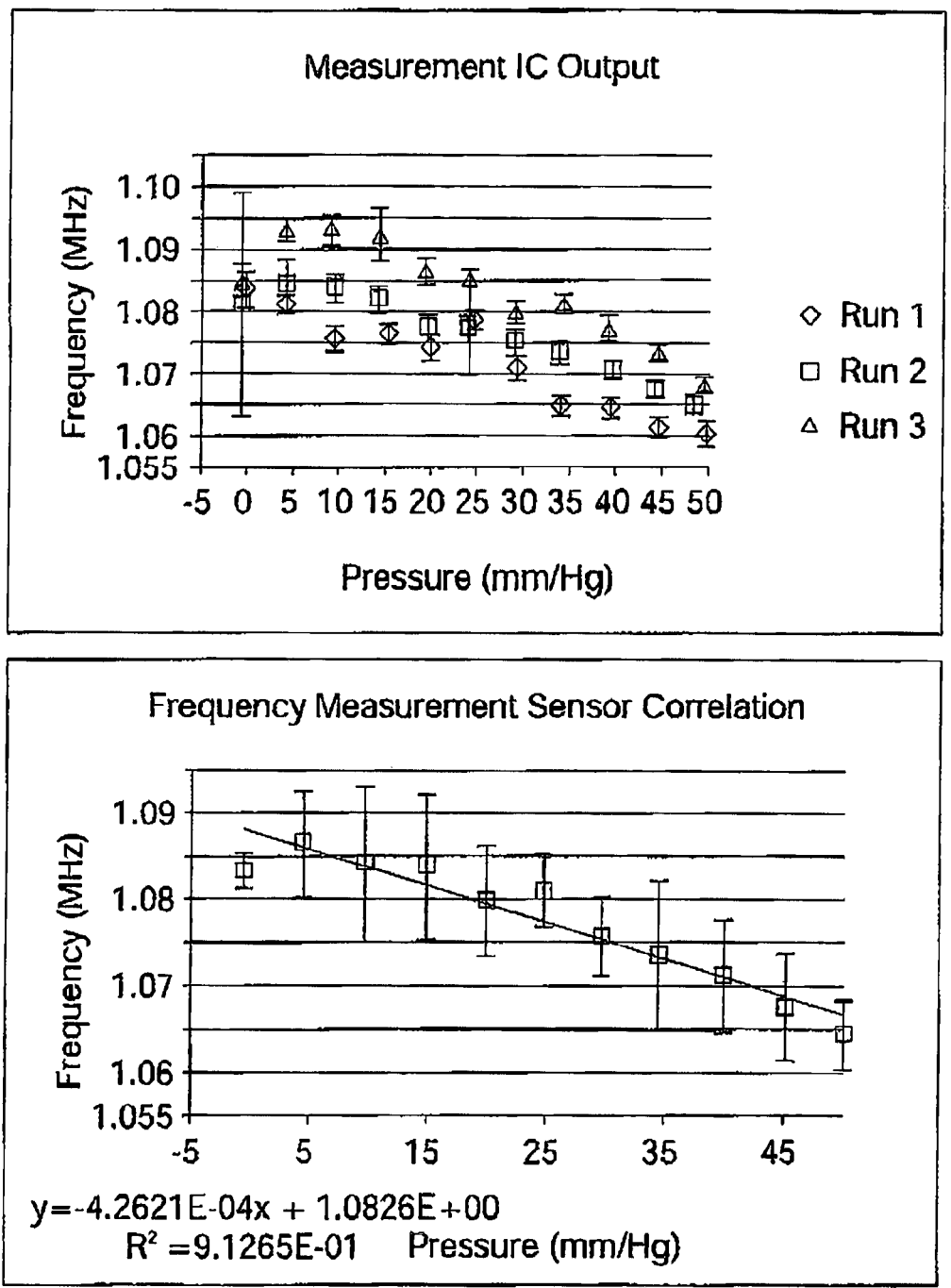
FIG. 73 Output data of measurement system using MEMS sensor in pressure chamber

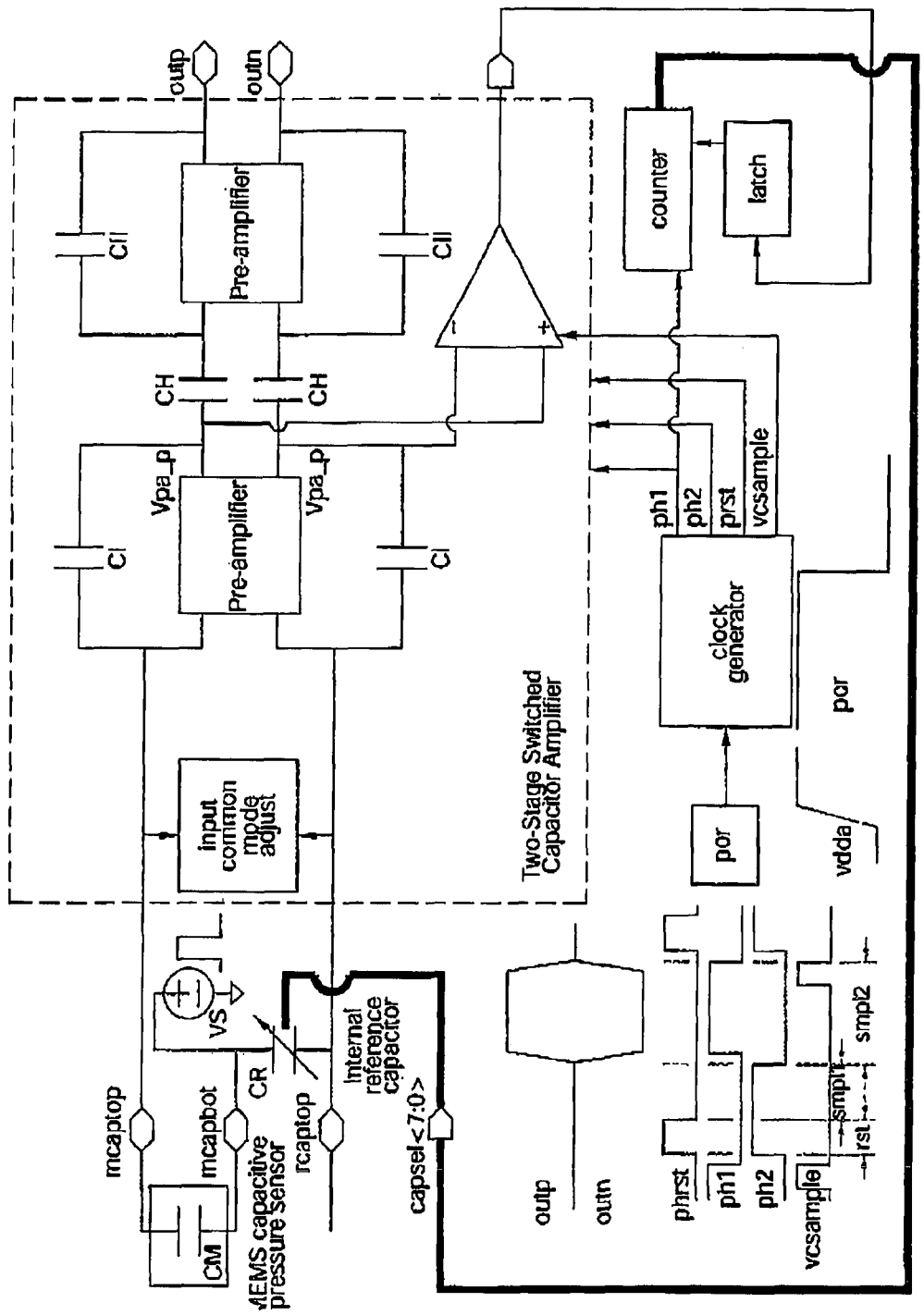
FIG. 74-CDS-CV block diagram

PRESSURE SENSORS FOR SMALL-SCALE APPLICATIONS AND RELATED METHODS

CROSS REFERENCE TO RELATED APPLICATIONS

This application claims the benefit of U.S. Provisional Patent Application Nos. 61/546,324 filed Oct. 12, 2011, 61/660,402 filed Jun. 15, 2012, and 61/712,579 filed Oct. 11, 2012 all of which are hereby incorporated by reference in their entirety.

TECHNICAL FIELD

The present disclosure relates to pressure sensors. More specifically, the present disclosure relates to miniaturized wireless pressure monitoring devices, and related components and methods.

BACKGROUND

Biomedical engineering with real-time biological information, such as eye pressure, blood pressure, core body temperature and neural signals, has become useful in the research for identifying genetic variation susceptibility to diseases. Animal-based research result is expected to make a helpful impact in developing new treatment methods for similar human diseases. A miniature and implantable bio-sensing microsystem with wireless telemetry and RF powering is highly desirable to capture accurate bio-signals and information. These CMOS-based devices have additional aspects for managing a large number of channels: signal multiplexing, amplification, A/D conversion and filtering are done on-chip. Developing the micro-system includes sensing methods study for various vital signals. Among the biological signals, eye pressure for Glaucoma patients is one of the more useful vital signals.

Glaucoma, the second leading cause of blindness, is a debilitating disease that affects millions of people. Current data suggests that 60 million people have glaucoma, and that number is to reach 79 million by the year 2020. Several risk factors put you at a disadvantage to contract the disease, including ethnicity, age, and family history. In glaucoma, death of optic nerve cells leads to blindness. Currently, doctors have very few options in detecting glaucoma, and many of them only detect glaucoma after enough damage has occurred and it is too late to prevent the disease. These include visual field testing, Ocular Coherence Tomography, and Intra Ocular Pressure (IOP) monitoring.

The first two determine glaucoma after the damage has been completed, and can be used as an aid to monitor damage that has already been completed. IOP monitoring is the only method in which doctors can prevent the glaucoma from beginning and is the strongest known contributing factor to optic nerve cell death. Although it is clear that high IOP is harmful to the optic nerve, the exact relationships between the kinetics, duration, and magnitude of IOP elevation and optic nerve damage are not known.

Doctors use several methods to examine IOP's glaucomatous effects. First, Goldmann tonometry (the gold standard) is a noninvasive method to measure the pressure inside the eye. Goldmann tonometry uses the Imbert-Fick law that equates pressure based on flattening of the cornea. This leads to misdiagnosis from individual to individual based on physiological characteristics. Studies conducted by Whitacre et al. found several errors occurring from using these indentation, or mathematical computations, to determine IOP. The only viable invasive measurement technique currently available is microneedle cannulation. This process involves inserting a needle, connected to a pressure gauge, into the anterior chamber of the eye and monitoring. This is a very invasive method of monitoring eye pressure, and if a physician needs continuous data, it is infeasible. As IOP changes considerably even within a single day, typical annual or semi-annual measurements at a doctor's visit can be misleading or uninformative.

The mouse is a well-suited mammalian model for deciphering the mechanisms of this complex disease due to the similarity of its well-known genome to the human. N-ethyl-N-nitrosourea (ENU) mutagenesis followed by phenotypic screening is proving to be a fruitful approach to studying glaucoma. In this approach, there is considerable variability in age of onset of IOP elevation, even in mice with the same mutation. Thus, success is limited where IOP measurement data over many months cannot be continuously and remotely assessed. In order to study the mechanism of the disease, continuous monitoring of intraocular pressure (IOP) using an implanted sensor is useful. The diameter of the anterior chamber in a mouse eye is approximately 3 mm and its depth is 75 microns at the edge and 300 microns in the center. However, current IOP sensors are not suitable to be used as a mouse eye implant due to their size. Furthermore, sensors that use near field inductive coupling do not provide the sensitivity and the sensing distance needed for IOP monitoring with a resolution of 1 mmHg from mice which are awake and roaming within a cage. Therefore, a fundamental challenge lies in the creation of a suitably sensitive sensor that will fit in the small space available in the eye of the mouse and provides the needed continuous monitoring and sensing properties for use with mice in typical laboratory cages.

In addition, implantable pressure sensors are useful with regards to other conditions. As one example, the breast implant market is 1-2 billion dollars a year. Half of those sales are for silicone gel implants. The primary concern is that when they rupture, there is no way to detect the rupture without an MRI scan. The FDA recommends all women receive an MRI every 2-3 years at a cost of $1,500-$2,000 each.

As implantable devices become "smart", using Application Specific Integrated Circuits (ASICs) and other electrical components to sense their surroundings, power consumption becomes an aspect of running these devices efficiently. Currently, there are several methods in which a power source is supplied to implantable devices. One includes the use of high mAh batteries that allow the device to be powered for many years. Second, such as with implantable hearing aids, inductive coupling is used with an external power source coupling energy to the implanted device to stimulate the hair follicles inside the cochlea.

These two powering techniques, although acceptable, have drawbacks. Using a battery is efficient and allows for a long implant life, but once that battery has died a second usually major surgery is required to outfit a patient with a new battery. In the case of a cardiac pacemaker, this is costly and life threatening. Using inductive coupling, a staple in cochlear implants, is efficient in close range to power the device. However, there lies its drawback, that the external device should always be closely located and arranged for proper alignment and powering.

Improvements and alternatives are therefore needed in this field.

SUMMARY

According to one aspect, the present disclosure relates to a capacitive pressure sensor for monitoring fluid pressure within a patient is disclosed, the pressure sensor comprising: a flexible substrate configured to bend so as to conform to a curved surface; a first electrode in abutting contact with the substrate, wherein the first electrode is configured to bend in conformity with the substrate; a membrane spaced from the first electrode, wherein the membrane comprises: a second electrode configured to be displaced toward the first electrode; and at least one flexible layer covering at least a portion of the second electrode; and a dielectric region between the first electrode and the membrane, wherein the pressure sensor has a sensitivity of no less than about 0.3 fF/mmHg whether the substrate is in a flat orientation or a curved orientation.

According to another aspect, the present disclosure relates to a capacitive pressure sensor for monitoring fluid pressure within a patient, the pressure sensor comprising: a substrate; a first electrode in abutting contact with the substrate; a membrane spaced from the first electrode, wherein the membrane comprises: a second electrode configured to bend toward the first electrode; and at least one flexible layer covering at least a portion of the second electrode; and a dielectric region between the first electrode and the membrane having a depth of no greater than about 7 microns when the membrane is in an uncompressed position; wherein the pressure sensor has a sensitivity of no less than about 0.3 fF/mmHg. According to other aspects, the second electrode may be thinner than the at least one flexible layer so as to readily bend when the at least one flexible layer is bent toward the substrate. According to other aspects, the second electrode may be sandwiched between two flexible layers. According to other aspects, the substrate and the at least one flexible layer may be polymeric. According to other aspects, the substrate may comprise liquid crystal polymer and the at least one flexible layer may comprise parylene. According to other aspects, the sensitivity may be substantially constant over a range of from about 0 mmHg to about 50 mmHg above atmospheric pressure. According to other aspects, the perimeter of the substrate may define an area of no greater than about 2 millimeters$^2$. According to other aspects, a pressure sensing area of the sensor may be no greater than about 0.5 millimeters$^2$. According to other aspects, the an additional flexible layer may cover at least a portion of the first electrode, wherein the additional flexible layer and the at least one flexible layer of the membrane comprise the same material. According to other aspects, the dielectric region may comprise a gas. According to other aspects, the dielectric region may comprise air.

According to another aspect, the present disclosure relates to a system for monitoring fluid pressure within a patient, the system comprising: a flexible substrate configured to bend so as to conform to a curved surface, wherein the flexible substrate defines a maximum width of no greater than about 0.7 millimeters; a capacitive pressure sensor coupled with the substrate, wherein a maximum width of the pressure sensor is no greater than the maximum width of the substrate, the pressure sensor comprising: a first electrode in abutting contact with the substrate, wherein the first electrode is configured to bend in conformity with the substrate; a membrane spaced from the first electrode, wherein the membrane comprises: a second electrode configured to be displaced toward the first electrode; and at least one flexible layer covering at least a portion of the second electrode; and a dielectric region between the first electrode and the membrane; and an integrated circuit coupled with the substrate and electrically coupled with the pressure sensor, wherein a maximum width of the integrated circuit is no greater than the maximum width of the substrate.

According to another aspect, the present disclosure relates to a method of monitoring intraocular pressure in a mouse, the method comprising: implanting a pressure-sensing system within the anterior chamber of an eye of a mouse, wherein the pressure-sensing system comprises a flexible substrate having an area of no greater than about 2 millimeters$^2$; and receiving data from the pressure-sensing system via equipment that is external to the mouse. According to other aspects the pressure-sensing system comprises a pressure-sensing area of no greater than about 0.5 millimeters$^2$. According other aspects the pressure-sensing system comprises a capacitive pressure sensor that is integrated with the flexible substrate and comprises a flexible membrane, wherein the flexible substrate comprises liquid crystal polymer and the flexible membrane comprises parylene.

According to another aspect, the present disclosure relates to a system for monitoring fluid pressure within an eye, the system comprising: a substrate defining a maximum width of no greater than about 0.7 millimeters; a pressure sensor coupled with the substrate, wherein a maximum width of the pressure sensor is no greater than the maximum width of the substrate; an integrated circuit coupled with the substrate and electrically coupled with the pressure sensor, wherein a maximum width of the integrated circuit is no greater than the maximum width of the substrate; an antenna coupled with the substrate and electrically coupled with the integrated circuit, the antenna and integrated circuit adapted to receive a first wireless signal for powering the system and transmit a second wireless signal, the second wireless signal providing an indication of the fluid pressure; an LED coupled with the substrate and electrically coupled with the integrated circuit, wherein a maximum width of the LED is not greater than the maximum width of the substrate, wherein the light intensity of the LED output provides an indication of power being received by the system from a wireless external power source. In certain embodiments, the antenna transmits the second signal at a harmonic of the frequency of the first signal, such as the third harmonic.

According to another aspect, the present disclosure relates to a system for monitoring fluid pressure within an eye, the system comprising: a substrate defining a maximum width of no greater than about 0.7 millimeters; a pressure sensor coupled with the substrate, wherein a maximum width of the pressure sensor is no greater than the maximum width of the substrate; an integrated circuit coupled with the substrate and electrically coupled with the pressure sensor, wherein a maximum width of the integrated circuit is no greater than the maximum width of the substrate; an antenna coupled with the substrate and electrically coupled with the integrated circuit, the antenna and integrated circuit adapted to receive a first wireless signal for powering the system and transmit a second wireless signal, the second wireless signal providing an indication of the fluid pressure, wherein the second wireless signal is transmitted at a harmonic of the first wireless signal, such as the third harmonic.

According to another aspect, the present disclosure relates to a method of forming a capacitive pressure sensor, the method comprising: providing a flexible polymeric substrate; depositing a first layer of metal on the polymeric substrate so as to form a first electrode; and forming a flexible membrane over the first layer of metal, wherein said forming comprises: positioning a first polymeric layer above at least a portion of the first layer of metal; depositing a second layer of metal over the first polymeric layer; and depositing a second polymeric layer over at least a portion of the second layer of metal. The method may further comprise depositing a layer of sacrificial photoresist over at least a portion of the first layer of metal, wherein said positioning a first polymeric layer above at least a portion of the first layer of metal comprises depositing the first polymeric layer over the layer of sacrificial photoresist. The method may further comprise: etching an opening in the flexible polymeric substrate; and removing the sacrificial photoresist via the opening so as to provide a gap between the first and second layers of metal in the region previously occupied by the sacrificial photoresist. The method may further comprise sealing the opening so as to enclose the gap. The method may further comprise depositing a base layer of polymeric material over the first metal layer, wherein said positioning a first polymeric layer above at least a portion of the first layer of metal comprises bonding the first polymeric layer to the base layer of polymeric material. According to certain aspects, the flexible polymeric substrate may comprise liquid crystal polymer and each of the first and second polymeric layers may comprise parylene.

According to another aspect, the present disclosure relates to a method for obtaining a measurement of pressure in an environment within a subject, comprising: irradiating an implanted pressure sensor system in the subject by wirelessly transmitting radiowaves to the implanted pressure sensor system to power the system, wherein the implanted pressure sensor system comprises a pressure sensor, an integrated circuit electrically coupled to the pressure sensor, and an antenna electrically coupled to the integrated circuit; and receiving data from the implanted pressure sensor system by radiowaves, wherein the data represents information indicative of the pressure. The pressure sensor system may include a pressure sensor according to any embodiment or formed according to any method disclosed herein. According to certain aspects, the environment may be an eye.

According to another aspect, the present disclosure relates to a method for assessing the effects of an agent on intraocular pressure in an eye of a subject, comprising: administering the agent to the subject; powering an implanted pressure sensor system in the eye by wirelessly transmitting radiowaves to the implanted pressure sensor system, wherein the implanted pressure sensor system comprises a pressure sensor, an integrated circuit electrically coupled to the pressure sensor, and an antenna electrically coupled to the integrated circuit; and receiving data from the implanted pressure sensor system by radiowaves, wherein the data represents information indicative of the pressure. In certain embodiments, the agent is a biologically active molecule. In certain embodiments, the method for assessment may include comparing the data received from a control subject, wherein the control subject is the same subject prior to administration of the agent or a second subject which has not been administered the agent.

According to another aspect, the present disclosure relates to a non-human animal having implanted therein a pressure sensor according to any embodiment disclosed herein.

BRIEF DESCRIPTION OF THE DRAWINGS

The present disclosure describes illustrative embodiments that are non-limiting and non-exhaustive. Reference is made to certain of such illustrative embodiments that are depicted in the figures, in which:

FIGS. 21A and 21B is schematic view of a third-order harmonic passive tag for IOP monitoring (top view (left) and cross-sectional view (right)) according to one embodiment.

FIG. 22A-H are schematic views depicting various stages of another method for fabricating an embodiment of a compact-size tag for monitoring IOP inside the mouse eye according to one embodiment.

FIG. 23 illustrates a packaged parylene tag (left) and its implantation inside the mouse eye (right) according to one embodiment.

FIG. 24 is a schematic view of a setup for in-vivo testing according to one embodiment.

FIG. 25 is a plot of measured resonance frequency shift for the change of IOP. (Normalized and fitted from the originally corrected data) according to one embodiment.

FIG. 26 is a block diagram of fully wireless implantable micro-system according to one embodiment.

FIG. 27 is a top level schematic of a SAR ADC according to one embodiment.

FIG. 37 is a base station functional block diagram according to one embodiment.

FIG. 38 shows stained micrographs under 50× magnification used in histological studies of LCP (a) after 7 days, (b) after 14 days, and (c) after 28 days; and parylene coated LTCC (d) after 7 days, (3) after 14 days, and (f) after 28 days.

FIG. 39 illustrates measurements of fibrous encapsulation after 7 days of implantation for various materials.

FIG. 40 illustrates measurements of fibrous encapsulation after 14 days for the materials of FIG. 39.

FIG. 41 illustrates measurements of fibrous encapsulation after 28 days for the materials of FIG. 39.

FIG. 42 shows a first surgical implantation of a tadpole IOP device.

FIG. 43 shows a first implantation of CTR IOP device.

FIG. 44 shows a dummy device implantation.

FIG. 45 shows a LED device active in mouse surgery.

FIG. 46 is a plot showing power received using RF powering for both LTCC and Silicon devices.

FIG. 60 is a plot showing the intensity area of a first LED device when tested ex-vivo according to one embodiment.

FIG. 61 is a plot showing the LED power consumption when tested ex-vivo using wireless RF powering for the device of FIG. 60.

FIG. 62 is a plot showing the intensity area of a second LED device when tested ex-vivo according to one embodiment.

FIG. 63 is a plot showing the LED power consumption when tested ex-vivo using wireless RF powering for the device of FIG. 62.

FIG. 64 is a plot showing the intensity area of the LED device of FIG. 60 when implanted in the anterior chamber of a mouse eye for 1 month.

FIG. 65 is a plot showing the power consumption of the LED device of FIG. 60 when implanted in the anterior chamber of a mouse eye for 1 month.

FIG. 69 is a plot showing an analysis of efficiency of specific antenna types connected to an ASIC rectifier circuit under different load conditions according to one embodiment.

FIG. 70 is a schematic diagram show a condition for matching two complex impedances that lie outside a 1+jω circle. $Z_L$ and $Z_S$ are load impedance and source impedance respectively. $Z_1$ and $Z_2$ are inductors or capacitors for matching purposes.

FIG. 71 is a plot showing a measurement circuit output and a relationship between capacitive load and frequency output according to one embodiment.

FIG. 72 is a plot showing a comparison of measurement output and transmission demodulation for a given capacitance according to one embodiment.

FIG. 73 shows plots of output data of a measurement system using a MEMS pressure sensor in a pressure chamber according to one embodiment.

FIG. 74 is a block diagram of a coherent double sampling capacitance to voltage converter according to one embodiment.

DETAILED DESCRIPTION

Figure 1A:
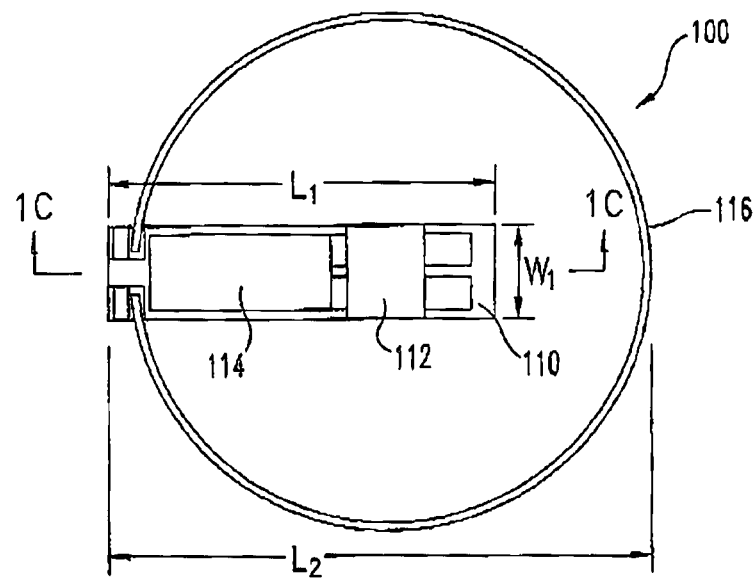
FIG. 1A is a top plan view of an embodiment of an implantable pressure sensing system.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims.

Various embodiments of pressure-sensing devices and systems are disclosed herein, as are various components useful in the same and various methods of making and using the same. In certain embodiments, capacitive pressure sensors are significantly smaller than prior art devices, yet are as sensitive as, or more sensitive than, those prior art devices. The capacitive pressure sensors thus can be deployed in a greater variety of destinations, as they can fit in more size-restricted regions. In other or further embodiments, the capacitive pressure sensors are extremely thin and/or include a flexible substrate, such as, for example, a polymer-based material. The pressure sensors thus can conform to a surface curvature or profile at an implantation region. For example, a pressure sensor may be implanted within a cavity or chamber of an animal subject or, more particularly, a human or other mammalian subject, such as, for example, within the anterior chamber of the eye, e.g. of a mouse. It shall be understood that the disclosed pressure sensors may also be implanted or otherwise operated in non-biological small scale environments where space or access is limited. The substrate can conform to at least a portion of a wall of the anterior chamber, which allows the sensor to more readily fit within the small space of the anterior chamber and/or which reduces or eliminates irritation, inflammation, and/or other complications that could result from an inflexible or rigid substrate body. In still other or further embodiments, the capacitive pressure sensors are biocompatible, such that they can be implanted within a subject without being rejected by the body of the subject. As used herein, the term "subject" applies to any suitable animal (e.g., mammal) within which a pressure sensor is or can be implanted. One or more of the foregoing advantages, and/or or one or more other advantages, of various embodiments of pressure sensors and systems will be apparent from the following discussion. Similarly, advantages of methods for making and using such pressure sensors will also be evident.

Figure 2:
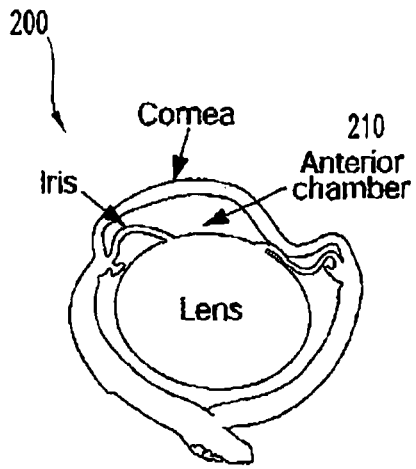
FIG. 2 is a cross-sectional view of a mouse eyeball.
Figure 3:
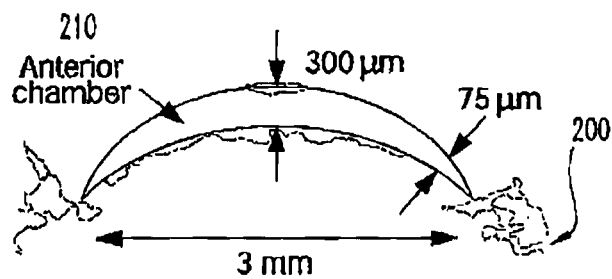
FIG. 3 is an ultrasound image of a mouse eyeball that has been annotated to depict various dimensions of the anterior chamber thereof.
Figure 4:
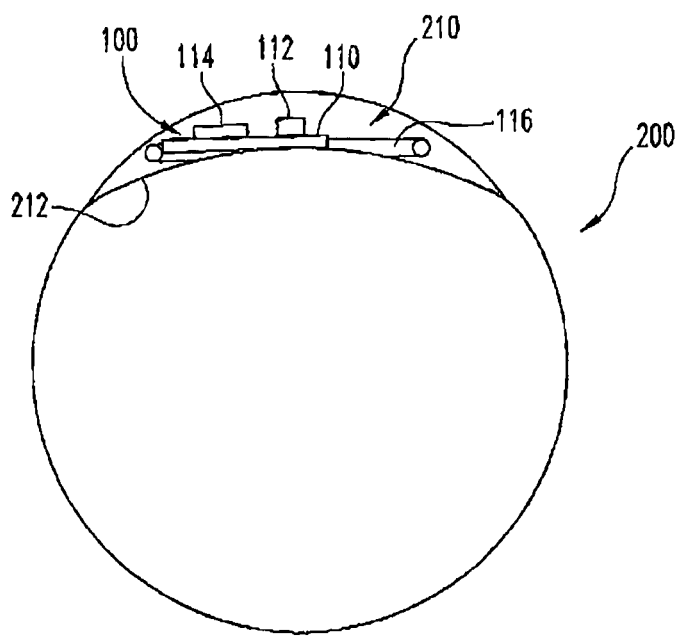
FIG. 4 is a schematic cross-sectional view of an embodiment of a pressure sensing system, such as that of FIG. 1A, implanted within the anterior chamber of a mouse eyeball.

Much of the following disclosure is directed to embodiments of capacitive pressure sensors that can be implanted in the anterior chamber of the eye of a small mammalian subject, such as a mouse (see, e.g., FIGS. 2-4). In some embodiments, the capacitive pressure sensor is sufficiently small for implantation in the eye of a mouse, sufficiently sensitive to obtain the desired pressure readings, and/or is capable of long-term implantation in the eye of a mouse with little or no inflammation of the eye. Furthermore, certain embodiments of the pressure-sensing implants are configured for automated, remote, and/or continuous monitoring of the intraocular pressure (IOP) within the eye of a subject, in certain embodiments a mouse eye or a human eye.

Some embodiments of the present disclosure pertain to methods for monitoring the response of a non-human animal. In some embodiments, the method includes preparing an incision in the eye of the animal, and inserting an active pressure sensor through the incision into a space within the eye. Preferably, the sensor is powered by electromagnetic radiation, especially radio waves. Further, it is preferable that the sensor transmits pressure data by electromagnetic radiation, especially radio waves.

In yet other embodiments, the method includes providing a radio wave antenna on the sensor for the collection and transmission of radio waves. Preferably, the antenna is collapsible to a small size compatible with the size of the incision. In some embodiments, the antenna is fabricated from a material that expands back to a predetermined shape that is adapted and configured for collection and transmission of radio waves within the biological space of the animal.

Yet other embodiments of the present disclosure pertain to a sensor assembly implantable with in a media, and useful for measuring the pressure within the media. In some embodiments, the sensor assembly includes a sensor providing a signal corresponding to the pressure the media, a circuit for receiving the signal and providing an output to an antenna, the antenna being adapted and configured to not have a free end. In those applications in which the media is within the biological space of an animal, the lack of a free end makes the antenna more biocompatible, since there is no free end to cause irritation.

Yet other embodiments the present disclosure pertain to a sensor implantable in media within the biologic space of an animal. The antenna is preferably fabricated from a shape memory material, such that it can be collapsed to a first, smaller size prior to placement within the biologic space, and then expand according to the shape memory characteristics to a second, larger shape that is more compatible with the biologic space, and which in some embodiments is further adapted for the transmission or receipt of radio waves within a predetermined frequency band.

Still further embodiments of the present disclosure pertain to an apparatus for measuring pressure within the media. In some embodiments the sensor is of the capacitance type, and is accompanied by a circuit that provides for signal processing of the capacitance signal. In one embodiment, the sensor interfaces with circuitry that provides the sensor signal at a higher order harmonic of the radiowave frequency that was utilized to power the sensor. In still further embodiments, the circuitry includes a low-power, 10 bit analog to digital converter that provides a high resolution signal of the changes in capacitance.

Yet other embodiments of the present disclosure pertain to a method of measuring a changing capacitance by use of a correlated double sampling capacitance to voltage converter. In some embodiments, this signal processing can be modified externally on a sensor that has been placed within the media whose pressure is being measured. For example, in those applications in which the base capacitance of the sensor varies, the circuitry can include a processor and repeatedly programmable memory that receives data corresponding to one or more circuit parameters. Receipt of this data can be used to vary these parameters during operation of the sensor. For example, the data can refer to parameters that will affect the sensitivity of the circuit to 1/F noise, data refers to the tuning of a reference capacitor, or data useful in modifying characteristics of a common mode rejection circuit.

Various embodiments of the present disclosure demonstrate the feasibility of IOP monitoring inside a mouse eye using a miniature 3rd order harmonic tag or chip that is useful for large population glaucoma studies in the future. A novel packaging approach is introduced to implement an ultra-small form factor implant that is thin enough to be implanted inside a mouse eye. A microelectricalmechanical system (MEMS) capacitive pressure sensor is successfully integrated with a self-expandable Nitinol antenna and a light emitting diode (LED) within the small tag. Other embodiments include use of the miniature $3^{rd}$ order harmonic tag in an eye of a human or other animal.

Although this disclosure discusses this illustrative context in detail, it should be appreciated that the pressure sensors are readily used in other contexts. For example, as discussed further below, certain pressure sensors may be used within the heart of a subject (e.g., a human) and/or within the vasculature of the subject. Some pressure sensors can be used to monitor the pressure of cerebrospinal fluid. Others can be positioned within silicone breast implants to sense a change in pressure due to rupture. A wide variety of other applications are also possible.

Figure 1B:
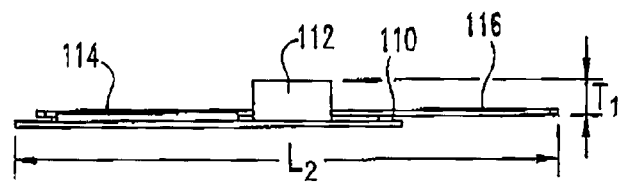
FIG. 1B is a side elevation view of the system of FIG. 1A.
Figure 1C:
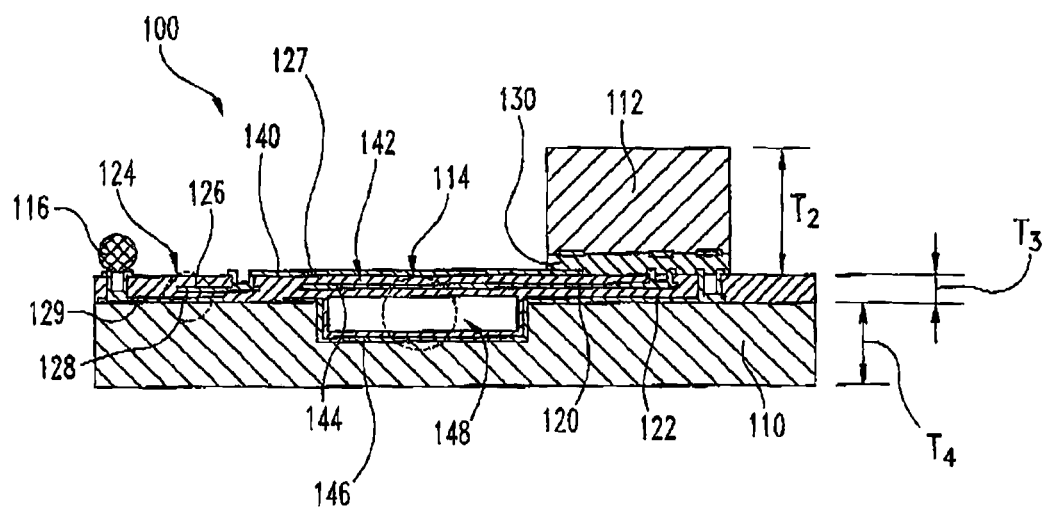
FIG. 1C is a cross-sectional view of a portion of the system of FIG. 1A taken along the view line 1C-1C in FIG. 1A.

FIGS. 1A-1C depict one embodiment of a pressure-sensing implant, or pressure-sensing system 100, that is configured to be implanted in the eye of an animal. In particular, the pressure-sensing system 100 is configured to be implanted in the eye of a mouse. It shall be understood that the system 100 may also be sized and adapted for implantation in a human eye or other animal eye. The pressure-sensing system 100 includes a substrate 110 that has multiple components mounted thereto and/or integrated therewith. In the illustrated embodiment, the pressure-sensing system 100 includes an integrated circuit (IC) 112, a pressure sensor 114, and an antenna 116 that are mounted to or integrally formed with the substrate 110. In view of the present illustrative context in which the pressure-sensing system 100 is used, the pressure sensor 114 may also be referred to as an IOP monitoring sensor.

As shown in FIG. 1C, the integrated circuit 112 can be electrically coupled with each of the pressure sensor 114 and the antenna 116 so as to be able to electrically communicate therewith. In particular, separate portions of the pressure sensor 114 can be coupled with the integrated circuit 112 via a pair of electrical leads 120, 122, as discussed further below. The pressure sensor 114 can be configured to provide data (e.g., capacitance values) to the integrated circuit 112, which can be configured to store the data, derive information from the data (e.g., derive calculated or estimated pressure values from the capacitance values), and/or deliver the data and/or the derived information to the antenna 116 for delivery to a remote data storage and/or analysis system (e.g., a computer or other electronic device, not shown).

In the illustrated embodiment, the integrated circuit 112 interfaces with the antenna 116, which in one embodiment can be an inductive loop antenna, via a metal-insulator-metal (MIM) capacitor 124, the capacitor 124 providing for radio-frequency (RF) matching between the antenna 116 and the integrated circuit 112. A first electrode, or capacitive plate 126, of the MIM capacitor 124 is coupled with the integrated circuit 112 via at least one electrical lead 127, and second electrode, or capacitive plate 128, of the MIM capacitor 124 is coupled with the antenna 116 via at least one additional electrical lead 129. Other and/or additional suitable electrical connections between the integrated circuit 112 and the antenna 116 are possible.

For a desired RF power transfer between two components (e.g., maximum or optimized power transfer), a conjugate matching may be used. Connecting the MIM capacitor 124 to the highly inductive loop antenna 116 can provide approximate conjugate matching between the antenna and the integrated circuit, which can provide a desirable power transfer (e.g., can maximize or optimize power transfer) from the antenna to the RF matching circuit in the integrated circuit 112. In certain embodiments, there may be no other electrical components between the antenna 116 and the integrated circuit 112, and the RF powering circuit can be embedded in the integrated circuit 112. In certain embodiments, the diameter of the loop antenna 116 may be sized to circumscribe the iris or cornea. In certain embodiments, the values for the matching may be determined as shown in Appendix A.

In various embodiments, the antenna 116 is capable of transmitting signals provided by the integrated circuit 112 to any suitable receiver (not shown) that is remote from the system 100 (e.g., at a position external to the subject within which the system 100 has been implanted). The signals may then be stored and/or processed remotely by any suitable processor (not shown). In such a manner, data regarding IOP within the eye of a mouse or other subject can be monitored on a regular and/or continuous basis. Such monitoring may be automated. In other or further embodiments, the antenna 116 is capable of receiving signals from a source (e.g., a computer or other electronic device) that is remote from the system 100. For example, the system 100 may be remotely programmable and/or controllable by the external source. In still other or further embodiments, the antenna 116 may be used to provide power to the system 100. Stated otherwise, the antenna 116 can be used to relay information to and/or from the integrated circuit 112, and in other or further embodiments, the antenna 116 can be used to provide power to the integrated circuit 112. In some embodiments, RF power received by the antenna can be transferred to an RF powering circuit within the integrated circuit 112. The RF powering circuit can be a rectifier, which can include diodes and capacitors. The rectifier can convert the RF power to a DC voltage that is used to power the integrated circuit 112. In some embodiments, wireless powering and communication such as that disclosed in Chow et al., "Fully Wireless Implantable Cardiovascular Pressure Monitor Integrated with a Medical Stent," *IEEE Transactions on Biomedical Engineering*, Vol. 57, No. 6, 1787-96 (June 2010), the entire contents of which are hereby incorporated by reference, may be used.

In the illustrated embodiment, the antenna 116 comprises a self-expandable loop of shape-memory material, such as nickel titanium (Nitinol™). Use of a shape-memory material can aid with implantation of the system 100, as the antenna 116 may have a compressed configuration during implantation, and after implantation, may naturally expand to its looped shape, for example, due to the body temperature of the subject. The compressible and expandable nature of the antenna 116, and the small size of the substrate 110, can permit the system 100 to be easily injected into place. For example, in some embodiments, the system 100 can be packaged in a compressed state within a microneedle, such as that disclosed in John et al., "Intraocular Pressure in Inbred Mouse Strains," *Investigative Ophthalmology & Visual Science*, Vol. 38, No. 1, 249-53 (January 1997), the entire contents of which are hereby incorporated by reference herein. The system 100 can be urged from the interior of the microneedle into the anterior chamber, and can then be permitted to transition to an expanded state.

The integrated circuit 112 can comprise any suitable configuration or construction. The integrated circuit 112 can be an application-specific integrated circuit (ASIC), which can be programmed or otherwise configured to achieve any of the actions described herein, as appropriate. In various embodiments, the integrated circuit 112 comprises a complementary metal-oxide-semiconductor (CMOS) integrated circuit (IC). The integrated circuit 112 can be programmed for any suitable functionality in any suitable manner. As shown in FIG. 1C, the integrated circuit 112 may be coupled with other portions of the system 100 via any suitable adhesive 130. For example, in the illustrated embodiment, the adhesive 130 comprises a layer of Z-axis anisotropic conductive adhesive (ACA). The integrated circuit 112 may desirably be relatively thin so as to reduce the bulk or overall footprint of the system 100. The integrated circuit 112 and the adhesive 130 can define a thickness $T_2$. In various embodiments, the thickness $T_2$ can be no greater than about 100, 125, 150, 175 or 200 microns, or can be within a range of from about 100 to about 200 microns or from about 125 to about 175 microns. In some embodiments, which may be particularly well-suited for use with mouse eyes, the thickness $T_2$ can be about 150 microns.

As shown in FIGS. 1A and 1B, the integrated circuit 112 may be positioned at a generally central region of the expanded system 100. For example, in the illustrated embodiment, the integrated circuit 112 is positioned at a longitudinal end of the elongated substrate 110 (see FIG. 1A), or stated otherwise, is positioned closer to one longitudinal end of the substrate 110 than the other longitudinal end thereof. The antenna 116 can be coupled with the system 100 at the opposite longitudinal end of the substrate 110, and may encircle, circumscribe, or otherwise encompass the portion of the substrate 110 to which the integrated circuit 112 is coupled. The integrated circuit 112 can be relatively thick, as compared with other components of the system 100 (e.g., the pressure sensor 114 and the antenna 116). Accordingly, the system 100 can be generally thinner at its periphery and thicker at a central region thereof. Such an arrangement can correspond to the shape of the anterior chamber of a mouse eye within which the system 100 can be implanted, as discussed further below.

Much of the following discussion focuses on the substrate 110 and the pressure sensor 114. The substrate 110 can desirably permit the system 100 to bend, flex, bow, curve, or otherwise conform to a rounded or otherwise curved surface contour. The substrate 110 may also have malleable, non-abrasive, or atraumatic edges and/or corners that are capable of reducing or eliminating irritation or inflammation. For example, the substrate 110 can be thin and/or can comprise a flexible material. The pressure sensor 114 can define a very small area, yet can be highly sensitive, e.g., to fluid pressure fluctuations. These and/or other properties of the substrate 110 and the pressure sensor 114 can be particularly useful in implanting the system 100 in the eye of a mouse, as discussed further below, although it will be understood that system 100 can also be implemented in the eye of a human or other animal as well.

The substrate 110 can be ultra-thin and flexible. In certain embodiments, the substrate 110 can comprise a single layer of a material that is biocompatible, chemically inert, flexible, conformable, strong, durable, and/or readily shaped via micro-machining. The substrate 110 may have desirable electro-mechanical properties, such as a relatively low dielectric constant, a low loss tangent, a low Young's modulus, and/or suitable compatibility with conventional micro-fabrication processes. For example, the substrate 110 can comprise a polymeric material, such as liquid crystal polymer (LCP).

A maximum thickness $T_4$ of the substrate 110 (see FIG. 1C) can be extremely small. In various embodiments, the thickness $T_4$ is no greater than about 15, 20, 25, 30, 35, 40, 45, or 50 microns, or is within a range of from about 15 to about 50 microns, from about 20 to about 30 microns, or from about 24 to about 26 microns. In some embodiments, the thickness $T_4$ is about 25 microns, which can be desirable for applications in which the system 100 is implanted in a mouse eye. Such a thickness can permit at least a portion of the substrate 110 to readily conform to a posterior wall of the anterior chamber of a mouse eye, yet provide sufficient strength and support for other components of the system 100 that are mounted thereto and/or integrated therewith. Moreover, a relatively thick substrate 110 can be more resistant to deformation (e.g., localized deformation) than other portions of the system 100, which can aid in operation of the pressure sensor 114, as discussed further below.

With reference to FIG. 1A, the substrate 110 can define an extremely small area. In some embodiments, the substrate 110 is substantially rectangular, although other suitable shapes are possible. In various embodiments, a length $L_1$ of the substrate 110 can be no greater than about 0.5, 0.75, 1.0, 1.1, 1.2, 1.3, 1.4, or 1.5 millimeters, or can be within a range of from about 0.5 to about 1.5, from about 0.75 to about 1.5, or from about 1.0 to about 1.5 millimeters. In various embodiments, a width $W_1$ of the substrate can be no greater than about 0.25, 0.5, 0.6, 0.65, 0.7, 0.75, 0.8, 0.9, or 1.0 millimeters, or can be within a range of from about 0.25 to 1.0, 0.5 to about 1.0, or 0.6 to about 0.8 millimeters. In various embodiments, a perimeter of the substrate 110 defines an area of no greater than about 0.1, 0.2, 0.3, 0.4, 0.5, 0.6, 0.7, 0.8, 0.9, 1.0, 1.25, 1.5, or 2.0 millimeters$^2$. In some embodiments, which may be particularly well-suited for use with mouse eyes, the length $L_1$ can be about 1.3 millimeters and the width $W_1$ can be about 0.7 millimeters.

As previously discussed, the substrate 110 can be relatively flexible. For example, in various embodiments, the substrate 110 can have a Young's modulus that is within a range of from about 10 to about 40 GPa, or that is no greater than about 10, 20, 30, or 40 GPa.

The pressure sensor 114 can comprise a microelectromechanical system (MEMS) capacitive pressure sensor. In certain embodiments, the pressure sensor 114 can be integral with the substrate 110, such that at least a portion thereof comprises a polymeric material. Moreover, as further discussed below, the pressure sensor 114 can comprise other polymeric materials that differ from those used in the substrate 110. Accordingly, the pressure sensor 114 may be referred to as a polymer-based pressure sensor.

With reference to FIG. 1C, the pressure sensor 114 can include one or more layers of a coating material, or a form factor material 140, that is positioned above and/or is in abutting contact with the substrate 110. The material 140 can have desirable form factor properties for forming a membrane 142, which is configured to be displaced relative to the substrate 110, as discussed further below. The material 140 can desirably be chemically and/or biologically inert and biocompatible. In some embodiments, the material 140 can be suitable for multi-layer processing (e.g., via any suitable deposition process, such as vacuum deposition), and it can provide a conformal coating. The material 140 may be deposited as one or more thin layers or films, and it may exhibit a low coating temperature. In some embodiments, the material 140 may be transparent. The material 140 can desirably be flexible, or have a relatively low stiffness (e.g., compared with a stiffness of the substrate 110), which can permit the membrane 142 to bend, deform, or otherwise deflect toward the substrate 110 when pressure is applied to the implanted system 100. As previously discussed, the substrate 110 may not bend or deform due to the increased pressure, or may deform to a much lesser extent, such that the substrate 110, and a lower electrode supported thereby, can serve as a reference against which changes in the membrane 142 can be measured. In the illustrated embodiment, the material 140 comprises parylene. In various embodiments, the material 140 has a Young's modulus of no greater than about 3, 3.5, 4, or 4.5 GPa. In some embodiments, which may be particularly well-suited for use with mouse eyes, the material 140 comprises parylene that has Young's modulus of about 4 GPa. In various embodiments, a thickness $T_3$ of the material 140 can be no greater than about 1, 2, 3, 4, 5, 6, 7, 8, 9, or 10 microns, or can be within a range of from about 1 to 10 microns. In the illustrated embodiment, the thickness $T_3$ is about 5 microns.

The pressure sensor 114 can further include a pair of electrodes or capacitive layers or plates 144, 146 that are spaced or separated from each other. The plates 144, 146 can comprise any suitable conductive material, and at least the upper plate 144 may be extremely thin and flexible. In some embodiments, at least the upper plate 144 can comprise a thinly deposited layer of Ti/Au (titanium/gold). The plates 144, 146 can be electrically coupled with the integrated circuit 112 via the leads 120, 122, respectively. In some embodiments, the upper plate 144 and its lead 120 are sandwiched between layers of the material 140 (e.g., parylene). The lower plate 146 and its lead 122 may also have a layer of the material 140 deposited thereon.

The pressure sensor 114 can define an insulating or dielectric region 148 between the capacitive plates 144, 146. In the illustrated embodiment, the dielectric region 148 comprises an air-filled gap. However, it shall be understood that the dielectric region 148 may comprise any material (e.g., gas, liquid, solid, gel) which allows the upper or lower plates 144, 146 to move or flex relative to one another, thereby creating a change in capacitance of the sensor 114. The specific medium or material of the dielectric region 148 may be chosen based on the needs of the particular application and dynamic range desired. Operation of the pressure sensor 114 and properties of the membrane 142 and dielectric region 148 are discussed further below.

As previously discussed, embodiments of the system 100 can be well-suited for implantation into the eye of a mouse for monitoring of the IOP within the eye. As shown in FIGS. 2-4, a mouse eyeball 200 includes an anterior chamber 210 that includes a bowed or curved posterior wall 212. The anterior chamber 200 is crescent-shaped in cross-section, such that it defines a non-uniform thickness. A maximum thickness of the anterior chamber 200 is about 300 microns, whereas a thickness near the edges thereof is about 75 microns. A maximum diameter of the anterior chamber 200 is about 3 millimeters. Embodiments of the system 100 are capable of fitting within the limited volume of the anterior chamber 200 and of conforming to the shape of the posterior wall 212.

For example, with reference to FIGS. 1A, 1B, and 4, a maximum diameter of the system 100, which is represented by the length $L_2$, can be no greater than about 2 millimeters. A maximum thickness $T_1$ of the system 100 can be no greater than about 250 microns, with the maximum height being at or near the center of the system 100. Accordingly, the system 100 can fit well within the anterior chamber 200. In other embodiments, the length $L_2$ can be no greater than about 1, 1.5, 2.5, or 3 millimeters, and in thickness $T_1$ can be no greater than about 100, 150, 200, or 300 microns.

In certain embodiments, such as that schematically depicted in FIG. 4, the area available for the pressure sensor 114 is less than about 0.5 millimeters$^2$ (e.g., fits within a square region measuring about 700 microns by about 700 microns). Additionally, the pressure sensor 114 can have a limited thickness, and may be no greater than about 150 microns. Further complicating the pressure sensing is the fact that the posterior wall 212 is curved. It thus can be desirable for the substrate 110 to curve so as to conform to the posterior wall 212 and/or to be flexible or otherwise atraumatic so as to reduce, minimize, or eliminate damage to the eye tissue.

As previously mentioned, the maximum width $W_1$ of the substrate 110 can be no greater than about 700 microns, in the illustrated embodiment, and the antenna 116 can be originally packaged in a narrow or constricted state, and may self-expand after implantation. Accordingly, the system 100 can be well suited for implantation through an incision that is no greater than about 700 microns in length. This can minimize damage of the eye tissue during surgery and permit re-sealing of the incision without sutures.

Figure 5A:
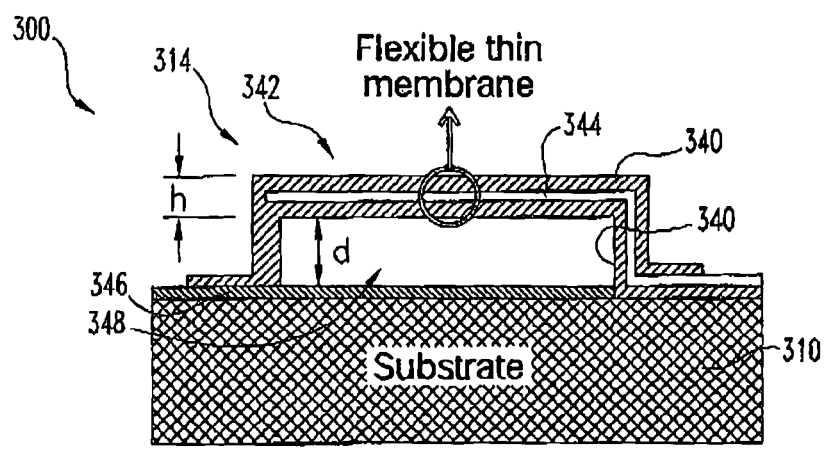
FIG. 5A is a cross-sectional view of an embodiment of a pressure sensor in an uncompressed state.
Figure 5B:
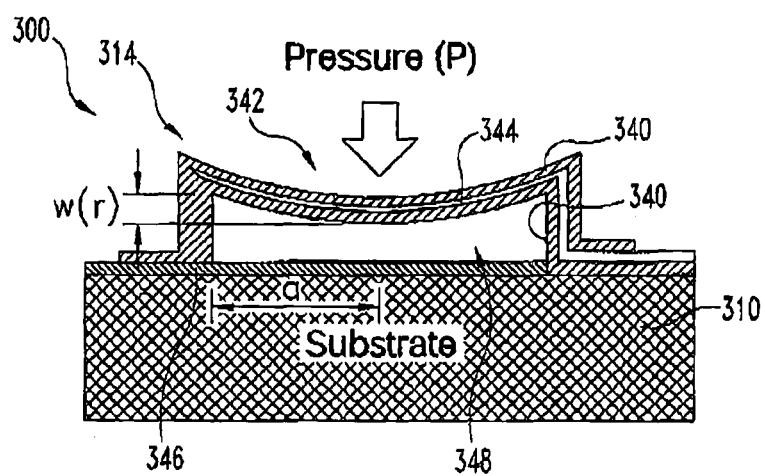
FIG. 5B is a cross-sectional view of the pressure sensor of FIG. 5A in a compressed state.

FIGS. 5A and 5B illustrates a portion of another embodiment of a pressure-sensing implant or system 300 that includes a pressure sensor 314, which can resemble the previously discussed pressure-sensing system 100 and pressure sensor 114, respectively, in certain respects. For example, the pressure-sensing system 300 can closely resemble the pressure-sensing system 100, aside from any differences in their respective pressure sensors 314, 114. Accordingly, like features are designated with like reference numerals, with the leading digits incremented to "3." Relevant disclosure set forth above regarding similarly identified features thus may not be repeated hereafter. Moreover, specific features of the pressure-sensing system 300 or the pressure sensor 314 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the system 300 and the pressure sensor 314. Any suitable combination of the features and variations of the same described above with respect to the system 100 and the pressure sensor 114 can be employed with the system 300 and the pressure sensor 314, respectively, and vice versa. This pattern of disclosure applies equally to further embodiments depicted in subsequent figures and described hereafter.

The pressure sensor 314 comprises a capacitive pressure sensor that has a high sensitivity to pressure changes, a low sensitivity to temperature fluctuations, and a low power consumption. The pressure sensor 314 is formed atop a substrate 310, such as the substrate 110 discussed above. The pressure sensor 314 includes a diaphragm or membrane 342, which includes an upper electrode or capacitive plate 344 that is sandwiched between coating material or form factor material 340, such as the material 140 discussed above. The pressure sensor 314 further includes a lower electrode or capacitive plate 346, which is in abutting contact with the substrate 310. A dielectric region 348 is positioned between the plates 344, 346. Again, it shall be understood that the dielectric region 348 may comprise any material (e.g., gas, liquid, solid, gel) which allows the upper or lower plates 344, 346 to move or flex relative to one another, thereby creating a change in capacitance of the sensor 348. The specific medium or material of the dielectric region 348 may be chosen based on the needs of the particular application and dynamic range desired. In the illustrated embodiment, the lower plate 346 does not include a coating material 340 over an upper surface thereof in the vicinity of the dielectric region 348.

The pressure sensor 314 is shown in a cross-sectional side elevation view. As viewed from above, the membrane 342 portion of the pressure sensor 314 is substantially circular. As the pressure of the environment that surrounds the pressure sensor 314 increases, the membrane 342 can be deflected toward the substrate 310, as can be seen by comparing FIG. 5A to 5B. This deflection changes the distance, and therefore the capacitance, between the fixed bottom electrode 346 and the flexible top electrode 344. The deflection of the circular membrane 342 and the change in capacitance of the pressure sensor 314 can be estimated using known methods. For example, suitable methods for estimating the change in capacitance for a deflected circular membrane are disclosed in Schellin et al., "Measurement of the mechanical behavior of micromachined silicon and silicon-nitride membranes for microphones, pressure sensors and gas flow meters," *Sensors and Actuators A*, vol. 41, 287-92 (1994) and in Fragiacomo et al., "Analysis of small deflection touch mode behavior in capacitive pressure sensors," *Sensors and Actuators A*, vol. 161, pp 114-19 (2010), the entire contents of which are incorporated by reference in their entirety herein. Generally, one or more complicated or nonlinear formulas, relationships, or algorithms can be used to relate a change in capacitance for a circular capacitor having known physical properties, such as the properties discussed below. While the embodiments discussed herein use circular geometries for the pressure sensor 314, it is noted that other geometries are also possible (e.g., square, rectangular, etc.).

The deflection caused by the applied pressure can be determined by the rigidity and residual stress of the membrane 342. For example, the maximum deflection $w_0$ at the center of the membrane 342 can be determined as follows $$w_0 = \frac{Pa^4}{64D + 4\sigma ha^2} \quad \text{(Equation 1)}$$

where P is the applied pressure to the membrane 342, D is the flexural rigidity of the membrane 342, a is the radius of the upper electrode 344 (which may be roughly the same as the radius of the membrane 342), h is the thickness of the membrane 342, and $\sigma$ is the residual stress of the membrane 342. The flexural rigidity D can be expressed as $$D = \frac{Eh^3}{12(1-v^2)} \quad \text{(Equation 2)}$$

where E is the Young's modulus of the membrane 342 and v is the Poisson's ratio of the membrane 342. The residual stress of the membrane 342 can highly depend on the fabrication process conditions. For example, the residual stress D of thin parylene film that has experienced conventional micro-fabrication processes can be within a range of from about 30 to about 50 MPa. When considering the effect of the rigidity and residual stress on the membrane 344, the equation to describe the deflection of the membrane is as follows:

$$w(r) = w_0 \left[1 - \left(\frac{r}{a}\right)^2\right]^2 \quad \text{(Equation 3)}$$

where r is the distance from the center of the membrane. The capacitance at a given pressure is estimated from the deflection and the charge integral across the capacitor:

$$C = 2\pi\varepsilon \int_0^a \frac{r}{d - w(r)} dr \quad \text{(Equation 4)}$$

where d is the depth of the gap 348 between the top and bottom plates 344, 346 in the absence of a net compressive pressure (e.g., in the uncompressed state shown in FIG. 5A).

As previously discussed, in some embodiments, the substrate 310 can desirably have a maximum width $W_1$ (see FIG. 1) that is no greater than about 700 microns, which can be desirable for insertion of the pressure-sensing implant into the eye of a mouse. Accordingly, in some embodiments, the radius of the membrane 342 is no greater than 350 microns, such that the sensing area is no greater than about 0.38 millimeters$^2$. More generally, in various embodiments, the sensing area can be no greater than about 0.3, 0.4, or 0.5 millimeters$^2$.

Accordingly, fabrication methods for the pressure sensor 314 (and more generally, for the pressure-sensing device 300), and the dimensions and composition of the pressure sensor 314, can be selected, adjusted, determined, or otherwise result from a balancing of properties of components of the pressure sensor 314 and/or operational factors related thereto. For example, the depth d of the gap 348 and the thickness h of the membrane 342 can be determined from and/or limited based on the processes used in their fabrication and/or the desired sensitivity of the pressure sensor 314.

As a further example, it can be desirable to position the upper and lower electrodes 344, 346 as close as possible to each other so as to thereby improve sensitivity of the pressure sensor 314. However, in some instances, it can be undesirable to position the electrodes 344, 346 so close to each other such that, at higher pressures encountered within the eye of the mouse (or any other environment in which the sensor 314 may be positioned), the membrane 342 contacts the lower electrode 344. Such contact can skew or alter the manner in which the capacitance of the electrodes 344, 346 varies with further increases in pressure, or it may significantly curtail or even prevent any change in capacitance at these increasingly higher pressures. Accordingly, the contact can either complicate readings at the higher pressures or it may result in an upper limit (e.g., "saturation level") of pressure readings, thereby limiting the overall sensitivity or dynamic range of the pressure sensor 314.

Contact between the membrane 342 and the lower electrode 346 at higher pressures could also cause the membrane 342 to undesirably adhere to the lower electrode 346. Accordingly, when a high pressure of the environment surrounding the pressure sensor 314 that caused the adhesion is subsequently reduced, the membrane 342 could undesirably remain stuck to the lower electrode 346, which would inhibit pressure readings at the lower pressures and could, in some instances, permanently impede operation of the pressure sensor 314 (e.g., should the membrane 342 remain adhered to the lower electrode 346). Therefore, in many instances, it can be desirable for various parameters of the sensor 314, such as the depth d of the gap 348, the thickness h of the membrane 342, and/or the radius a of the upper electrode 346 of the membrane 342 to be selected so as to prevent contact between the membrane 342 and the lower electrode 346 at the highest pressures that are likely to be encountered in the environment into which the pressure sensor 314 is implanted, while maintaining a desired sensitivity of the sensor 314. In the context of mouse eyes, the highest IOP likely to be encountered within the anterior chamber can be about 70 mmHg above atmospheric pressure, although even higher pressures may be encountered in some cases. In the context of a human eye, the highest IOP likely to be encountered is about 80 mmHg. In the context of other environments (e.g., heart, vasculature, spinal fluid), higher or lower pressure ranges may be encountered. In various embodiments, the depth d of the gap 348 can be no greater than about 3, 4, 5, 6, or 7 microns, no less than about 3, 4, 5, 6, or 7 microns, within a range of from about 3 to about 7 microns, within a range of from about 4 to about 6 microns, or can be about 5 microns.

Discussed hereafter are illustrative methods for fabricating pressure sensors, such as the pressure sensors 114, 314 described above. Although the methods are focused on the creation of pressure sensors, it is understood that the methods can be altered and/or extended to include fabrication of the pressure-sensing systems 100, 300 in their entireties. For example, although procedural steps are not specifically discussed with respect to the coupling of integrated circuits or antennas with substrates, it is understood that such coupling is possible at any suitable stage of the fabrication of the pressure sensors 114, 314.

Some of the illustrative methods discussed hereafter employ sacrificial photoresist (PR) procedures, while others employ parylene membrane transfer procedures (e.g., parylene-to-parylene bonding). In either set of methods, a thin and biocompatible, conductive layer of Ti/Au is sandwiched between parylene layers to form a membrane. Other or further conductive layers are possible (e.g., one or more other metal layers), but this could result in changes to other parameters of the pressure sensors (such as gap thickness, membrane thickness, etc.). The sandwiched Ti/Au structure can be much more flexible than a metal or silicon membrane of the same thickness. The thickness of the parylene layers of the membrane can be selected or otherwise determined or formed so as to prevent the membrane from collapsing or tearing during fabrication. The sandwiched Ti/Au structure can be extremely thin, which can yield a very low effective Young's modulus of the membrane, thus making the membrane easier to deflect (e.g., more sensitive to pressure fluctuations). In various embodiments, the capacitive pressure sensors can be sufficiently sensitive to detect a pressure change of no less than about 0.5, 0.75, 1, 1.5, or 2 mmHg. For example, in some embodiments, the pressure sensors can desirably detect pressure changes of no less than about 1 mmHg. In various embodiments, the integrated circuit that is used can also assist in the sensitivity of the pressure sensing system. Accordingly, it can be desirable to use a suitable ASIC in connection with the physically sensitive pressure sensors, in some embodiments.

FIGS. 6A-6I depict an illustrative fabrication process that can be used to create a capacitive pressure sensor 414 (FIG. 6I), such as the capacitive pressure sensors 114, 314 discussed above. Specific dimensions, materials, and other features are provided with respect to this illustrative process. While such specific dimensions, materials, and features may constitute independently patentable subject matter, it should be understood that other suitable dimensions, materials, and features may be used in fabricating other capacitive pressure sensors in accordance with other embodiments of the present disclosure, and thus such dimensions, materials, and features are not necessarily meant to be limiting.

Figure 6A:
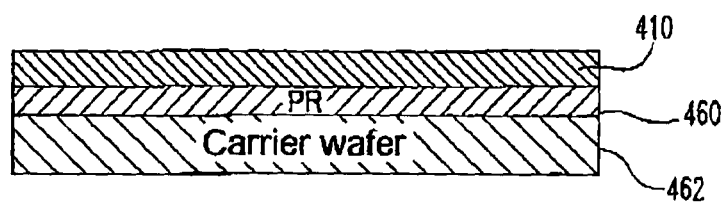
FIGS. 6A-6I are schematic views depicting various stages of a method for fabricating an embodiment of a pressure sensor.

With reference to FIG. 6A, a photoresist (PR) layer 460 is applied to a flexible LCP substrate 410, which can have a thickness of 25 microns (or other suitable dimensions discussed above). The PR layer 460 can comprise AZ1518, and can be spin-coated and hard-baked onto the substrate 410 for use as an adhesion layer. In certain embodiments, the substrate 410 can comprise UL TLARAM 3850, which is available from Rogers Corporation of Chandler, Ariz. The fabrication process for the LCP film can be similar to conventional Si-based MEMS processing. For ease of handling, the thin, flexible LCP substrate 410 and sacrificial PR layer 460 can be attached to a silicon carrier wafer 462.

Figure 6B:
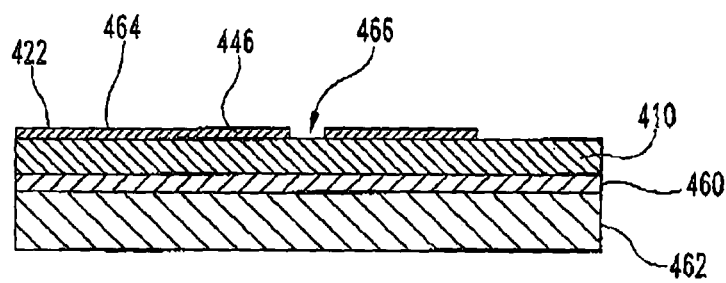
Figure 6C:
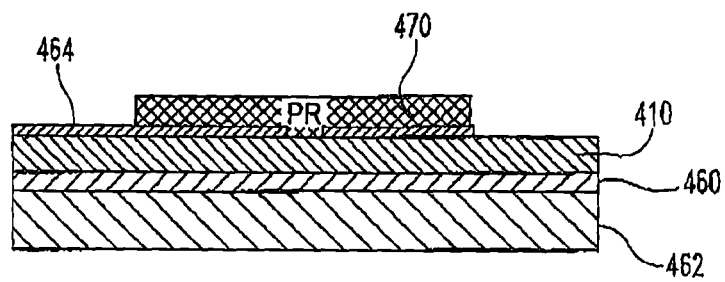
Figure 6D:
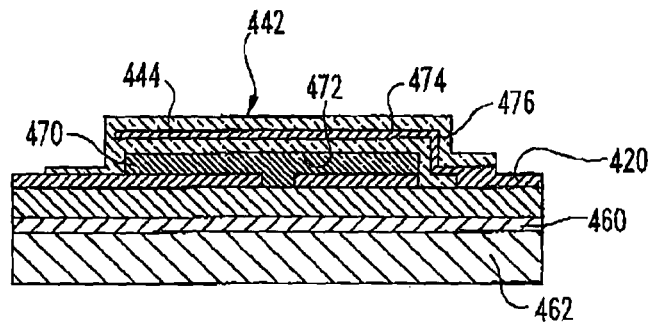
Figure 6E:
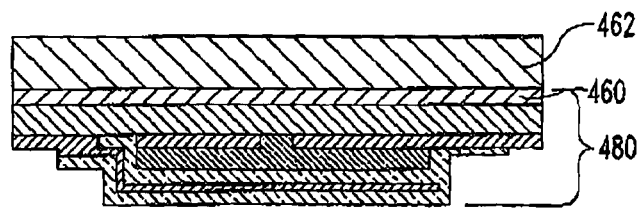
Figure 6F:
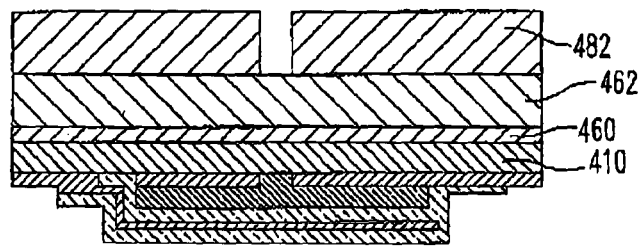
Figure 6G:
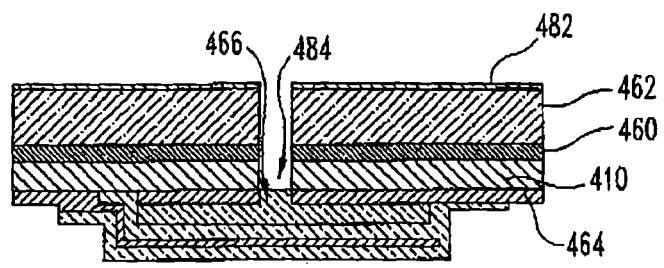
Figure 6H:
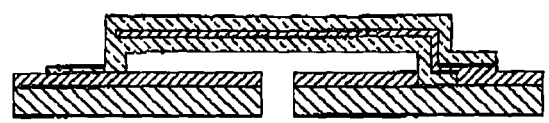
Figure 6I:
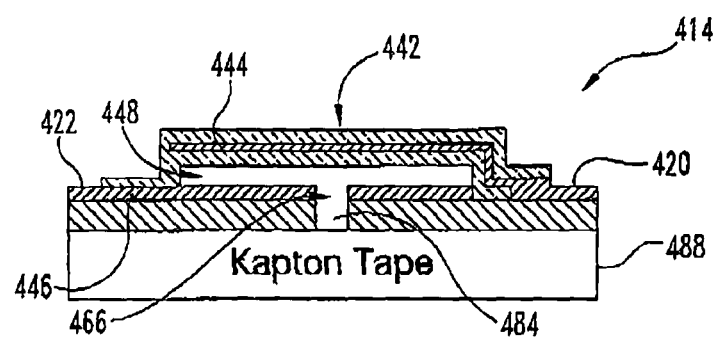

One or more layers of Ti/Au may be used as metallic or conductive layers for one or more of an upper and lower electrode 444, 446 (FIG. 6I). Ti/Au may be selected due to, for example, its biocompatibility. With reference to FIG. 6B, a layer of Ti/Au 464 can be sputtered onto (or otherwise applied to) a surface of the substrate 410 in an initial stage of formation of the lower electrode. To improve the Ti/Au adhesion, the LCP can be exposed to Ar (argon) ion bombardment in the sputtering system (which may be a Perkin Elmer 2400 sputter system) for 2 minutes. Ar ion bombardment under vacuum generates a TiC layer between Ti and LCP, which can play a role as a good adhesion layer. Then, the conductor or Ti/Au layer 464 is deposited. The Ti/Au layer 464 may have a thickness of about 0.5 microns. The Ti/Au is patterned with wet etching to form the lower electrode 446 and an associated electrical lead 422. In the illustrated embodiment, a pathway, channel, or opening 466 is provided in the Ti/Au layer 464, which is further discussed below.

With reference to FIG. 6C, a sacrificial PR layer 470 is deposited over at least a portion of the Ti/Au layer 464 using standard lithography processes. The sacrificial PR layer 470 can define a thickness that corresponds to the desired thickness of a dielectric region or gap 448 of the pressure sensor 414 (see FIG. 6I). The specific medium or material of the dielectric region 148 may be chosen based on the needs of the particular application and dynamic range desired. As discussed further below, the sacrificial PR layer 470 is eventually removed to thereby form the cavity or gap 448. In various embodiments, the sacrificial PR layer 470 can have a thickness of no greater than about 1, 1.5, 2, 2.5, or 3 microns. In the illustrated embodiment, the thickness is about 2 microns. The sacrificial PR layer 470 can comprise any suitable PR material, such as, for example, MICROPOSIT SC1827, which is available from Rohm and Haas Electronic Materials LLC of Marlborough, Mass.

As shown in FIG. 6D, a composite membrane 442 can then be created. A first parylene layer 472 can be deposited over the sacrificial PR layer 470. The first parylene layer 472 can have any suitable thickness, such as a thickness of no more than about 1, 2, 3, or 4 microns. In the illustrated embodiment, the first parylene layer 472 has a thickness of about 3 microns. The first parylene layer 472 can be deposited in any suitable manner, such as via a PDS 2010 system, which is available from Specialty Coating Systems of Indianapolis, Ind. In some embodiments, before metal deposition onto the first parylene layer 472, the sample can be etched with oxygen plasma (e.g., at 100 Watts for 20 seconds) in a Plasma-tech reactive-ion etching (RIE) system to improve Ti/Au adhesion on the parylene.

An upper Ti/Au layer 474 is deposited on the parylene layer 472 and patterned so as to form the upper electrode 446 and an associated electrical lead 420. The electrode portion of the Ti/Au layer 474 can be of any suitable thickness, depending on the desired properties of the sandwiched membrane 442. For example, the Ti/Au layer 474 can have a thickness of no more than about 0.2, 0.3, or 0.4 microns. In the illustrated embodiment, the Ti/Au layer 474 has a thickness of about 0.2 microns.

A second parylene layer 476 can be deposited over at least a portion of the Ti/Au layer 474. The second parylene layer 476 can have any suitable thickness, such as a thickness of no more than about 1, 2, 3, or 4 microns. In the illustrated embodiment, the second parylene layer 476 has a thickness of about 2 microns.

With reference to FIG. 6E, carrier wafer 462 can be separated from an upper portion 480 of the assembly by soaking the assembly in acetone. Once the upper portion 480 of the assembly has been released from the carrier wafer 462, it is flipped over and re-attached to the carrier wafer 462 via the spin-coated and hard-baked PR layer 460.

With reference to FIG. 6F, an additional PR layer 482 can be applied to the silicon carrier wafer 462. In particular, the PR layer 482 can be spin-coated onto the carrier wafer 462 and patterned as a mask for deep reactive ion etching (DRIE). The PR layer 482 can comprise, for example, AZ9260. In certain embodiments, the PR layer 482 can be relatively thick. For example, the PR layer 482 can have a thickness of no less than about 30, 40, or 50 microns. In the illustrated embodiment, the thickness is about 40 microns. Etch selectivity between LCP and PR can be approximately 1:1. Accordingly, the thickness of the PR layer 482, or PR mask, is desirably thicker than the combined thickness of the LCP substrate 410 and the carrier wafer 462 (which is slightly greater than about 25 or 30 microns, in the illustrated embodiment). Standard techniques for high aspect ratio photolithography with thick PR can be used.

With reference to FIG. 6G, a hole, via, or opening 484 is created in the substrate 410 using an advanced oxide etching (AOE) DRIE system. The opening 484 is provided to permit release of the sacrificial PR layer 470, as discussed further below. The opening 484 is desirably aligned with the opening 466 in the Ti/Au layer 464. The size of the opening 484 can be selected as a trade-off between efficient release of the sacrificial PR layer 470 (larger openings 484 are desirable) and degradation of the sensitivity of the substrate 410 to etching upon reduction of the sensing area (smaller openings 484 are more difficult to form). In various embodiments, the opening 484 can have a diameter that is no greater than about 50, 60, 70, 80, 90 or 100 microns, or is within a range of from about 50 to about 100 microns or from about 80 to about 100 microns. In the illustrated embodiment, the diameter is about 90 microns. In the illustrated embodiment, the etching is performed for about 90 minutes using low power (200 W) at a low etching rate of approximately 0.3 microns/minute. Higher power would reduce the etching time, but the resulting high temperatures could cause the PR mask to reflow. As can be seen by comparing FIG. 6F to 6G, the thickness of the PR mask 482 has been greatly reduced by the etching process.

With reference to FIG. 6H, the assembly is submerged into PR stripper (e.g., PRS 2000) for a suitable period for removal of all of the PR material that remains in the assembly—particularly the sacrificial PR layer 470. In the illustrated embodiment, the assembly is submerged in PRS 2000 PR stripper for 48 hrs at 80 degrees Celsius to achieve the PR removal. The assembly is then dried by a critical point drying (CPD) process.

With reference to FIG. 6I, fabrication of the pressure sensor 414 is completed by backside sealing of the openings 466, 484 in any suitable manner. In the illustrated embodiment, Kapton® tape 488, which is available from DuPont Electronics, is used. The tape can be about 50 microns thick. Thus sealed, the pressure sensor 414 includes a dielectric region or air gap 448 that separates the capacitive plates 444, 446. Again, it shall be understood that the dielectric region 448 may be filled with any material (e.g., gas, liquid, solid, gel) which allows the upper or lower plates 444, 446 to move or flex relative to one another, thereby creating a desired change in capacitance of the sensor 414.

Figure 7:
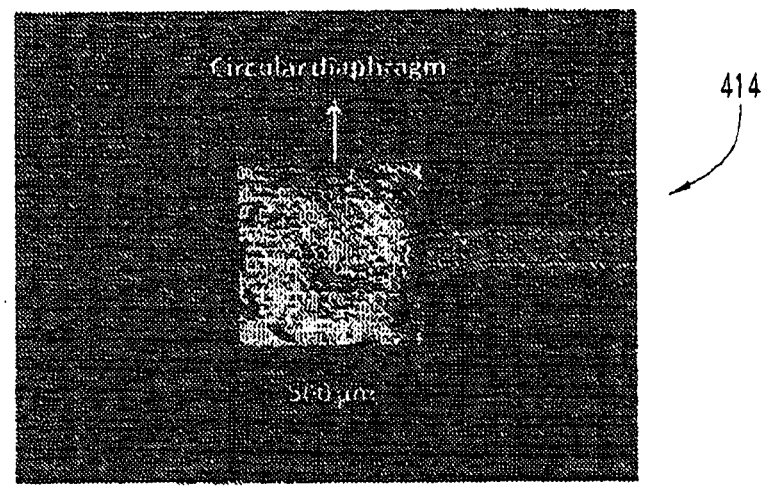
FIG. 7 is a top plan view of an embodiment of a pressure sensor that has been fabricated using the method of FIGS. 6A-6I.
Figure 8:
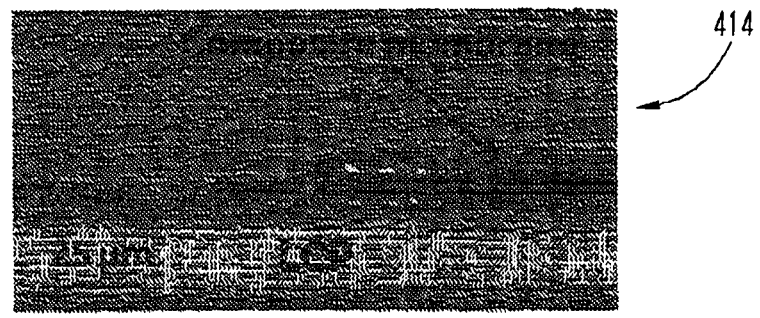
FIG. 8 is a cross-sectional view of the pressure sensor of FIG. 7.

FIGS. 7 and 8 show a top plan view and a cross-sectional view, respectively, of an illustrative embodiment of the pressure sensor 414 that was fabricated via the method depicted in FIGS. 6A-6I. The sensor 414 includes a diaphragm having a radius of about 250 microns, and fits within a volume of 500 microns×500 microns×100 microns. The pressure sensor 414 is suitably sized to be integrated on an implantable LCP tab for placement in the anterior chamber of a mouse eye.

Figure 9:
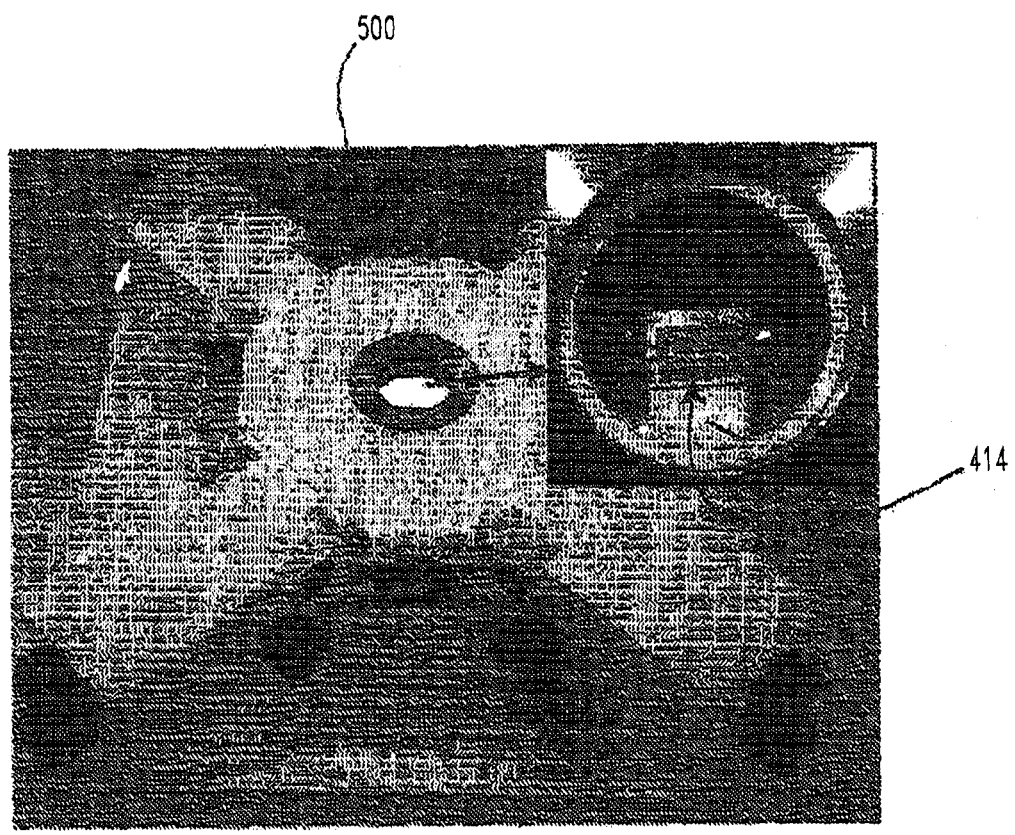
FIG. 9 is a perspective view of an embodiment of a pressure controlled chamber that is used to test the pressure sensor of FIG. 7, wherein the inset image in the upper right corner depicts a close-up view of the pressure sensor within the chamber.
Figure 10:
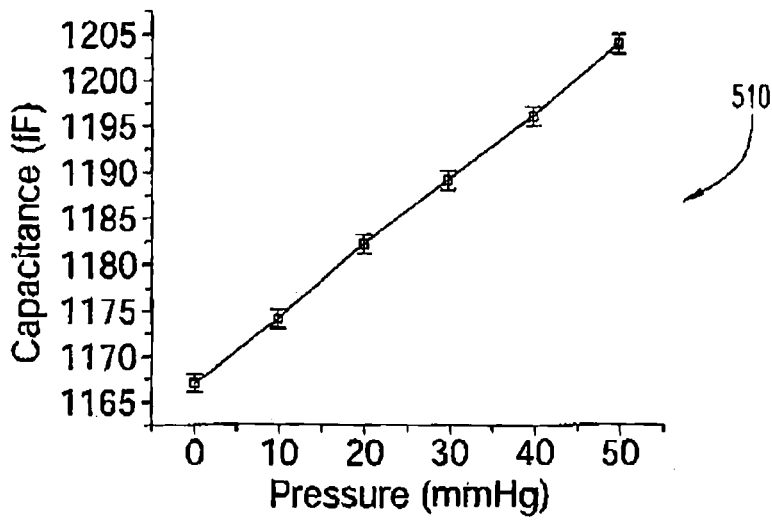
FIG. 10 is a plot of the capacitance of the pressure sensor of FIG. 7 as a function of pressure.

Testing of the pressure sensor 414 can be achieved by microprobing within a pressure-controlled chamber, such as within the probe station 500 supplied by MMR Technologies of Mountain View, Calif., shown in FIG. 9. The pressure range for the measurement of IOP of mice will normally vary from 5 to 40 mmHg above atmospheric pressure. Accordingly, to test operation of the pressure sensor 414 over a full range of standard operation, the response of the sensor 414 in the range of 0 to 50 mmHg above atmospheric pressure can be measured. The capacitance can be measured as the pressure is increased from low to high pressure using an inductance-capacitance-resistance (LCR) meter, such as a model 4284A meter supplied by Agilent Technologies of Santa Clara, Calif. In the plot 510 shown in FIG. 10, the measured values were fluctuated in the range of ±1 femtofarads (fF) and the average value at a given pressure was used. In particular, the plot 510 shows the average values of the measured data as the pressure was swept ten times. The base capacitance at atmospheric pressure was 1.167 fF. The capacitance increases nearly linearly with an average sensitivity of 0.75 fF/mmHg. Accordingly, coupling the pressure sensor 414 with a suitable ASIC can permit monitoring of IOP changes of less than 1 mmHg.

Figure 11:
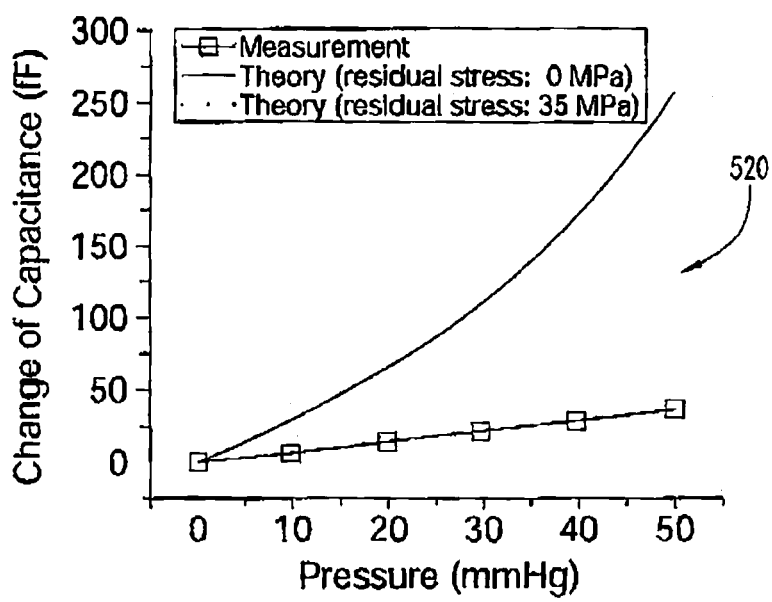
FIG. 11 is a plot of the change in capacitance of the pressure sensor of FIG. 7 as a function of pressure, as compared with two theoretical models for the same assuming a membrane residual stress of 0 MPa and 35 MPa.

As shown in FIG. 11, the actual measured sensitivity of the pressure sensor 414 is in reasonable agreement with the theoretical or analytical evaluations of the design—in particular, considering a residual stress of 35 MPa of the membrane, as calculated via Equation 1 above. FIG. 11 shows a plot 520 that compares the actual data used in the plot 510 with two theoretical models of the pressure sensor 414: one of which assumes that the membrane 442 has a residual stress of 0 MPa, whereas the other assumes that the membrane 442 has a residual stress of 35 MPa. The actual data closely tracks the theoretical model in which a residual stress of 35 MPa is assumed.

FIGS. 12A-12F depict another illustrative fabrication process that can be used to create a capacitive pressure sensor 614 (FIG. 12). Specific dimensions, materials, and other features are provided with respect to this illustrative process. While such specific dimensions, materials, and features may constitute independently patentable subject matter, it should be understood that other suitable dimensions, materials, and features may be used in fabricating other capacitive pressure sensors in accordance with other embodiments of the present disclosure, and thus such dimensions, materials, and features are not necessarily meant to be limiting.

The process in FIGS. 12A-12F utilizes direct parylene-to-parylene bonding. This approach can reduce the total thickness of the pressure sensor 614 and simplify fabrication, as compared with the pressure sensor 414 and the process of FIGS. 6A-6I. For example, the process of FIGS. 12A-12F eliminates the use of a multilayer structure that includes sacrificial PR which is released to form the dielectric region or gap between the capacitor plates. It also eliminates backside sealing of the substrate (e.g., applying Kapton to an LCP substrate), thereby reducing the overall thickness of the sensor 614. In certain embodiments, the dielectric gap can be encapsulated at a low temperature (e.g., about 230 degrees Celsius) by a membrane transfer technique using parylene-to-parylene bonding. This bonding process can be suitable for LCP substrates having a low melting temperature (e.g., about 315 degrees Celsius).

Figure 12A:
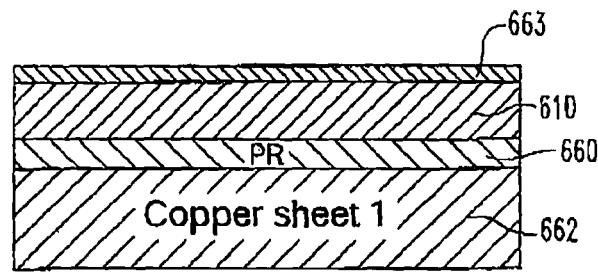
FIGS. 12A-12F are schematic views depicting various stages of another method for fabricating an embodiment of a pressure sensor.

With reference to FIG. 12A, a piece of LCP 610 is attached to a thick sheet of copper 662, which can serve as a temporary carrier, via a layer of photoresist 660. The LCP can be of any suitable thickness, such as those discussed above. In the illustrated embodiment, the LCP defines a thickness of about 25 microns. The copper sheet 662 can have any suitable thickness (e.g., about 635 microns in the illustrated embodiment), and may be obtained, for example, from K&S Engineering of Chicago, Ill. A mask layer 663 for reactive ion etching (RIE) can be deposited on the LCP layer 610. For example, the mask layer 663 can comprise a thin layer of Ti/Au, which may be deposited by sputtering. Any suitable thickness for the layer 610 is possible. In the illustrated embodiment, the layer 663 is about 60 nanometers thick.

Figure 12B:
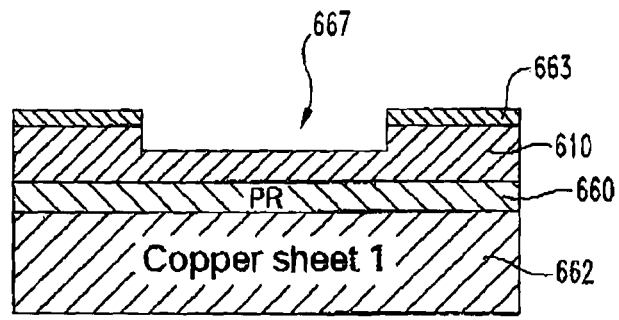

With reference to FIG. 12B, the mask layer 663 is patterned by a conventional lithography process, and a cavity 667 is thereafter created by an RIE process. A depth of the cavity 667 can be selected to ultimately achieve a desired size of a dielectric region or gap 648 (FIG. 12F). In the illustrated embodiment, the depth of the cavity 667 is about 2 microns.

Figure 12C:
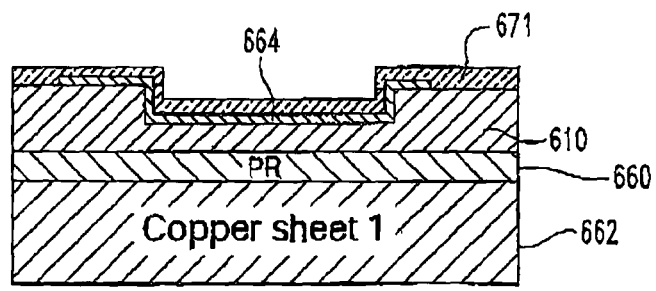

With reference to FIG. 12C, the mask layer 663 is etched out, and a layer 664 of Ti/Au is then deposited onto the LCP layer 610 and patterned. The layer 664 can define one or more of a lower electrode 646 and an electrical lead 622 (FIG. 12F). Any suitable thickness for the layer 664 is contemplated. In the illustrated embodiment, the thickness is about 0.5 microns. A thin layer of parylene 671 can then be coated as a bonding layer over the layer 664. In the illustrated embodiment, the parylene layer 671 defines a thickness of about 0.5 microns.

Figure 12D:
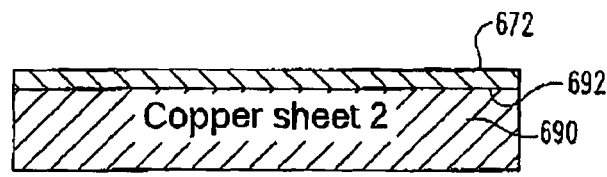

With reference to FIG. 12D, a sheet of copper 690 is coated with a detergent 692 (e.g., Micro-90®). Then, a parylene layer 672 is deposited on the metal sheet 690. The parylene layer 672 can have any suitable thickness, which may be selected based on the factors discussed above. In the illustrated embodiment, the thickness can be about 1.3 microns. The detergent 692 allows for easy detachment of the carrier sheet of copper 690 from the parylene layer 672 after the parylene layer 672 has been transferred in a bonding process, as discussed further below.

Figure 12E:
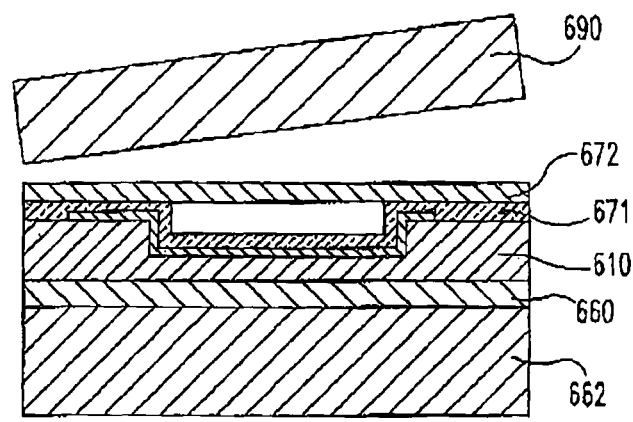
Figure 12F:
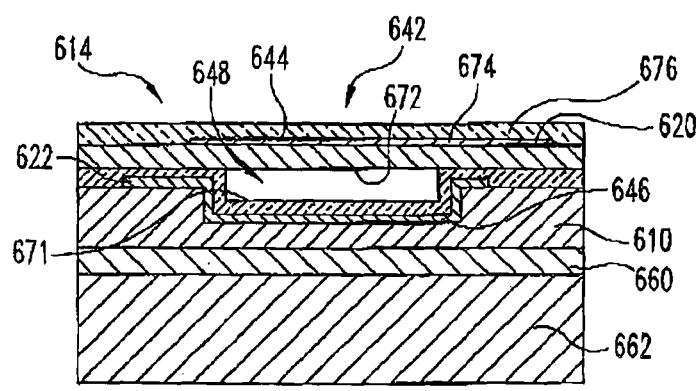

With reference to FIG. 12E, the two parylene layers 671, 672 are bonded to each other using a compression molding press (e.g., any suitable press available from Wabash MPI of Wabash, Ind.). Again, it shall be understood that the dielectric region 648 may be filled with any material (e.g., gas, liquid, solid, gel) which allows the upper or lower plates 444, 446 to move or flex relative to one another, thereby creating a change in capacitance of the sensor 414. In certain embodiments, the bonding may proceed at 230 degrees Celsius for 30 minutes under atmospheric pressure with an applied force of 0.3 ton (U.S.). After bonding, the sample is dipped into a copper etchant, such as ferric chloride. Due to undercut in the wet etching process, the copper sheet 690 is easily separated from the transferred parylene layer 672, even without etching the whole metal sheet 690.

With reference to FIG. 12F, another layer of Ti/Au 674 can be deposited on the parylene layer 672. The Ti/Au layer 674 can define one or more of an upper electrode 644 and an electrical lead 620. The Ti/Au layer 674 can define any suitable thickness (e.g., about 0.3 microns). An additional layer of parylene 676 can then be deposited over the Ti/Au layer 674 and the parylene layer 672. In the illustrated embodiment, the parylene layer 672 is about 1.3 microns thick. A composite membrane 642 portion of the pressure sensor 614 thus can include the Ti/Au layer 674 sandwiched between the parylene layers 672, 676. As previously discussed, the thicknesses of the various layers 672, 674, 676 can be selected to achieve the desired properties of the membrane 642, such as the residual stress thereof. The LCP layer 610 can then be detached from the copper sheet 662 by removing the PR layer 660 via PR stripper. For example, in some embodiments, at least a portion of the assembly is submerged in PR stripper for about 5 hours.

Figure 13:
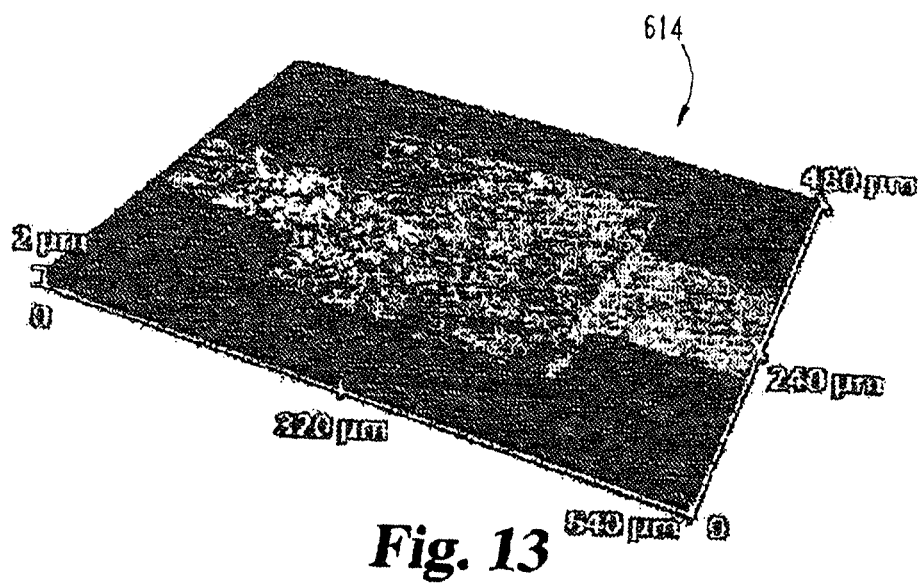
FIG. 13 is a 3-D image of an embodiment of a pressure sensor that has been fabricated using the method of FIGS. 12A-12F.
Figure 14:
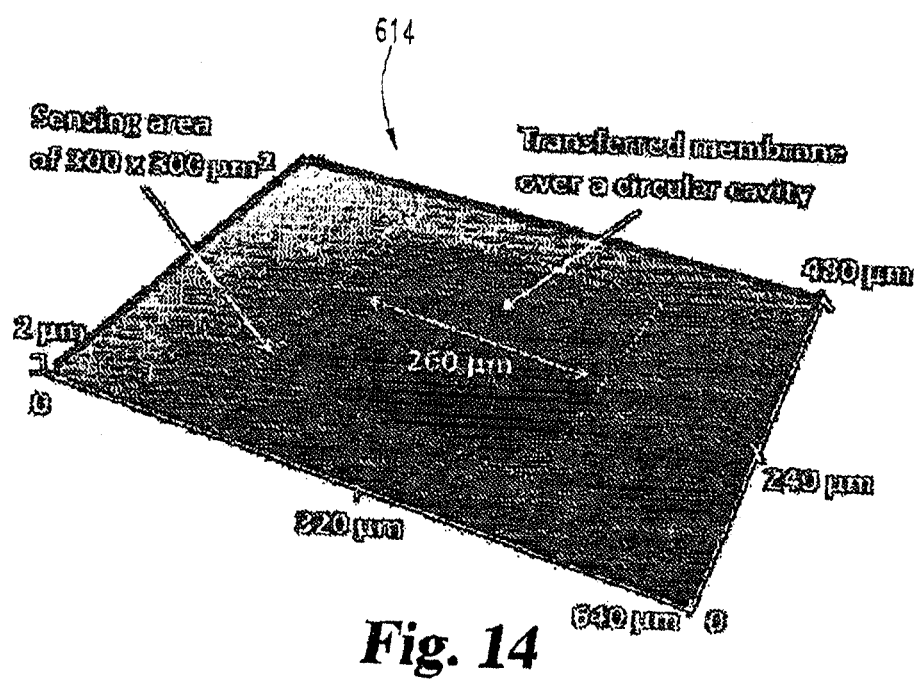
FIG. 14 is a surface profile of the pressure sensor of FIG. 13.

With reference to FIGS. 13 and 14, an illustrative embodiment of a pressure sensor 614 was formed using the process discussed with respect to FIGS. 12A-12F. The sensing area is about 300 microns×about 300 microns, and the thickness is about 30 microns. This thickness is an order of magnitude lower than conventional silicon-based capacitive pressure sensors. FIG. 13 shows a 3-D image of the pressure sensor 614, and FIG. 14 shows a surface profile measured by a confocal laser scanning microscope (LEXT from Olympus). The membrane is almost flat and is positioned over a circular cavity of about 260 microns in diameter. A surface roughness of the membrane is about 0.2 to about 0.3 microns.

Figure 15:
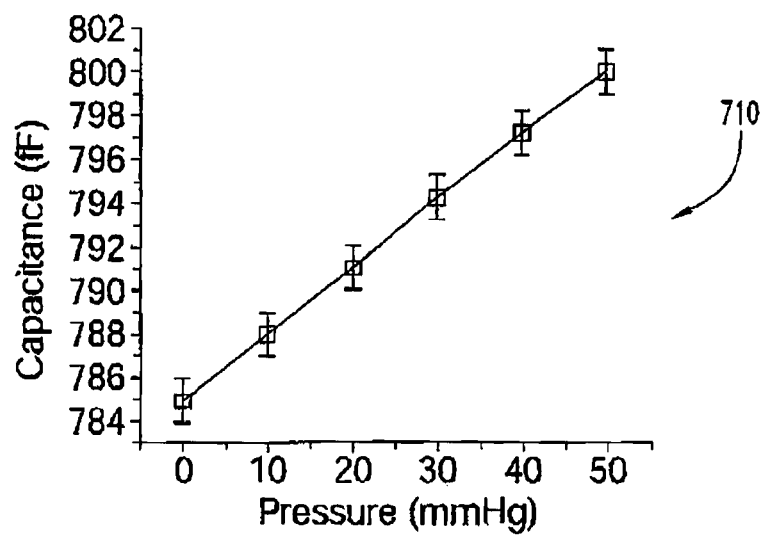
FIG. 15 is a plot of the capacitance of the pressure sensor of FIG. 13 as a function of pressure.

Using the same measurement setup discussed above with respect to FIGS. 9-11, the change of capacitance of the pressure sensor 614 was measured in the pressure range of 0 to 50 mmHg above atmospheric pressure using an LCR meter (Agilent 4284A) with the sensor 614 positioned inside the pressure chamber (MMR probe station). The pressure was swept ten times and the average value was recorded. FIG. 15 shows the measured response 710 of the sensor 614 to the change of pressure. The base capacitance is 784.92 fF, and it increases with a nearly linear average sensitivity of about 0.3 fF/mmHg.

Figure 16:
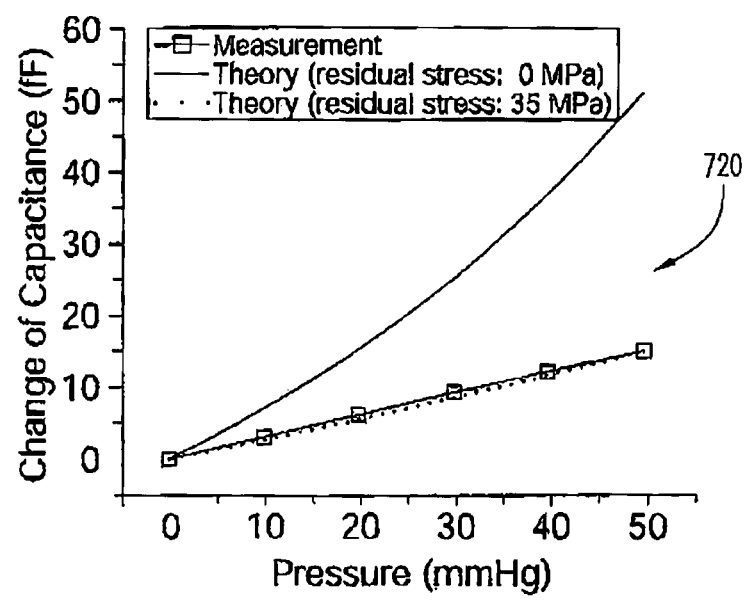
FIG. 16 is a plot of the change in capacitance of the pressure sensor of FIG. 13 as a function of pressure, as compared with two theoretical models for the same assuming a membrane residual stress of 0 MPa and 35 MPa.

As shown in FIG. 16 (plot 720), the increase in sensitivity corresponds with a theoretical design that assumes a residual stress of 35 MPa for the membrane 642. The sensitivity per unit area (milliimeter$^2$) is about 3.3 fF/mmHg, which is comparable to that of large-scale commercial sensor diaphragms, despite the much smaller area of the sensor 614. The sensor 614 can thus be well-suited for IOP sensing with a resolution less than 1 mmHg, such as when the sensor is combined with a suitable ASIC.

In various other embodiments, the capacitance of the sensor 614 can increase with a nearly linear sensitivity of no less than about 0.1, 0.2, 0.25, 0.3, 0.4, 0.5, 0.6, 0.7, 0.75, 0.8, 0.9, or 1.0 fF/mmHg. In other or further embodiments, the sensitivity per unit area (millimeter$^2$) is no less than about 1.0, 2.0, 2.5, 3.0, 3.3, 3.5, 4.0, or 5.0 fF/mmHg.

Figure 17:
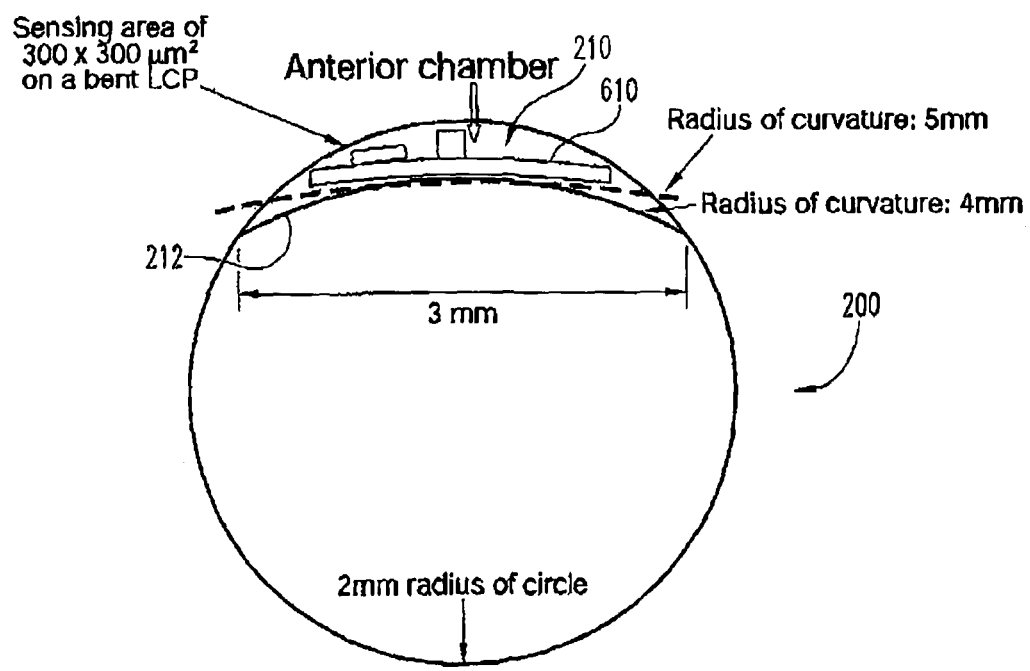
FIG. 17 is a schematic cross-sectional view of an embodiment of a pressure sensing system implanted within the anterior chamber of a mouse eyeball, which further illustrates a radius of curvature of a surface of the anterior chamber and a theorized radius of curvature of a liquid crystal polymer substrate positioned at that surface.

As previously mentioned, in certain embodiments of pressure-sensing systems (e.g., the systems 100, 300), the LCP substrate 610 on which an IC, an antenna, and a capacitive pressure sensor are integrated or otherwise coupled may bend so as to be accommodated within the limited space of the anterior chamber in the mouse eye 200. Based on the dimensions of a mouse eye 200 represented in FIG. 3, the radius of curvature on the posterior surface 212 of the anterior chamber 210 can be calculated as about 4 millimeters. Such a small radius of curvature can be more challenging for pressure sensors, as compared with human eyes or even other animal models. For example, the radius of curvature can be smaller for smaller eyes. With a smaller radius of curvature, the bending of the substrate can be more pronounced, such that it might have a greater effect on operation of the pressure sensor. In particular, the lower electrode 646 of the pressure sensor 614 may sufficiently thin and/or malleable so as to bend in conformity with the substrate 610. Such bending could interfere with pressure measurements; for example, if the sensing area of pressure sensor 614 is large, while the separation distance between the capacitor's electrodes is small, the curvature of the lower electrode 646 could bring it into close proximity or even contact with the upper electrode 644, in some instances. Curvature of the substrate 610 can also induce stress (residual stress) therein. It could also yield greater residual stress in the membrane 642. It can be estimated that a pressure-sensing system, which may also be referred to as an LCP tag, that is implanted inside the anterior chamber 210 of a mouse eye has a radius of curvature greater than 4 millimeters, as indicated in FIG. 17.

Figure 18:
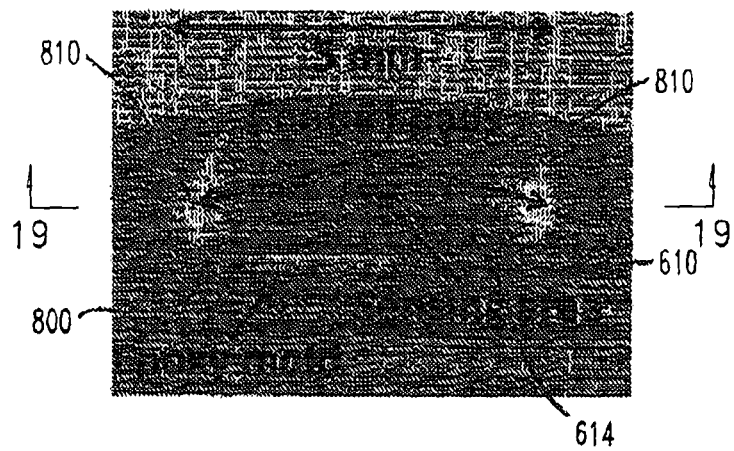
FIG. 18 is a perspective view of a pressure sensor having a flexible substrate that is coupled to a mold having a curved surface, wherein the substrate is curved to conform to the curved surface.
Figure 19:
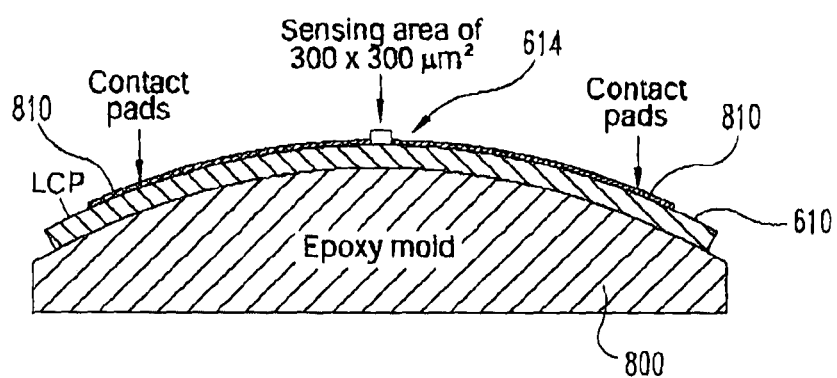
FIG. 19 is a schematic cross-sectional view of the setup of FIG. 18 taken along the view line 19-19.

With reference to FIGS. 18 and 19, in order to mimic the curved surface of an LCP tag that is bent when implanted, for purposes of testing, an epoxy mold 800 having a radius of curvature of about 5 millimeters is created. A pressure sensor 614 may be attached to the mold 800. The pressure sensor 614 can be integrated into a substrate 610 having an extended area to facilitate testing of the pressure sensor 614. Moreover, the pressure sensor 614 can be electrically coupled with enlarged and extended contact pads 810 to facilitate the testing. The assembled test sample is measured in a manner such as described above, such as by using the MMR probe station and the Agilent 4284A LCR meter.

Figure 20:
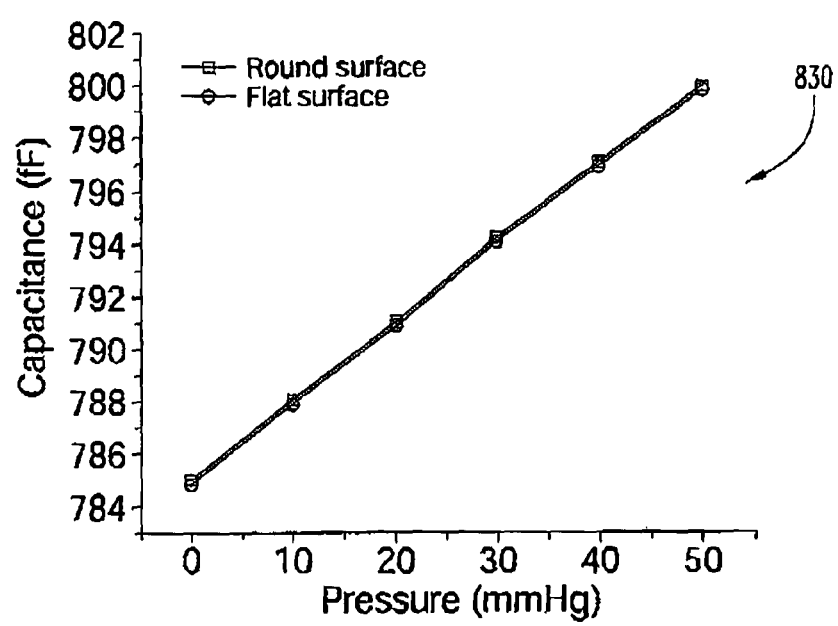
FIG. 20 is a plot comparing the performance of a pressure sensor when its substrate is flat with its performance when positioned in a curved setup such as that of FIGS. 18 and 19.

FIG. 20 depicts a plot 830 that includes data obtained from a pressure sensor 614 that is operated with its substrate in a flat configuration, as compared with data obtained when the substrate is curved due to the pressure sensor 614 being attached to a curved-surface setup such as that in FIGS. 19 and 20. The base capacitance and sensitivity on the curved surface correspond with those on the flat surface. This result shows that the estimated curvature of the implanted LCP substrate does not significantly affect performance of the capacitive pressure sensor having a sensing area of about 300×about 300 microns$^2$. The pressure-sensing system is flexible, but the small size sensor is not affected by this curvature and the resulting induced stress. A larger area sensor, while being more sensitive, would have difficulty with the bending radius as the two capacitive plates could touch.

FIGS. 21A and 21B depict a further embodiment of a pressure-sensing implant, or pressure-sensing system 900 that is configured to be implanted in the eye of an animal. The pressure-sensing system 900 is similar in function to system 100 described above and suitable for implantation in the eye of a mouse, but with the addition of a light emitting diode (LED) to provide a visual indication that power is being transferred, or the level of power transfer, between the external radiation source and the system 100. In the illustrated embodiment, the pressure-sensing system 900 includes an integrated circuit (IC) 912, a MEMS pressure sensor 914, and an antenna 916, and an LED 917 that are mounted to or integrally formed with a substrate or tag 910. In certain embodiments, the LED output light intensity increases as the power being received by the system 100 increases, thereby providing visual verification that the system 100 is operational. In other embodiments, the LED can be used as a communication medium, for example, by flashing between on and off states to convey a digital code or pattern in which data is encoded.

The integrated circuit 912 can be electrically coupled with each of the pressure sensor 914 and the antenna 916 so as to be able to electrically communicate therewith. In particular, separate portions of the pressure sensor 914 can be coupled with the integrated circuit 912 via a pair of electrical leads 920, 922, as discussed further below. The pressure sensor 914 can be configured to provide data (e.g., capacitance values) to the integrated circuit 912, which can be configured to store the data, derive information from the data (e.g., derive calculated or estimated pressure values from the capacitance values), and/or deliver the data and/or the derived information to the antenna 916 for delivery to a remote data storage and/or analysis system. The integrated circuit 912 may interface with the antenna 916, which in one embodiment can be an inductive loop antenna, in a similar fashion is described above with respect to integrated circuit 112 and antenna 116 of system 100. In the embodiment of FIG. 21A-B, the antenna 916 may be a self-expandable Nitinol loop antenna. The Nitinol provides a balance between antenna radiation efficiency and surgical feasibility. The pressure sensor 914 and metal traces for interconnection between components are embedded in an ultra-thin form factor. Also in this embodiment, a double-sided copper (Cu) cladding 25 μm LCP (ULTRARAM 3850, available from Rogers Corporation) is utilized as a carrier substrate, which makes the via etching process faster compared to a thick silicon carrier substrate.

FIGS. 22A-F depict another embodiment of a capacitive illustrative fabrication process that can be used to create the capacitive pressure sensor 914. As shown in FIG. 22A, the back side Cu layer 905 of an LCP carrier 962 is patterned for the etch mask of the reactive ion etching (RIE) process, and then the openings 984 through the carrier 962 are created by oxygen plasma etching during RIE.

With reference to FIG. 22B, the top side Cu layer 907 of the carrier 962 is coated with 10 μm thick photoresist 909 to smooth the roughness of the Cu layer 907 on the carrier 962 and to allow for later release of the fabricated tag from the carrier LCP substrate 962. Then, a parylene substrate 911 of 10 μm is deposited on the photoresist 909 and a Ti/Au (2 μm) layer 964 is sputtered and patterned, thereby creating metal pads 965 for mounting the diode 917 and antenna 916, and lower sensor electrode 946.

With reference to FIG. 22C, to create the cavity 948 of the pressure sensor 914, a 4 μm sacrificial photoresist layer 970 is spun on the lower electrode 946 and covered with a 1 μm thick parylene layer 972. The metal pads 965 are then exposed by etching the parylene layer 972.

With reference to FIG. 22D, a thin Ti/Au layer of 0.1 μm thickness is deposited and patterned to create the top electrode 944 of the pressure sensor 914.

With reference to FIG. 22E, before the Cu etching process, photoresist 967 is coated to protect the top metal electrode 944 from the Cu etchant.

With reference to FIG. 22F, the Cu near the openings 984 and on the bottom of carrier 962 is then etched out, and a RIE process is performed to create the holes for releasing the photoresist 909, 967, 970 and etch out the outline of the tag 910.

With reference to FIG. 22G, the tag 910 is submerged into acetone to release the photoresist 970 and create the cavity 948 of the pressure sensor 914. the cavity 948 is sealed with Kapton tape of 25 μm thickness as shown.

With respect to FIG. 22H, a parylene layer 976 of 3 μm thickness is coated for passivation so that the tag is compatible with the mouse eye environment. The final diameter of the antenna is 2.2 mm and the area of the tag is 1.65×0.8 mm$^2$. The thickness of the thickest part of the tag is less than 100 μm. The functional tag and its implantation inside the mouse eye are shown in FIG. 23.

In certain embodiments, to accurately determine the IOP, several conversions occur to receive the data externally. These include conversion from pressure to an electrical equivalent, digitization of the electrical equivalent, and finally transmission of that digital equivalent. In one embodiment discussed herein, a pressure to capacitance conversion is used to monitor pressure and to determine the accuracy of the IOP monitoring system.

According to one embodiment, digitization of the capacitive data generated by the pressure sensor 914 is completed through frequency modulation (FM). The measurement system uses a clock source that is dependent on the capacitor (initially a varactor) and second the pressure sensor. Initially using a varactor, FIG. 71 depicts how the frequency output changes dramatically over large pF changes. The output is nonlinear and the base capacitance of the sensor determines the output frequency as well as the resolution necessary to determine change in capacitance. The lower the base capacitance the larger the frequency changes for given capacitance change. From data collected, a logarithmic curve was fit to the data to determine the frequency based on capacitive input.

$$\text{Freq(kHz)}=-186.3 \ln(\text{Cap(pF)})+726.46, R^2=0.981 \quad \text{Equation 8.19}$$

This allows the conversion from capacitance to FM to have a higher accuracy than a base capacitor using 10 pF.

Using a ring oscillator design, the FM modulated output signal rides on the transmitted wave where it can then be demodulated and interpreted. Using the description in the materials and methods, a FFT of the output signal was taken from the pickup antenna. FIG. 72 depicts the same output data obtained in FIG. 71. The same nonlinear logarithmic curve is obtained for the transmitted data, as what was created by the measurement circuit.

From data described in Table 8.5 it is shown that there is no percent difference of greater than 1% for the output data. Therefore there is an accurate transmission of capacitive measurements transferred from the measurement circuit to an external antenna, and that there is little or no loss of information when transferred.

TABLE 8.5

Comparison of FM output for measurement circuit and transmitter

| Capacitance (pF) | Measurement Output (kHz) | Tx Output (kHz) | % Difference |
|---|---|---|---|
| 0.5 | 1380. | 1369. | 0.7859% ± 0.65% |
| 1 | 1178. | 1184. | −0.4798% ± 1.24% |
| 5 | 523.0 | 577.8 | −0.9242% ± 0.93% |
| 10 | 324.7 | 323.9 | 0.2612% ± 2.15% |
| 15 | 230.8 | 229.4 | 0.6198% ± 1.59% |
| 22 | 171.4 | 170.5 | 0.4967% ± 1.80% |

Knowing that the base capacitance of the pressure sensor 914 is approximately 1 pF, data suggests outputs around 1 MHz during the changing of pressure. FIG. 73 depicts this data, and shows that the measurement system is functional in determining frequency based on an input pressure. Even though the capacitive change of the sensor is small ~0.5 fF per mmHg, the high frequency output of the measurement system allows for a correlation of the Table 8.5

As the pressure increases from this system, it is noticed that the frequency changes negatively at a rate of 426 Hz per mmHg. Various embodiments of the present disclosure having this resolution provide adequate correlation between frequency. The limit is put on the external base station, where there are no space and design constraints. To obtain the resolution of 0.5 mmHg, the basestation should have a resolution of 213 Hz. As the sensor increases in sensitivity, the output will have a greater frequency change, making it easier on the design of the external basestation.

Figure 47:
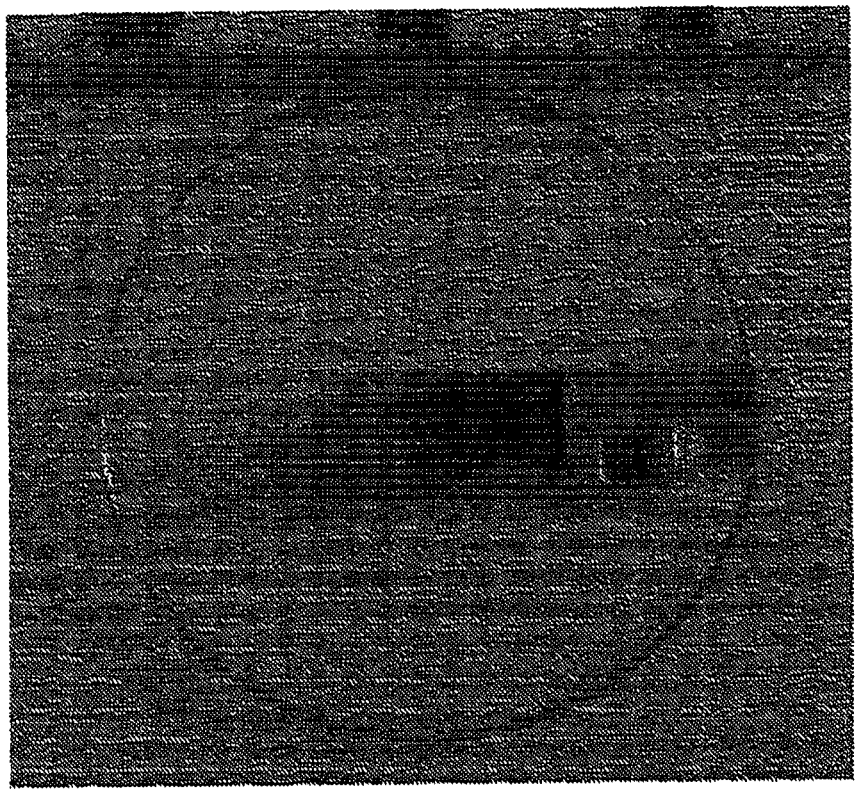
FIG. 47 shows a mouse-sized IOP device with surface mounted passive components according to one embodiment.
Figure 48:
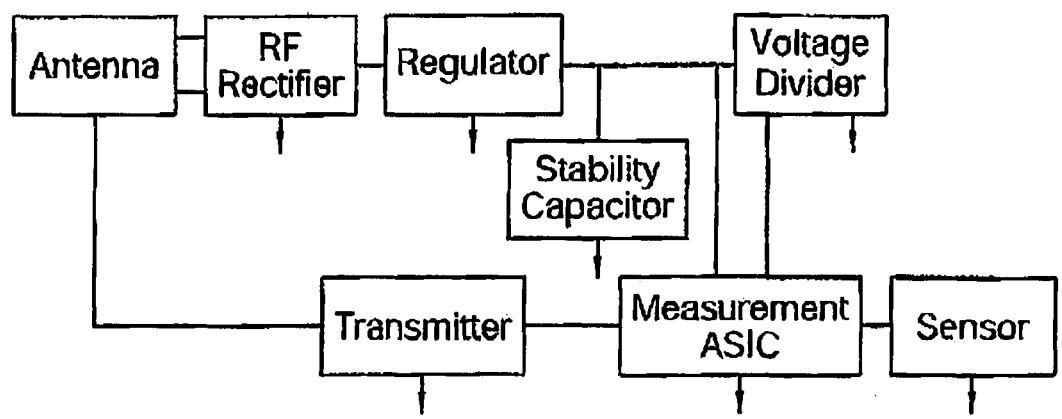
FIG. 48 is a block diagram of a full system device according to one embodiment.

The device used (FIG. 47), was developed for the need to monitor IOP in genetically modified mice. This will assist researchers in determining the effects genes have on glaucoma and IOP changes. The device includes a 25 μm parylene substrate of dimensions 1.7 mm by 0.8 mm. In one embodiment, in this substrate, gold traces are created that connect an RF powering ASIC, a tuning shunt capacitor, and a red LED. The antenna, a 2.5 mm 2.5 mm nitinol loop may be gold coated and attached at the head of the substrate. In one embodiment, the RF powering ASIC is similar to those disclosed by Chow, et. al. in "A Miniature Implantable RF-Wireless Active Glaucoma Intraocular Pressure Monitor," Institute of Electronics and Electrical Engineers Transactions on Biomedical Circuits and Systems, Vol. 4, No. 6, December 2010, pp. 340-349, the entire contents of which is hereby incorporated by reference in its entirety.

After the initial anesthesia has taken effect, the animal was mounted in a stereotaxic frame. A mouse-specific nose cone was used to maintain an anesthetic plane within the stereotaxic frame. Throughout the procedure, sterile saline was applied to the operated eye at regular intervals to avoid drying. After checking for adequate anesthesia (e.g., toe pinch and observation of vitals via the pulse oximeter), a trochanter was used to puncture the eye at about 3-5 mm from the corneal limbus and implant the intraocular pressure monitoring device into the anterior chamber. The device is roughly 300 microns cubed. The trochanter was removed and the insertion site was sealed using a thin layer of adhesive (Dermabond Topical Adhesive). Once the adhesive has dried, recordings were taken.

A secondary insertion technique is also viable. The eye was washed with sterile PBS. A stab incision of no more than 1 mm was made at about 3-5 mm from the corneal limbus using a 3 mm microsurgical blade, or similar device. A volume of Viscoat Intraocular Viscoelastic Injection (or other commercially available alternative) was used to form the anterior chamber to allow for better manipulation of the sensor, while minimizing trauma to the eye. (Viscoat Intraocular Viscoelastic Injection, or similar solution, is sterile, non-pyrogenic, transparent viscoelastic preparations of a highly purified, noninflammatory, high molecular weight sodium hyaluronate or similar substances. These substances are routinely used in anterior segment ophthalmic surgical procedures in humans. It coats the iris, posterior corneal surface and anterior lens capsule, which helps protect these tissues from injury during the surgical procedure.) The intraocular pressure monitoring sensor was inserted through the incision, the intraocular viscoelastic injection syringe removed, and the incision sutured closed. Finally, a topical antibiotic, Vetropolycin, was applied to decrease inflammation for the remainder of the surgery.

Figure 50:
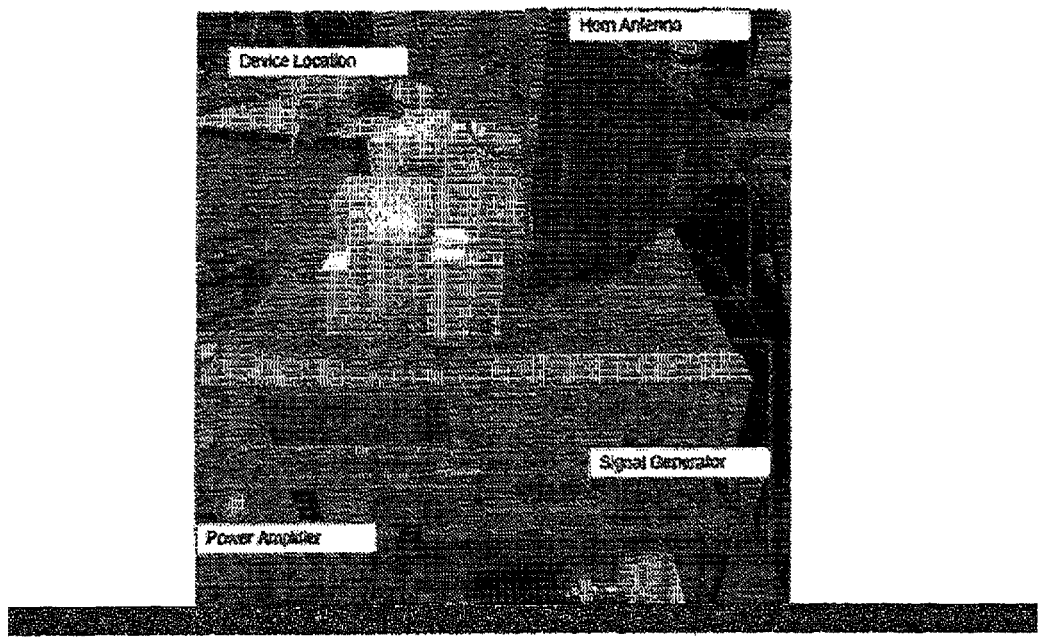
FIG. 50 shows a radio frequency powering setup to test devices in-vivo and ex-vivo according to one embodiment.
Figure 51:
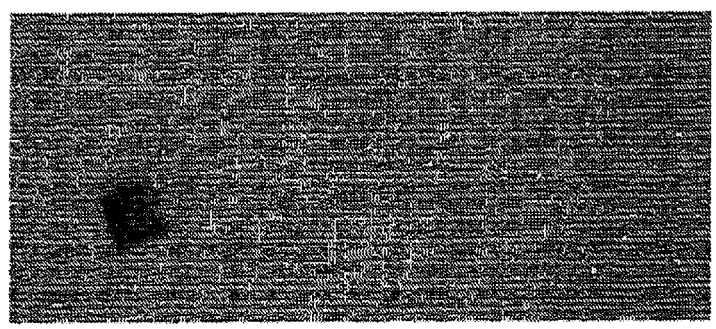
FIG. 51 shows a tadpole device based on a human IOP design.
Figure 52:
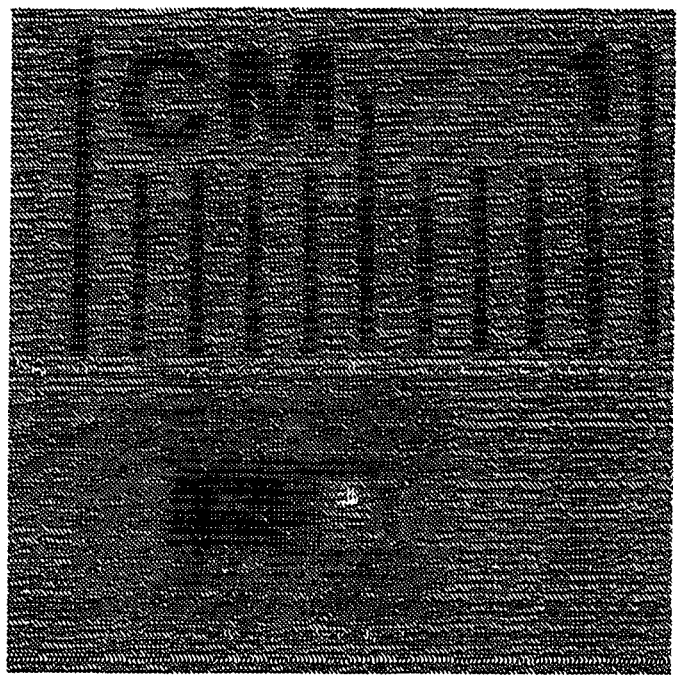
FIG. 52 shows a large LED ring device of FR-4 according to one embodiment.
Figure 53:
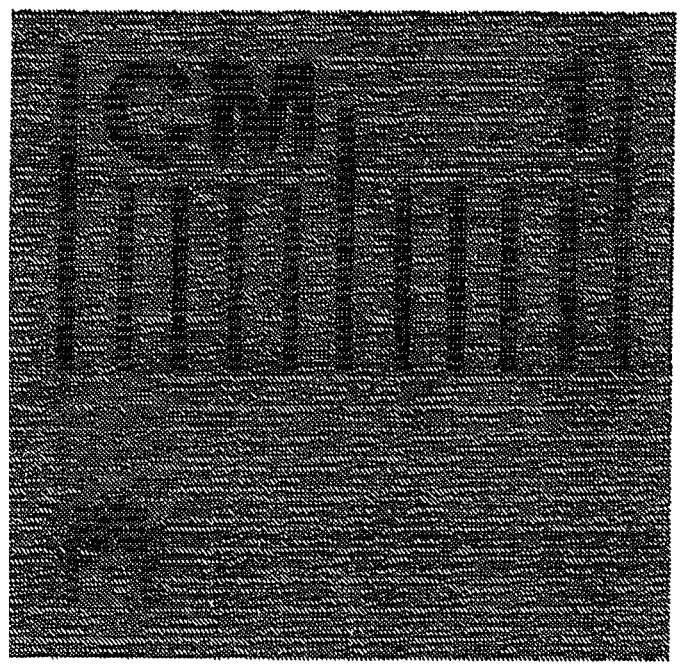
FIG. 53 shows a small LED ring device of FR-4 according to one embodiment.
Figure 54:
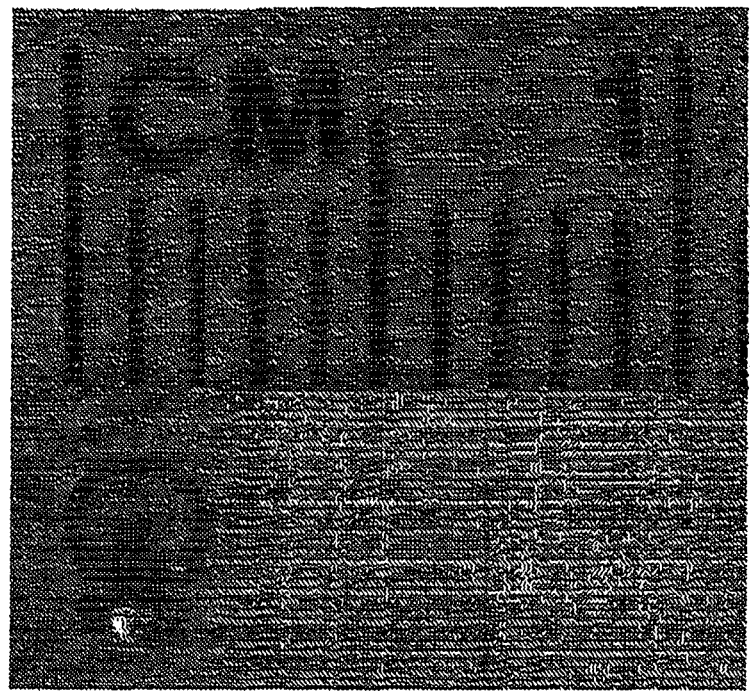
FIG. 54 shows a further optimization onto LCP of an LED device according to one embodiment.

The powering measurement setup (FIG. 50) was set to remove many factors including device location, monitoring offset, etc., and have only two functional factors for testing; these are frequency and power. In order to power the LED device an Agilent N5182A MXG Vector Signal Generator was used to create the initial signal. The signal was passed through an OPHIR 5161 RF power amplifier, and sent to a Dorado AN-GH1-12S horn antenna. To collect data, video recordings were taken in a black room to record the intensity of red light emitted from the diode. A camera was set at a specific distance from the LED device.

Powering levels from −15 to 3 dbm (25-43 dbm at horn antenna) output from the signal generator and frequency ranges from 1-2 Ghz were tested. A Labview code was developed in order to randomly choose a frame form the video that corresponds to each frequency and power. These pictures were then imported into Matlab for further analysis.

Given a specific input voltage, the LEDs have a corresponding current power relationship given by the manufacturer. This gives a conversion of LED intensity area to power input. Second, the device is tested ex-vivo. These devices were tested using the described power and frequency levels, but were tested in air at specific distances from the horn antenna and camera. Finally, the devices were implanted into mice eyes. This determined light intensity created by the same powering schemes as described ex-vivo. The animals were tested weekly after implantation to understand the effects the animal, inflammation, and time have on the power efficiency received by the LED device.

Mouse eyes were collected by first excising some of the surrounding skin and muscle using fine scissors and hemostats. A small, blunt spatula was then carefully inserted lateral to the eye against the zygomatic bone to the back of the eye. Moving the spatula against the bone, at least partly around the eye and eventually to the back wall of the orbital, was then performed to sever muscle and nerve connections. Eyes were then stored in HBHS in Eppendorf tubes at 4° C.

For histological imaging, eyes were secured in 1% agarose in PBS on a coverglass-bottomed dish. Laser scanning confocal microscopy was performed using on a Zeiss LSM10 using a translating microscope stage. DiI or DiD fluorescences in vasculature were imaged using the 543 nm or 633 nm laser lines, respectively. Reflectance of 633 nm light from the implanted device and the tissue surface was also collected, to capture the device location relative to vasculature.

The size of the mouse anterior chamber has less than 300 urn of workable thickness while the total diameter of the eye is approximately 2.5 mm. Therefore a device with a maximum diameter of about 2 mm and a thickness of about 300 μm is used in some embodiments of the present invention. Initial work using the FR-4 and LCP designs worked towards miniaturization of an implantable device (FIGS. 51-54). FIGS. 51-54 show the form factor change and miniaturization to get a LCP LED device created within size constraints.

Figure 55:
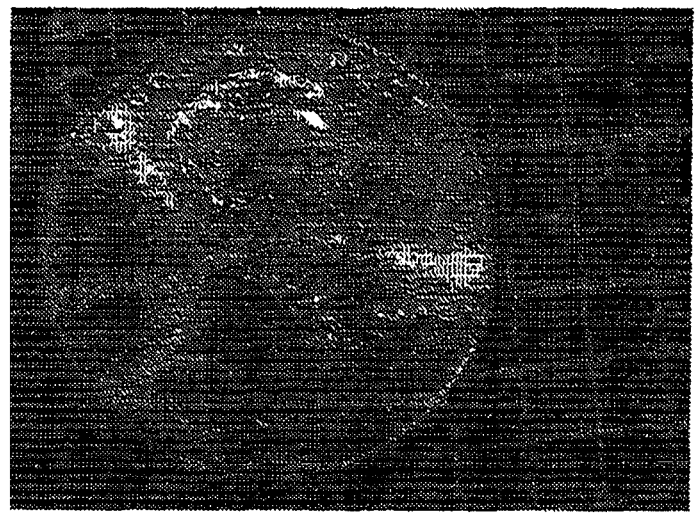
FIG. 55 shows an LED device wirelessly powered according to one embodiment.
Figure 57:
FIG. 57 shows an IOP device above antenna according to one embodiment.
Figure 58:
FIG. 58 shows a dummy sample being compressed for implantation according to one embodiment.

Various embodiments of the present disclosure perform well in ex-vivo, and yet other embodiments of the present invention pertain to use in the optic electrode design for neural stimulation. Initially, FIGS. 56-58, it was conceived that the devices could be created on LCP and sealed however, due to constraints of less than a 800 μm incision for the eye, adaptations were made to the overall design. various embodiments of the present invention use nitinol or other biocompatible shape-memory materials as the antenna for the mouse IOP device. Using the memory alloy properties of nitinol various embodiments contemplate a pre-implanted shape that is able to squeeze the implant through a specially made inserter, or by hand, through the incision and allow it to come to full size once inside the eye (FIG. 58). Using this initial design concept of a nitinol loop antenna, an LED device was created. It is understood that the LED device is utilized to prove the functioning of the device after it has been implanted (FIG. 55).

Figure 56:
FIG. 56 shows a device size comparison to an "O" of a penny according to one embodiment.

In order to properly test the system in a mouse, full system devices needed to be created that fit inside the limits of mouse eye anatomy. One embodiment of the present invention includes a 300 μm full system device to accomplish this goal. This ASIC is composed of four pads, two for the RF powering and two for the MEMS capacitor. This full system will then connect to the substrate and tested for full system functionality (FIG. 56). This system again does not have the sensor attached, but power capabilities are demonstrated Analysis of the LED on the implantable device (e.g., system 900) is helpful in determining the power transfer between the 2.5 mm loop antenna and an external source. Using the current voltage relationship dictated by the LED manufacturer allows for a power conversion based on input voltage. This input voltage then relates to the area displayed by the LEDs intensity.

Table 8.3.1, shows how current and power consumed by the LED device relates to input voltage for a particular LED supplied by CREE, Inc. of Durham, N.C.

TABLE 8.3.1

CREE LED voltage current relationship

| Voltage (V) | Current (mA) | Power (mW) |
|---|---|---|
| 1.625 | 1 | 1.625 |
| 1.7 | 3 | 5.1 |
| 1.8 | 8.5 | 15.3 |
| 1.9 | 17.5 | 33.25 |

Plotting this data, a curve fit equation can be used to relate voltage and current. This leads to an understanding of power consumed by the LED during powering using the relationship for power. For a given input voltage the LED lights up to a specific intensity. The LED intensity can therefore be monitored to determine the power being received by the system. In a dark room, a camera positioned a specific distance away from the LED device captures the LEDs intensity. By collecting this data, LED output intensity can be related to power consumed by the LED. Once the power being consumed by the LED is known, the power being consumed by other components within the system 100 can be determined based on the known electrical relationships between the other components and the LED. Thereafter, the relationship can be used to determine power being received and/or consumed by the system after implantation.

Each device, although designed for the same specifications, has a different resonant frequency that makes it efficient. This is useful in RF powering. In certain embodiments, there is little to no room for matching networks on the implanted chip. In one example embodiment of a pressure sensor system similar to system 900, the device tested was functional in the 1-2 GHz range (FIGS. 60 and 61) to determine the frequencies which provide the most efficient power transfer. Another tested device was found to be functional at around 3.0 GHz (FIGS. 62 and 63).

FIGS. 61 and 63 show a power consumption of 2 mA and 1.5 mA for the first and second tested devices respectively. Using this data a relationship of power input (power at the antenna) and the power consumed by the device is observed. In one example test, with approximately 8 watts of power being transmitted to the implanted device from the external receiver, at the peak frequencies the LED is consuming an amount of power which correlates to a consumption of 1.5 mW.

Figure 59:
FIG. 59 shows a mouse animal model implanted with an LED device according to one embodiment.

The devices tested have shown proper functionality after implantation. In terms of proper functionality and power consumption, one device was able to light up at the same distance from the external power transmitter as the ex-vivo testing. FIG. 59 depicts a mouse with the implanted LED device. In the visible eye the implant can be seen. FIGS. 64 and 65 show a relation of the power consumed by the LED and power input at a date 1 month after implantation.

During testing of the above devices, differences in the in-vivo and ex-vivo results were observed. First, the power consumed given the same input power decreased, and the frequency at which the LED is powered jumped. Upon analysis of power consumed, at its peak, the ex-vivo device displayed a power consumed 2.00 mA ex-vivo at 1.6 GHz while in-vivo had a 1.01 mA power consumed at 1.8 GHz.

This power decrease is expected under the open condition (air), and implanted condition (anterior chamber of mouse eye). One reason is that the boundary conditions set up by the anatomy of the mouse; cornea, aqueous humor, and skeletal structure causes reflections of the energy at each boundary. Finally, as the remaining energy reaches the implanted device, a decrease in power consumed is observed for the LED device, and therefore a 50% difference in power consumption between ex-vivo and in-vivo analysis.

The second observation is with the resonant frequency where the LED consumes the most energy. For the first animal (FIGS. 60 and 61) and implanted data (FIGS. 64 and 65) there is a jump of 200 MHz. This is observed because the antenna for RF coupling is not directly matched to any given frequency. Its original harmonic includes the antenna itself setting its resonant frequency at approximately 1.6 GHz. When the device is implanted inside the animal, the medium around that antenna will change that resonant frequency based on its electrical characteristics.

Two other animals beside the one described also were able to pick up rough LED data, not using the LED intensity capture method, but by placing the mouse inside a horn antenna used to receive the signal output by the implanted device. Gathering these measurements consisted of changing the frequency and power while recording the frequency which permitted the largest LED intensity by visual inspection. Table 8.3.2 depicts the data received. With regards to device 3, following the same scheme as the previous 2 devices in Table 8.3.2, an increase in frequency is expected. However, this was not the case. Devices 1 and 2 were of the same initial batch of fabricated antennas, therefore they had a similar RF powering scheme. The third device was of a different run, and due to the connections had a different characteristic resonant frequency, at approximately 3.1 GHz. Following implantation of the animal, data collected at the first and second weeks has shown the frequency has moved, not up as in the first set of devices, but down to the approximate 1.8 GHz data point observed in the first and second mice.

TABLE 8.3.2

Resonant frequency to obtain brightest LED intensity

|  | Mouse 1 | Mouse 2 | Mouse 3 |
|---|---|---|---|
| Ex-Vivo Functioning Freq | 1.6 GHz | 1.38 GHz | 3.1 GHz |
| In-Vivo Functioning Freq | ~1.8 GHz | ~1.8 GHz | ~1.8 GHz |

This shows that the medium in which a passive device is implanted has an effect on its output LED response. This is helpful in showing that different animal models and different anatomical locations exert different natural frequencies (i.e. anterior chamber of eye, surface of skin above skull, and inside artery). Following implantation times of one, two, and four weeks, histology was conducted on the eyes of the implanted animal, discussed below in Example 3.

Figure 35:
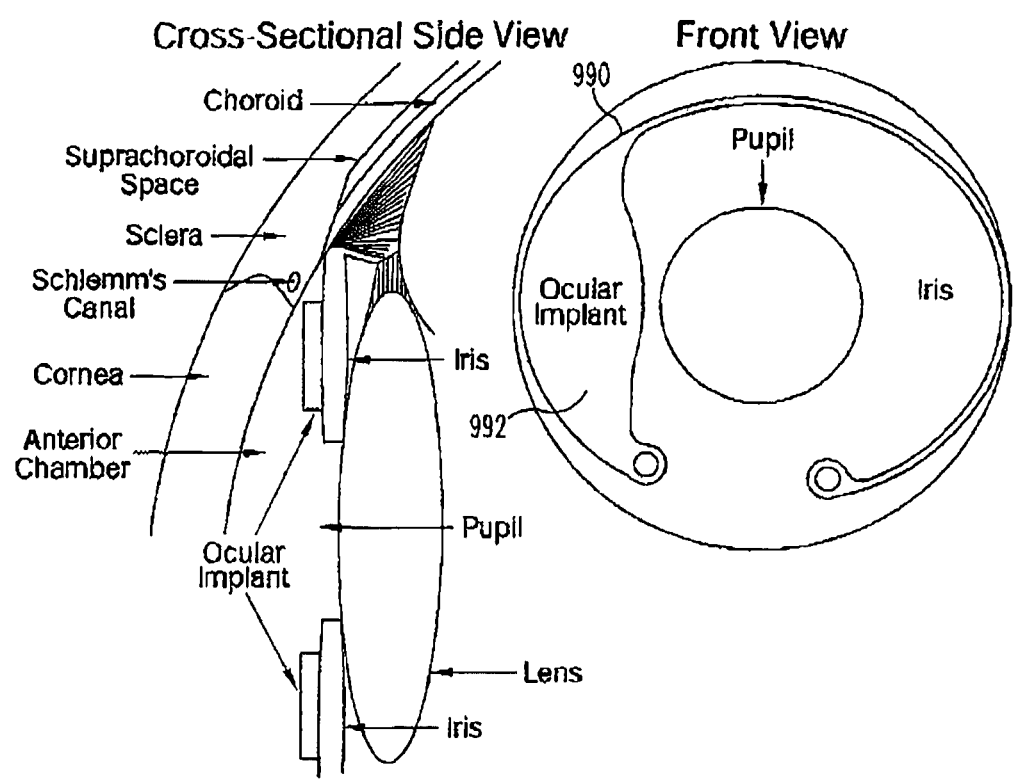
FIG. 35 shows a LCP design for implantable IOP device according to one embodiment.
Figure 36:
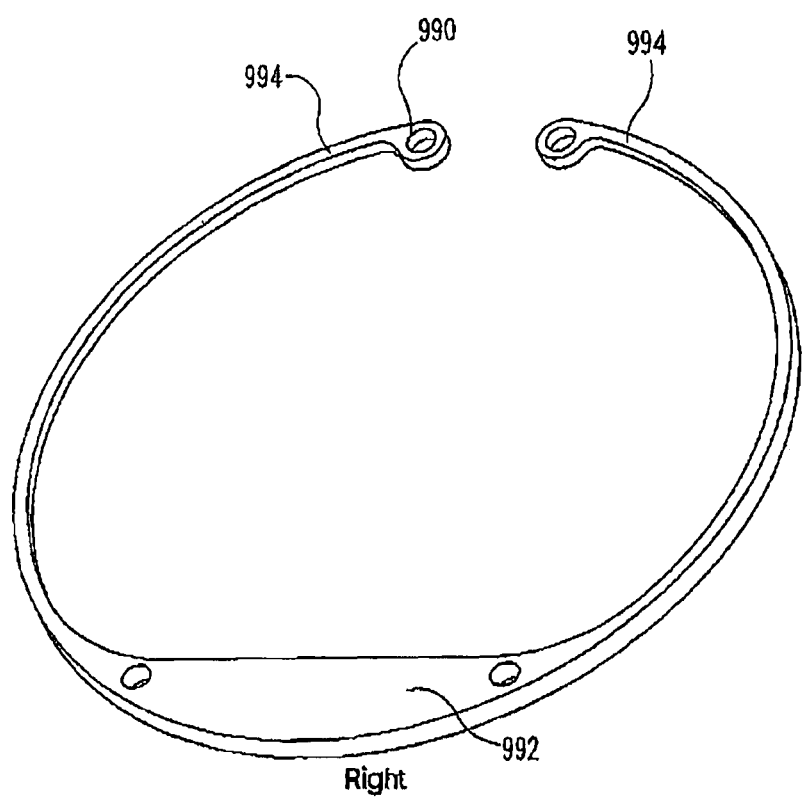
FIG. 36 is a perspective view of a capsular tension ring IOP device design according to one embodiment.

Referring to FIGS. 36 and 43, various embodiments of the present invention comprise a capsular tension ring (CTR) form 990. As shown, the capsular tension ring 990 has a base portion 992 for housing the sensor and related electronics and two curved arms 994 extending from the base portion 992. This device will already have curvature built into the mechanical integrity of the device, and allows the device to maintain the position of the sensor within the eye. FIG. 43 shows such a device after implantation in an animal eye. FIG. 35 shows a further embodiment, where the base portion 992 is offset, leaving a single curved arm 994 extending from the base portion. In certain embodiments, nitinol makes up the dipole antenna arms 994 of the CTR design.

Various embodiments of the present invention include a base station 1000 for powering of the pressure sensor circuitry, and also for receiving data from the pressure sensor (referring to FIG. 37). This base station should have universal functionality so that it has the ability to work with any testing facility and researcher or doctor. The two initial base station designs were for functionality of glaucoma for both the human IOP and mouse devices. The mouse base station was made to fit under the shelving where mice would be held so that it would not interfere with everyday activities. For the human device it was determined that the ophthalmologists want the antenna part of the device close to the patient, but the equipment to run the system farther away from the patient and near the computer and equipment that they use.

The systems described above have gone through functionality testing. From the work described previously along with silicon 6 mm by 3 mm devices compared implantable powering of the LTCC loop and SI loop at specific distances and differing RF powers. Upon implantation into the rabbit anterior chamber RF power received was compared between LTCC and SI devices (FIG. 46). What this shows is when the systems increased in distance from its radiating source that more power was needed to attribute the same current consumption by the chips. This demonstrates that RF powering had functionality for wirelessly powering devices. Also, the method of capturing the LED intensity and/or power consumption for a given device can help improve the understanding of the energy being coupled to a device while removing the wires that are normally used to analyze energy transfer.

In certain embodiments, the circuitry within the pressure sensing system 100, 900 is configured to provide for signal processing of the capacitance signal. In one embodiment, the pressure sensor interfaces with circuitry that provides the sensor signal at a higher order harmonic, such as the $3^{rd}$ order harmonic, of the radiowave frequency that was utilized to power the sensor. In still further embodiments, the circuitry includes a low-power, 10 bit analog to digital converter that provides a high resolution signal of the changes in capacitance. High isolation between the fundamental and harmonic tone and higher antenna efficiency at the harmonic frequency can therefore be achieved. Furthermore, due to the high isolation, detecting a low power harmonic signal in the presence of a relatively high power transmitted tone results in alleviation of the dynamic range constraint of the receiver.

Moreover, as the $3^{rd}$ order scheme enables three times more frequency shift per unit capacitance change than using the fundamental tone, higher resolution measurement of a pressure change can be accomplished. Also, compared with the traditional inductive coupling method, harmonic detection provides further sensing distance since the coil is utilized as an antenna rather than an inductor.

In some embodiments, the inductive Nitinol loop antenna and the MEMS capacitive pressure sensor form an LC resonator circuit. When the capacitance of the MEMS sensor changes because of IOP variation, the fundamental tone resonance frequency of the LC resonator circuit is shifted and results in a change of the resonance frequency of the 3rd order harmonic signal being transmitted back to the external receiver. This shift is then measured to determine the change in pressure being sensed by the MEMS sensor.

A system 2400 for measuring intraocular pressure according to one embodiment is shown in FIG. 24. First, a signal generator 2402 (e.g., a model N5182A by Agilent) which generates the fundamental tone signals is connected to a transmitting patch antenna 2404 through low pass filter 2406 and a power amplifier 2408. In the illustrated example, the power amplifier 2408 has a gain of 42 dB (5161 RF power amplifier by OPHIR RF), however it shall be understood that higher or lower gain values may be used depending on the particular application. In order to receive the reradiated 3rd order harmonic signal from an implanted pressure sensor tag 2410, a horn antenna 2412 is connected to a spectrum analyzer 2414 (e.g., a model E4408 by Agilent) via high pass filter 2416 and a low noise amplifier 2418. The mouse 2418 with the 3rd order harmonic tag inside its eye is anesthetized and placed on a heated surgical table. In the illustrated example, the transmitting patch antenna 2404 and the receiving horn antenna 2412 are placed at distances of 5.5 cm and 11.5 cm, respectively, away from the mouse eye. The distances are chosen to mimic the distance between the antenna and a mouse moving in a standard cage (30×30×15 cm³).

The frequency of the fundamental tone being output by the signal generator 2402 is swept from 2.2 GHz to 2.7 GHz, and the 3rd order harmonic signal is monitored from 6.6 GHz to 8.1 GHz on the spectrum analyzer 2414. In the illustrated example, the total power transferred to the patch antenna is 23 dBm. The pressure within the mouse eye is increased in 10 mmHg increments from 20 mmHg to 40 mmHg above atmospheric pressure, with the pressure kept constant for at least 10 minutes. IOP in mouse strains often varies between 5 mmHg to 40 mmHg under normal and disease conditions, with an IOP above 20 mmHg conferring increased glaucoma risk. The measurement range of 20 mmHg-40 mmHg is adequate to identify high IOP in some embodiments associated with glaucoma.

The collected data is fitted using a shape-preserving interpolant function in MATLAB. The resonance frequency of the 3rd order harmonic signal appears between 6.68 GHz and 6.73 GHz with the change in IOP between 20 mmHg to 40 mmHg. FIG. 25 shows the shift of the resonance frequency of the 3rd order harmonic signal. The data is normalized with respect to the maximum power level of each sweep. The average frequency shift of the 3rd order harmonic signal per unit pressure is approximately 1.5 MHz/mmHg, which is ultimately capable of monitoring an IOP variation of 1 mmHg from a mouse in a cage using the same measurement setup.

In some embodiments of the present disclosure, the sensor assembly (e.g., system 100) includes means for resolving the change in IOP. A differential two-stage amplifier according to some embodiments operates with a MEMS capacitive pressure sensor. It compares the value of the capacitance of the MEMS sensor with an internally adjustable reference capacitor and gives a differential output voltage to represent the difference. A correlated double sampling function is implemented to suppress the 1/f noise from the input transistors in the front-end amplifier, the offset voltage due to the amplifiers, and also errors due to the switches in the amplifier.

The capacitance measurement in some embodiments is taken by toggling the voltage on the common node between the two capacitors with a step voltage of value VS. This causes a differential voltage on the output of the pre-amplifier equal to VS(CM−CR)/CI. The value of CI is 180 fF.

There can be an input common mode adjust circuit, which compensates for the fact that the step voltage VS may alter the input common mode voltage. By adjusting the input common mode voltage in this way, the offset due to parasitic input capacitance mismatch can be minimized.

The clock generator gives four clocking signal for the amplifiers. They can be seen in the corner of FIG. 74. From these clocks, three phases are generated. The first is the reset phase where the capacitors are zeroed and the outputs are set to the common mode voltage level. In the sample_1 phase, the noise, including the 1/f noise is sampled onto the capacitors CH. Then in the sample_2 phase, the capacitor measurement is taken. Since the noise is relatively low in frequency compared to the sample rate, it has the same value between the sample_1 and sample_2 times and is cancelled. The total gain at the output is (CH/CII)(VS(CM−CR)/CI). The nominal base capacitance of the sensor can be variable. This variability is compensated for by dynamically adjusting the internal reference capacitor. When the supply voltage vdda is applied and the power-on-reset fires, the initial value of the reference capacitor will be relatively low compared to the MEMS capacitor. As each sample is taken, this value will be incremented with the counter until the value of reference capacitor is close to but slightly higher than the reference capacitor. When this happens, the comparator will fire and the value of the capsel bus coming from the counter will be latched. The clock signal vcsample is used for timing the comparator samples.

Some embodiments of the present invention include an amplifier which includes some or all of the following: 1/f noise suppression using CDS; tunable reference capacitor to allow for variation in the MEM base cap value; an input common mode adjust circuit to minimize output offset due to parasitic input capacitor mismatch; and low power (average current <50 uA). The following table presents specifications for an amplifier for amplifying a pressure signal according to some embodiments of the present invention:

| Block | Parameter | MIN | TYP | MAX | UNITS |
|---|---|---|---|---|---|
| CDS C-V | Power Consumptions (current) | | | 50 | uA |
| | Sample Rate | | 2 | | kHz |
| | Pressure Sensitivity | | 0.5 | | mmH |
| | Adjustable Base Cap | | 12.5 | | fF/bit |
| | No. Bits accuracy for pressure reading | | 9 | | ... Bits |

Various embodiments of the present disclosure pertain to the use of an analog to digital converter having more than about ten bits of resolution. A system according to one embodiment of the disclosure is shown in FIG. 26. Various aspects of the analog to digital conversion are shown in the following table:

| Specification | Targeted | Achieved | Note |
|---|---|---|---|
| Process | XFAB 180 nm | | |
| Voltage | 1.8 V +/− 10% | 1.8 V +/− 10% | Core devices for analog design |
| Current | <50 uA | 30 uA | Preliminary estimate |
| Mode | Fully differential | Fully differential | Better CMRR and 2x dynamic range |
| Input Signal range | 5 mV to 1.2 | V 5 mV to 1.2 V | |
| Input Signal Bandwidth | 1 KHz | 1 KHz | |
| Internal Clock | 250 MHz | 250 MHz | Stable clock source |
| Resolution | 10 bits | 10 bits | ENOB = 9 bits |
| INL | <1.5 LSB | <1 LSB | |
| DNL | <1 LSB | <1 LSB | |
| OP Code | Signed Magnitude | | 0111111111 = +1.2 V; 1111111111 = −1.2 V |
| Comparator Offset | <0.5 LSB | <0.5 LSB | |
| Comparator Resolution | <0.5 LSB | <0.5 LSB | Designed to be greater than 10 bits |
| Phase margin of Preamp | >55 deg | 72 deg | |
| Power | <100 uW | 60 uW | |
| Area | <350 um × 300 um | 320 um × 240 um | |

One eye pressure sensing system 2600 is shown in FIG. 26. The system employs a variable MEMS pressure sensor 2602, similar to sensors 114, 314, 414 to sense real-time eye pressure waveforms. The sensor changes its capacitance based on pressure applied to it and is processed by an on chip sensing circuit CDS-CV (Coherent Double sampling-Capacitance to Voltage converter) 2604, encoded by a 10 bit successive approximation register analog to digital converter (SAR ADC) 2606 and wirelessly send the data out by a transmitter 2608. Wireless RF signals from an external source (not shown) are captured at block 2612 and fed to power management block 2614 for powering the system 2600.

System 2600 preferably includes an ultra low power 10 bit SAR-ADC 2606 along with stable clock source 2610 to encode eye pressure signal waveform. FIG. 27 shows the top level schematic for an example 10 bit SAR ADC 2606. It includes the following blocks: (a) comparator 2702; (b) capacitor array (DAC and S/H) 2704; (c) delay elements and drivers 2706; (d) SAR control logic 2708; and (e) switches 2710. Discussion of these blocks is provided with reference to FIGS. 28, 29, 30, 31, 32, 33, and 34.

Figure 28:
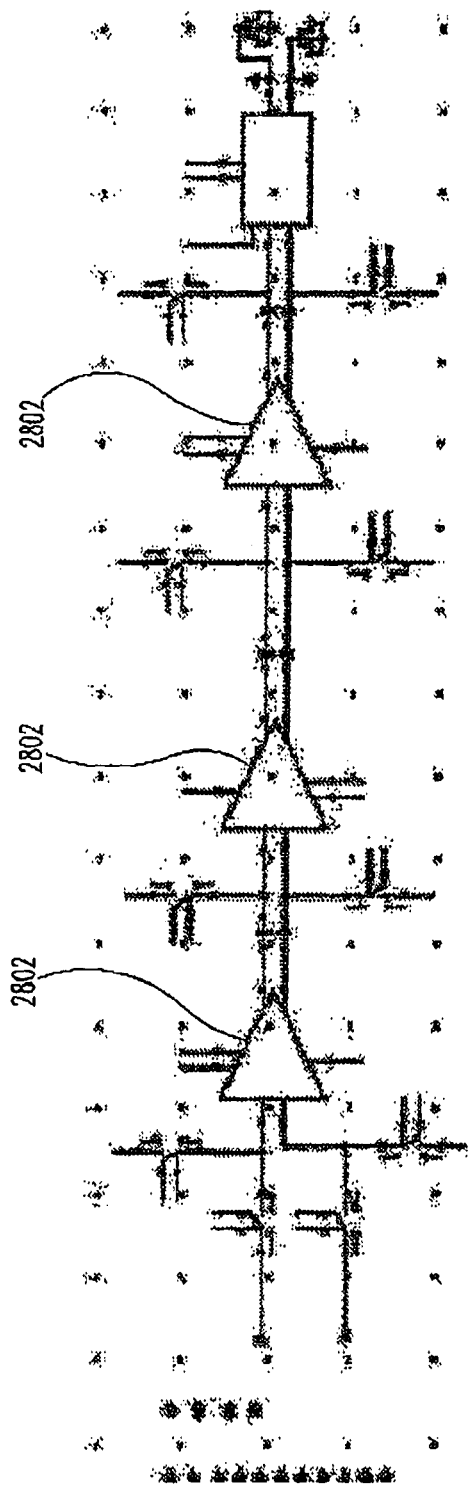
FIG. 28 is a top level schematic of comparator according to one embodiment.

Each A/D Converter contains at least one comparator 2702. A comparator itself can be considered a 1-bit A/D Converter. In the presented ADC design, the comparator plays a key role; it should be able to discriminate voltages as small as 878 uV. FIG. 28 shows the top level schematic for a comparator 2702 according to one embodiment.

A helpful specification is the offset voltage. The offset voltage should be smaller than 0.5 VLSB=878 uV. Clearly, to reach this requirement, offset-cancellation techniques should be applied. In fact, differential amplifiers, as the ones used in the pre-amplifiers 2802 of the comparator have an offset voltage of 1 mV to 10 mV if they are realized in CMOS technology. In practice, the residual offset after performing dynamic offset cancellation can be in tens of micro-volts.

Figure 29:
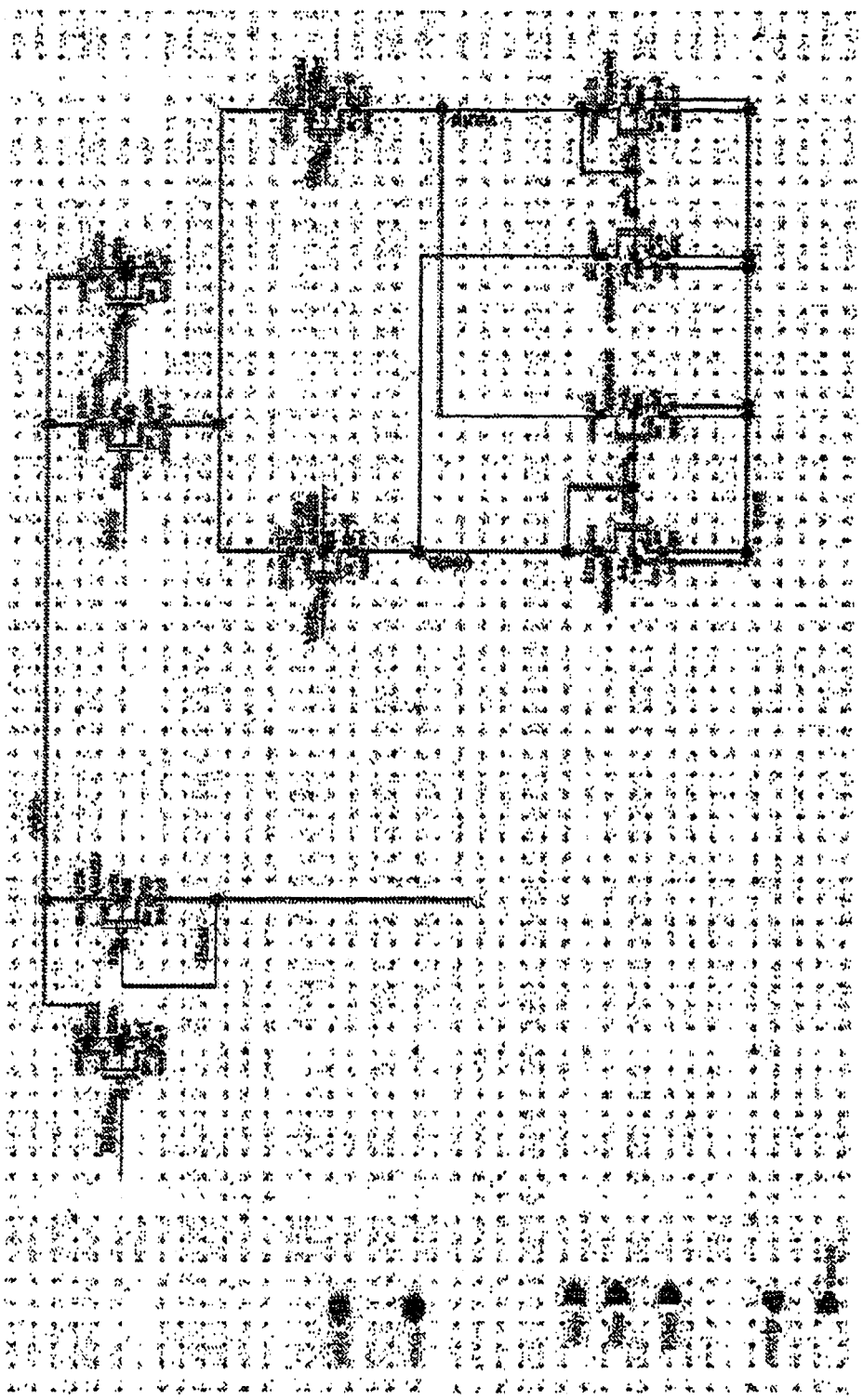
FIG. 29 is a preamplifier schematic design according to one embodiment.

In the illustrated embodiment, 3 amplifiers are employed for output offset storage and auto zeroing with 22 dB of gain. Preamps designed to have low offset. Each preamp is consuming 4 uA of current. The gain of a single preamp cannot go beyond 25 dB in output offset storage (otherwise amplifier output will saturate for high offset values), therefore 3 preamplifiers 2802 are used, each one if having 22 dB of gain. An example schematic for single preamplifier is shown in FIG. 29.

Figure 30:
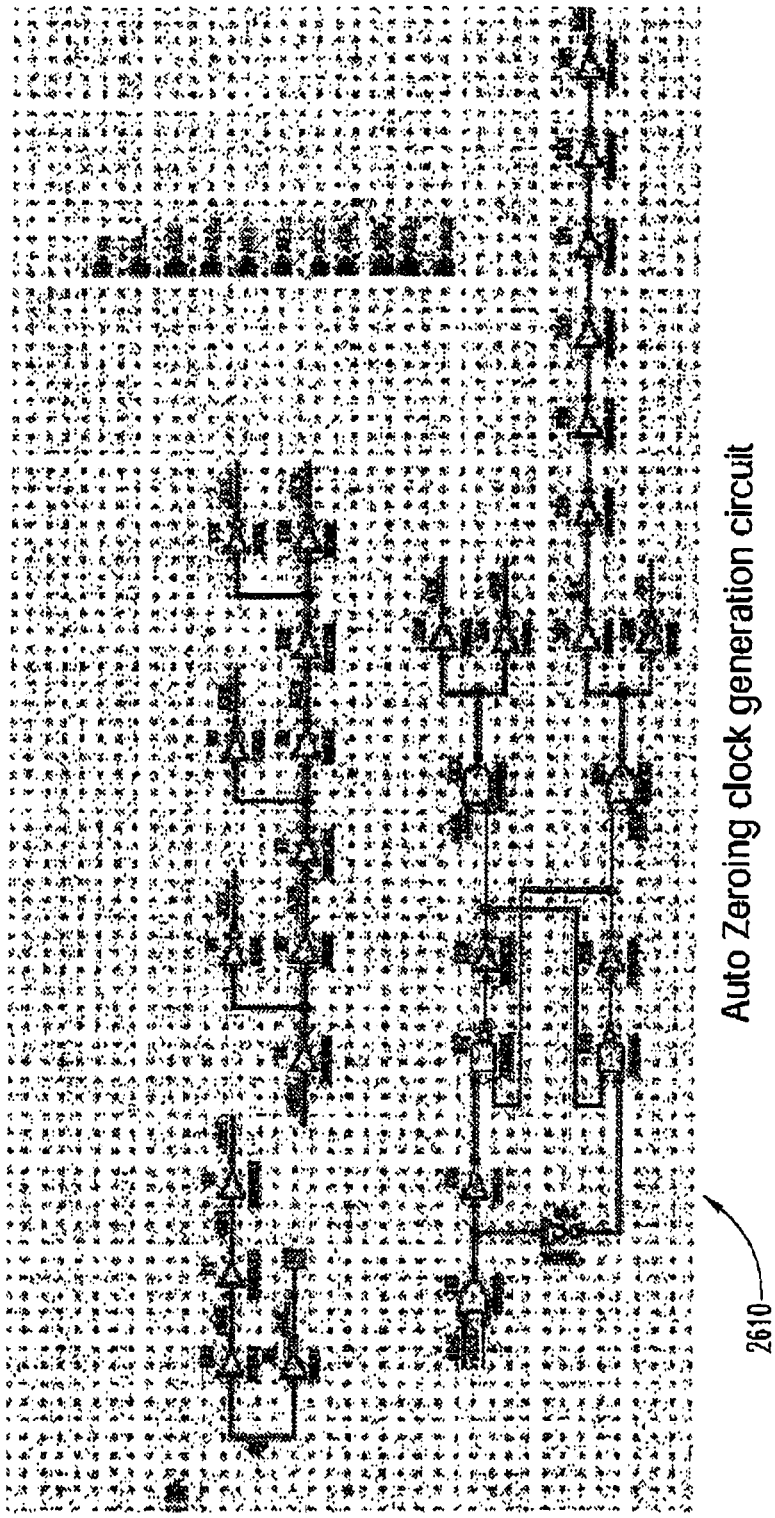
FIG. 30 shows an auto zeroing clock generation circuit according to one embodiment.
Figure 31:
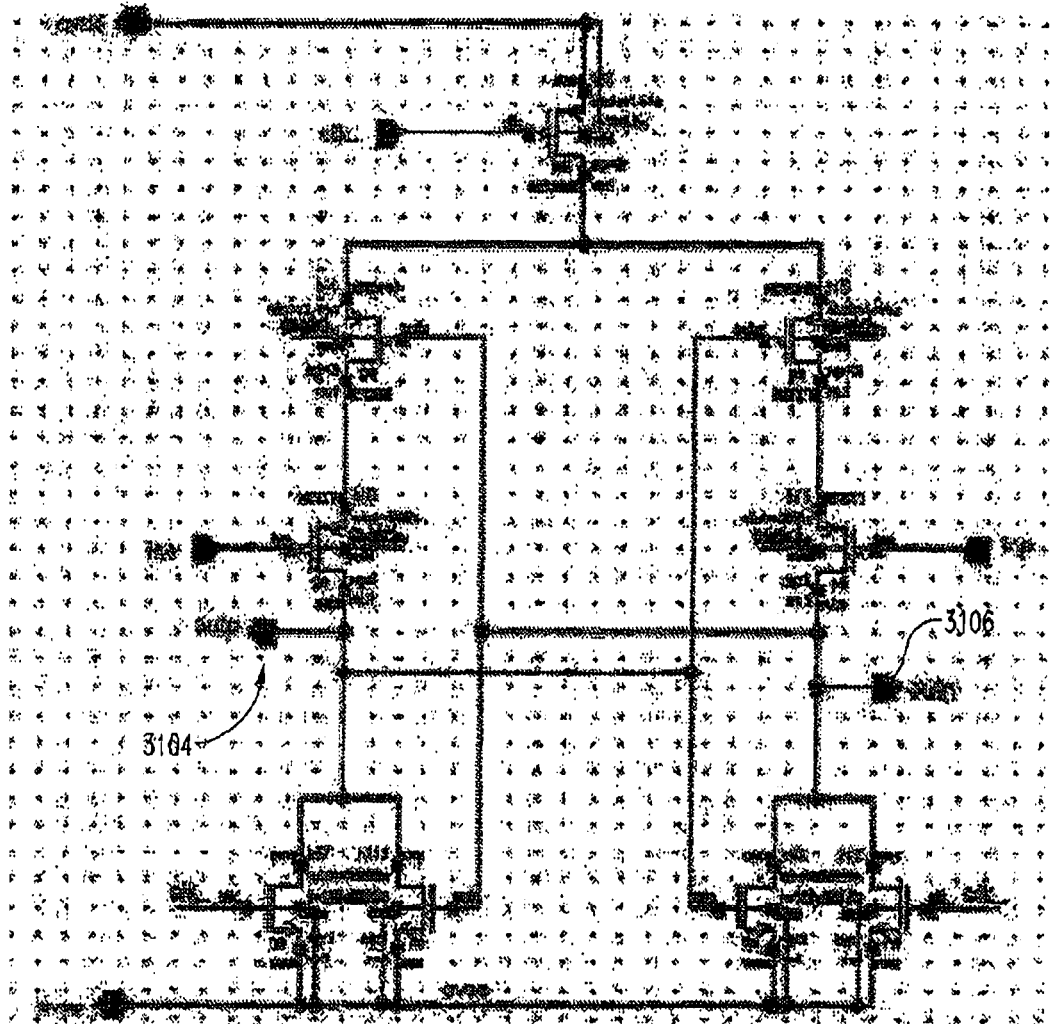
FIG. 31 is a schematic of a latch according to one embodiment.

An auto zeroing clock scheme is shown in FIG. 30. A non-overlapping clock signal is generated for auto-zeroing and offset cancellation. Sample and hold cycle and three auto-zero phase timings are a useful consideration in offset cancellation. The auto zero phase starts after a finite time delay (2 ns as one example) in hold phase of sample and hold cycle.

In order to establish full logic levels and synchronize the instant a decision is taken with other blocks, the back-end of the comparator 2702 includes a latch 3102. The output nodes outp 3104 and outn 3106 (see FIG. 31) are pre-charged to when the clock is low. To prevent static current flow through the two branches of the latch, a pMOS transistor controlled by clk_cuts off the cross-coupled inverter pair during the pre-charge phase. The amplified signal (output of preamplifier stage 3) is applied to the latch through the middle two pMOS transistors, which provide an additional gain. The pre-amplified signal can therefore overcome the offset voltage of the latch.

One implementation of SAR ADCs uses a binary weighted capacitor arrays, however, area and power increase exponentially with resolution. In fact, N-bit resolution requires $2^N$ unit capacitors.

Split capacitor arrays as well as C-2C ladders reduce the total capacitance, reducing area and power. However, the parasitic bottom-plate capacitance of series capacitors affects the linearity of the ADC. If the ratio of bottom-plate capacitance over nominal capacitance is precisely known, this non-linearity problem can be dealt with during the design phase by scaling some of the unit capacitors. Another approach includes shielding the series capacitors.

XFAB18.0 CMOS technology comes with a Metal Capacitor (MIM) module, also referred to as Metal Insulator Metal (MIM) capacitor module. For a lower bottom-plate parasitic capacitance, the MIM module can be inserted between the second-last and last (top) metal layers.

The unit capacitor sizing should consider KT/C noise, 10-bit accurate matching, timing and power consumption. To decrease power consumption and increase speed, the unit capacitor should be as small as possible. On the other hand, to improve MIM capacitor matching, noise immunity and consequently the ADC's accuracy, the unit capacitor should be as big as possible. One embodiment of the present disclosure includes a unit cap value as 84 fF, to consider trade-offs. The cap array is shown in top level schematic in FIG. 27.

The Successive Approximation Register (SAR) sets the switches—as a function of the current state of the conversion and the comparator's response—and stores the digital output code to be issued at the end of the conversion. The main building blocks of the SAR control logic are: (a) 4 bit counter; (b) output register; and (c) combinational network.

Figure 32:
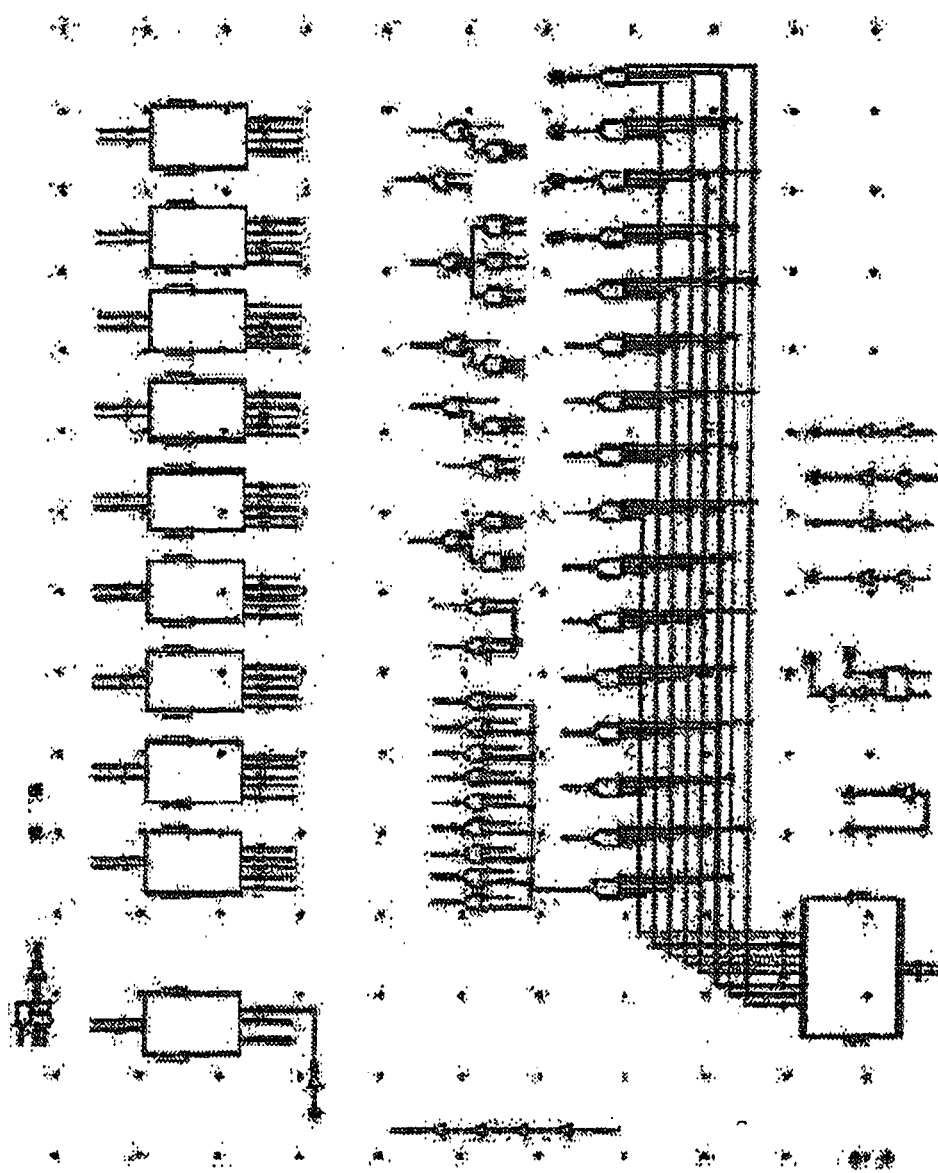
FIG. 32 is a top level schematic of 10 bit SAR Logic according to one embodiment.

FIG. 32 shows the SAR control logic and its sub blocks according to one embodiment. The 4 bit-Counter counts from 0 to 16, thereby cycling through the 10 states (some embodiments use 10 states out of 16 available) of one conversion. The counter is controlled by the 250 KHz reference clock or clk. The count or state of the counter changes on each positive transition of clock clk.

The combinational network calculates the control commands (Set, Reset and Select) for the output register bank, indirectly setting the switches, accordingly to the history of the current conversion. The output registers store the correct position of the switches for the current conversion and contain the output code at the end of the conversion. They are thus multifunctional. Their multi-functionality saves registers. The output registers eventually change their content on a positive transition of clk1, which is delayed with respect to clk.

The switches in this design are analog transmission gates. Cap array switch analog multiplexer and transmission gates are useful because of low and constant Ron requirement. FIG. 27 shows the analog Switches along with cap array.

Figure 33:
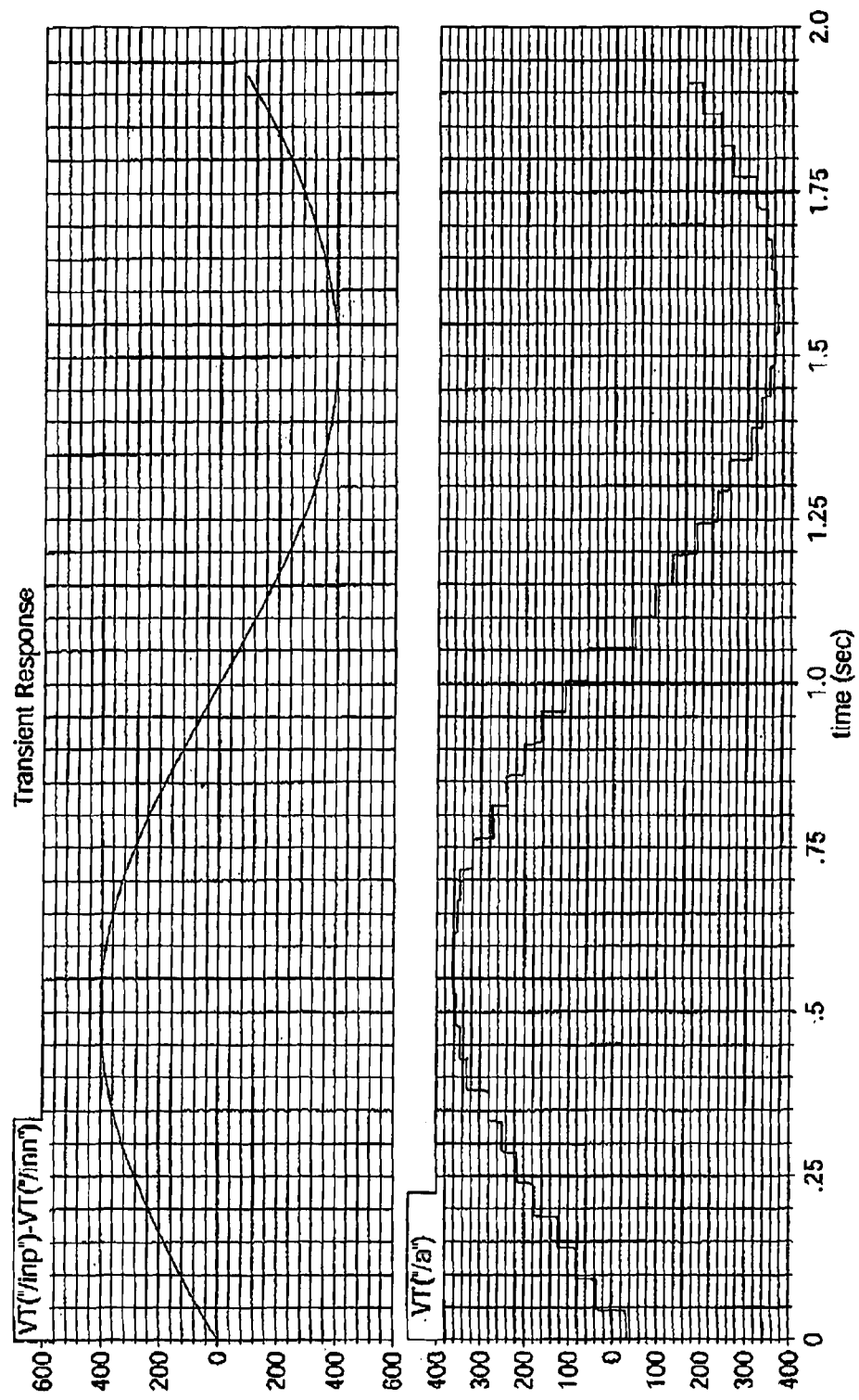
FIG. 33 is a top level simulation result for 10 bit SAR ADC (input=400 mV peak sinusoidal of 500 Hz) according to one embodiment.

As one example, a test of an at least partly differential sinusoidal signal of 400 mV peak to peak is applied to ADC input. Top level test bench is includes 10 bit SAR ADC, one shift register and one ideal DAC. The top level simulation results for ADC and Cap array DAC and sample and hold circuit are shown in FIG. 33.

Figure 34:
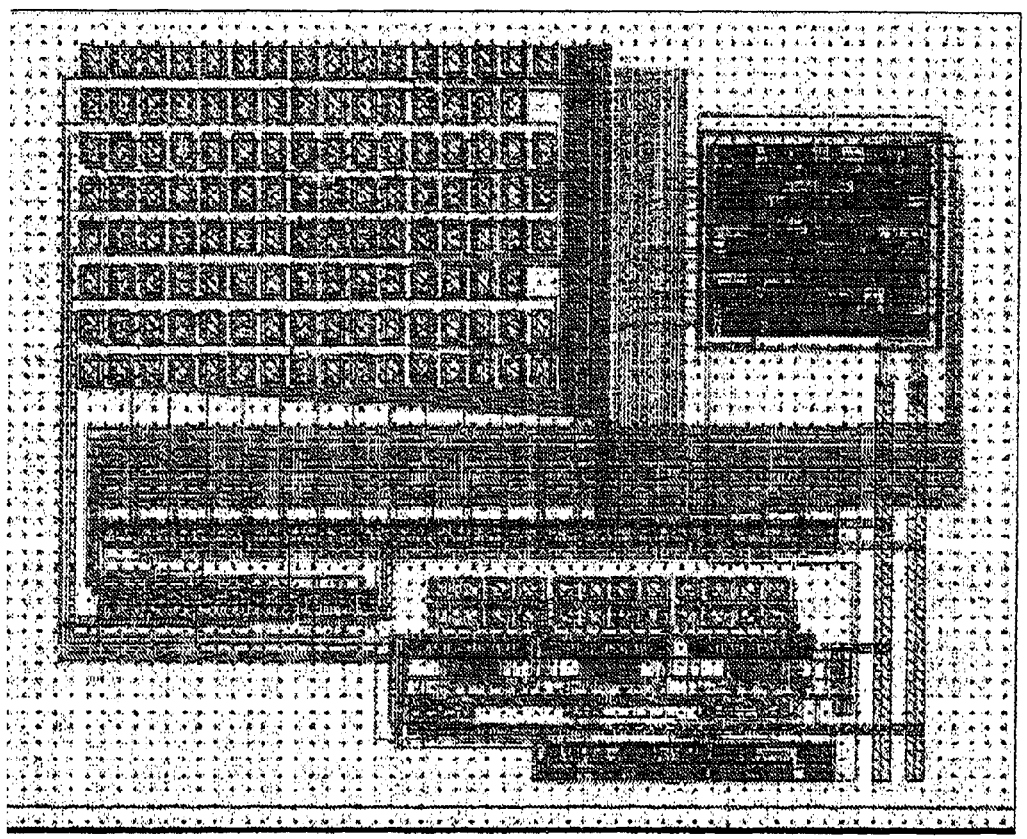
FIG. 34 is a SAR ADC top level layout (320 um×240 um) according to one embodiment.

A top level layout (without pads) is shown in FIG. 34. The top left and top right blocks are the cap array and SAR logic respectively. The comparator and S/H switches are shown on the bottom.

Pressure-sensing systems such as described above can be used in a variety of contexts other than IOP monitoring in mice or other animals. Numerous medical procedures and applications can benefit from extremely small pressure sensors that are biocompatible, flexible, and/or noninflammatory. For example, some embodiments may be used within the heart of a subject (e.g., a human) in any suitable procedure or application. The pressure-sensing system may include an active device (e.g., an integrated circuit) that is coupled with a passive device (e.g., a pressure sensor) that passively measures fluid pressure in the heart. The active device can transfer data out of the body to equipment configured to receive, store, and/or process the data.

Other or further embodiments may be used in the context of nephrology. For example, certain dialysis applications can benefit from sensor such as described herein. In some embodiments, a pressure-sensing system can be coupled with (e.g., integrated into) a catheter, such as a central venous dialysis catheter. The pressure-sensing system may be positioned at an outer surface of the catheter. The system can be used to measure blood pressure during dialysis and ensure that the pressure does not drop below a certain safety level. The sensors thus can be used to prevent the triggering of cardiac arrest.

Other or further embodiments can be used to track the pressure of cerebral spinal fluid. For example, pressure-sensing systems such as disclosed herein can be implanted in the skull so as to monitor the onset or progression of hydrocephalus.

Still other or further embodiments can be used as monitoring devices for breast implants. For example, a silicone breast implant could include a pressure-sensing system. The pressure-sensing system may be free floating within the breast implant or attached to an inner surface of the breast implant. The placement of a silicone breast implant in the body (especially when it's submuscular, e.g., beneath the pectoralis major) creates a certain pressure within the breast implant that exceeds the pressure outside, since the surrounding body tissue has a compression effect on the implant. The pressure-sensing system can be configured to transmit data regarding the fluid pressure within the implant to remote equipment. If a rupture occurs, the pressure within the breast implant will drop as the implant fluid (e.g., silicone or saline) leaks out and the volume of the implant decreases. The drop in pressure is detected by the pressure sensor and/or remote equipment. Such a system can advantageously provide an early warning system for implant rupture, and can reduce the number or frequency of checkup visits for patients at which expensive MRIs are generally performed.

Yet other embodiments include the use of the disclosed pressure sensors in a cranial cavity (such as for real-time monitoring of cranial pressure), and implantation in a spinal cavity (for real-time monitoring of the pressure of spinal fluid).

It is contemplated that the test methodologies used in the below examples and others disclosed herein may be used to test any embodiment.

Example 1

Biocompatibility Testing

Various embodiments of the present disclosure can include various types of coating of the implantable device. Additional tests include a parylene coating often used to ensure biocompatibility for implantable devices. The effect of coating a low temperature co-fired ceramic (LTCC) with parylene was explored and compared to quantify the possible improvement of biological tissue response. Testing was also done on alumina, which is used as a baseline material for biocompatibility comparisons.

Biocompatibility was verified through in-vivo trials performed on 6 New Zealand White Rabbits. This animal model was chosen in accordance with ISO standards for biocompatibility testing. The comparative study done in this work focuses on ISO 10993-part 6, which delineates tests for local effects after implantation including inflammatory response and fibrous encapsulation.

Surgical procedure follows the Purdue Animal Care and Use Committee (PACUC) approved protocol (PACUC No. 08-004) beginning with a one-week acclimation period prior to surgery. Surgery begins with the injection of an anesthetic induction solution comprised of ketamine and xylazine. After anesthetization, verified by a toe-pinch test, anesthesia was maintained by an intravenous (IV) drip of Propofol. Prior to incision, a local anesthesia, Zylocaine, was injected at each implantation site. Incisions were made along the dorsal side of the rabbit and deepened into the muscle tissue. The alcohol-sterilized materials were implanted into the muscle and the incisions are sutured and stapled to seal the layers of muscle, subcutaneous tissue, and dermis. The rabbits were given analgesics and triple antibiotic ointment as needed.

Histological examination was used to evaluate the inflammatory response and fibrous encapsulation. After implantation durations of 1 week, 2 weeks, and 4 weeks, the animals were euthanized through an injection of sodium pentobarbital solution. The implant along with the surrounding tissue was excised. The extracted samples were embedded in paraffin wax and sliced into 50 μm thick sections using a vibratome. The tissue was stained to provide contrast using a solution of Mayer hematoxylin paired with eosin. Specifically, eosin was used to highlight the elastic and reticular fibers while hematoxylin targets the nucleic acids and ergastoplasm. Optical microscopic examination was then performed on the stain-enhanced tissue slices and the fibrous encapsulation is quantified.

Initial inspection evaluating inflammation showed minor redness without uniform density in all materials through the first 2 weeks of the in vivo studies. After the 4-week implantation period, DuPont™ 951 and alumina still had visible minor redness while there was no visible inflammation in the other materials used in the study.

To quantify the results, histological analyses of tissue slices were performed and fibrous encapsulations measured at three different points around the implant site for all 6 rabbits. Optical micrographs of the material cases with the good tissue response, LCP and parylene coated LTCC, are shown in FIG. 38. Thickness measurements at the tissue-material interface are averaged and the data is tabulated in Table 6.2.1. The different columns represent the measurements taken at various implantation durations of 7 days, 14 days, and 28 days. Post-surgery healing and corresponding inflammation influence the day 7 and 14 measurements. After 28 days, the lack of post-surgery healing effects allow for more precise measurements of the biological tissue reaction in the form of fibrous encapsulation.

TABLE 8.2.1

Material Encapsulation Thickness

| Material | Encapsulation after 7 days (mm) | Encapsulation after 14 days (mm) | Encapsulation after 28 days (mm) |
|---|---|---|---|
| DuPont ™ 951 | 0.223 | 0.026 | * |
| DuPont ™ 943 | 0.336 | 0.012 | 0.018 |
| Heraeus HL2000 | 0.070 | 0.019 | 0.059 |
| Parylene Coat | 0.201 | 0.015 | 0.000 |
| LCP | 0.046 | 0.005 | 0.000 |
| Silicon | 0.098 | 0.004 | 0.000 |
| ACA | 0.185 | 0.059 | 0.017 |
| Alumina | 0.081 | 0.020 | 0.036 |

*Data could not be extracted due to slicing error

The data for all the tested materials are compared with that of the baseline, alumina, and the differences are tabulated in Table 6.2.2. Each column represents the thickness differences in comparison with the alumina case for the corresponding implantation duration. A plus sign represents more fibrous encapsulation than alumina while a minus sign represents less encapsulation; the measurements plotted in FIGS. 39-41. FIG. 39 show a comparison between the materials after an implantation duration of 7 days, FIG. 40 shows 14 days, and FIG. 41 represents the results after 28 days. The plots show the averages of the multiple data sets and the corresponding standard deviations.

TABLE 6.2.2

Encapsulation thickness with respect to control (alumina)

| Material | Encapsulation after 7 days (mm) | Encapsulation after 14 days (mm) | Encapsulation after 28 days (mm) |
|---|---|---|---|
| DuPont ™ 951 | +0.142 | +0.007 | * |
| DuPont ™ 943 | +0.255 | −0.008 | −0.018 |
| Heraeus HL2000 | −0.011 | 0.000 | +0.023 |
| Parylene Coat | +0.120 | −0.005 | −0.036 |
| LCP | −0.035 | −0.015 | −0.036 |
| Silicon | +0.017 | −0.015 | −0.036 |
| ACA | +0.104 | +0.039 | −0.019 |
| Alumina | 0.000 | 0.000 | 0.000 |

All material cases show a decreasing trend in biological tissue reaction as a function of time elapsed post-surgery. An error occurred in the slicing of the DuPont 951 four week trial samples causing thick abnormal slices of the material. Even though this prevented accurate thickness measurements, the data from the two week (14 day) implantation case provides a reasonable estimate of the fibrous encapsulation effects for the DuPont 951.

After one week, the comparisons, plotted in FIG. 39, show that the Heraeus HL2000 LTCC, LCP, and silicon had the least amount of encapsulation. LCP had the best performance out of all the materials and both LCP and HL2000 outperformed the baseline, alumina. DuPont 943 LTCC had the highest rate of encapsulation followed by DuPont 951 that had only slight more fibrous tissue than the same material coated in parylene.

The tissue reaction measurements significantly decreased for all materials after 2 weeks, shown in FIG. 40. The percentage of encapsulation reduction ranged from 68.1% to 96.4%. The data at 14 days showed that LCP and silicon caused the least amount of reaction. Some materials (DuPont 943, HL2000, parylene coated 951, LCP, and silicon) had less encapsulation than alumina. Only DuPont 951 and ACA had more tissue reaction than the control.

The encapsulation continued to be minimal for the 28 day implantation duration, plotted in FIG. 41, decreasing in some cases from the 14 day measurements. LCP, parylene coated 951, and silicon had submicron encapsulation. The only material that had more reaction after the 4-week period than alumina is the HL2000. The DuPont 943 and HL2000 are the only two materials that had increased encapsulation from the 2-week to 4-week periods.

Data obtained over the 28 day study allow ratings for each material following the NAMSA Good Lab Practices (GLP) protocol (NAMSA No. T1250_812). Post-surgical healing influenced encapsulation measurements in the first week but more accurate quantifications of material-tissue interactions are obtained at the 2 and 4-week cases. A NAMSA rating of 1 represents up to 0.5 mm capsule or reaction area, which is representative of all the measurements for the in-vivo studies for all time periods. Parylene coated DuPont 951, LCP, and silicon, had no capsule or adverse reaction after the 28 day implant duration and thus have a rating of 0. The silicon and parylene coated LTCC ratings are consistent with that described in. This minimal tissue reaction for silicon and parylene coated LTCC cases are also seen for the LCP.

From Table 6.2.2, there are only two points where there is a statistically helpful difference in inflammation with comparison to alumina. These occur in the Heraeus HL2000 data at 7 days, and Anisotropic Conductive Adhesive at 14 days as an over inflammation compared to alumina.

Example 2

Implant Testing

To test in-vivo functionality, two surgical procedures have been implemented; one for the rabbit animal model (human IOP) and one the mouse animal model. Throughout the rabbit surgical procedure, sterile saline is applied at regular intervals to the operated eye (experimental eye) to prevent drying. The animals are implanted in one eye (other non-operated eye serves as histological control) with a custom, intraocular pressure monitor device in the suprachoroidal space. After insertion of a lid speculum, a bridle suture can be used to isolate the eye during the procedure.

A conjunctival incision is performed posterior to the limbus, using a diagonal incision to create a flap. A 3 mm wide scleral incision to full thickness is performed 2 mm posterior to the limbus to expose the surface of the choroid. A blunt spatula was used to separate the sclera and choroid surface, anteriorly and posteriorly, and the pressure sensor device is implanted into this space. If necessary, the device can be sutured to the sclera to prevent migration. The sclera is closed over the device with two 10-0 nylon sutures. If necessary, the conjunctiva is closed with one or two 10-0 vicryl sutures. A surgical sealant is applied to the surface of the cornea to aid in wound healing. The surgical sealant used will be a cyanoacrylate-based Bioglue as our primary anterior chamber sealant, followed by Healon if necessary. An antibiotic, gentamicin or tobramycin was administered after wound closure.

A stab incision of about 1 mm was made at about 3-5 mm from the corneal limbus using a 3 mm microsurgical blade, or similar device. A volume of Viscoat Viscoelastic or similar solution is used to form the anterior chamber to allow for better manipulation of the sensor, while minimizing trauma to the eye. (Viscoat Viscoelastic or similar solutions are sterile, non-pyrogenic, transparent viscoelastic preparations of a highly purified, noninflammatory, high molecular weight sodium hyaluronate or similar substances. These substances are routinely used in anterior segment ophthalmic surgical procedures in humans. It coats the iris, posterior corneal surface and anterior lens capsule, which helps protect these tissues from injury during the surgical procedure.) The sensor is inserted through the incision, the incision sutured, and the Viscoat Viscoelastic removed. Finally, a topical antibiotic, Vetropolycin, is applied to decrease infection risk.

As seen in the FIGS. 42 and 43, the device is properly implanted into the eye of the rabbit and mouse respectively. Issues have arisen with the tadpole design, as seen in FIG. 42, still using the trochanter implantation design, whereas the implantation of the CTR device (FIG. 43), was a fluid insertion without a trochanter. As the system is further developed, integration of a trochanter streamlines the insertion procedure further. With this implantation procedure the mouse surgery has been successful in implanting the device and lighting of an LED (FIG. 45.).

Example 3

Testing of Vascularization of Eye Following Implantation of LED Device

One eye was kept as a control and the second eye contained the implant. The results shown from the histological procedure produce results of how the vasculature has grown due to the inflammatory responses.

Figure 66:
FIG. 66 shows the vascularization of a mouse eye following implantation of an LED device. Blue indicates vascularization. Purple is reflectance.

The blue labeling is the vasculature and the purple is the retina tissue. It is observed that the vasculature grows toward the implantation location, and some healing is necessary. FIG. 66 is the depiction of the eye after one week of implantation. As the edema sets in and inflamatory response from the mouse increases, vascularization is increasing toward the center.

Figure 67:
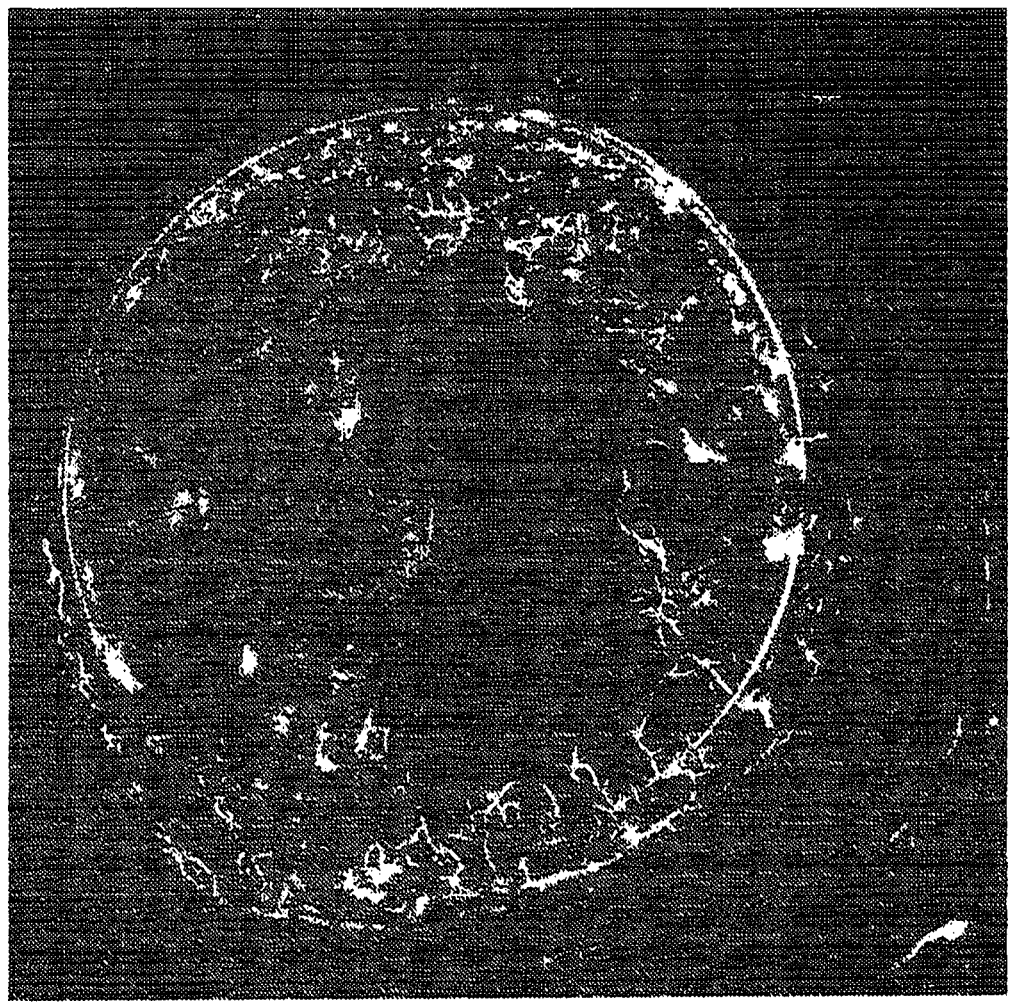
FIG. 67 shows a histological response 2 weeks post-mortem. Blue is the vascularization. Purple is reflectance.
Figure 68:
FIG. 68 shows a 3D recreation of a mouse eye 2 weeks after implantation of an LED device. Color incorporates depth. Red constitutes tope white blue is farther away from lens.

A successful implantation that did not damage the cornea during surgery is shown in FIG. 67. This will give a better understanding of the inflammatory response, since this eye was excised two weeks after implantation. Again using the same system, the vascularization stays toward the edge of the eye. Further analysis shows where the points of contact are with the implanted device as well as the implantation incision. Since the device is observed in purple, there are two aspects to observe. These are in the top right and bottom left locations. The top right location is where the incision was made to implant the device, while the bottom left is the location where the tab was be interacting with the tissue. Due to the incision procedure, the tab was caught on the iris, causing damage. This risk needs to be mitigated in further designs of the IOP device. Further, this data can be used to make a 3D recreation of the eye (FIG. 68). The resulting colors depict distance from the top of the eye (apex of the cornea). Initially the implant substrate sits high, while the ring and components sit lower inside the eye.

It will be understood by those having skill in the art that changes may be made to the details of the above-described embodiments without departing from the underlying principles presented herein. For example, any suitable combination of various embodiments, or the features thereof, is contemplated.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially planar" is recited with respect to a feature, it is understood that in further embodiments, the feature can have a precisely planar orientation.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this original written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the preceding claims up to and including claim [x]," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claims 1, 2, or 3, with these separate dependencies yielding three distinct embodiments; claim 5 can depend from any one of claims 1, 2, 3, or 4, with these separate dependencies yielding four distinct embodiments; and so on. Similarly, for the second claim set that begins with independent 10, claim 12 can depend from either of claims 10 and 11, with these separate dependencies yielding two distinct embodiments; claim 13 can depend from any one of claims 10, 11, or 12, with these separate dependencies yielding three distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C. §112 ¶6. Embodiments of the disclosure in which an exclusive property or privilege is claimed are defined as follows.

What follows are further descriptions of various embodiments of the present invention. It is understood that these descriptions that follow (A, B, C, D) are examples of various embodiments, and are not to be considered as limiting statements. Following these four statements are yet further statements that describe additional aspects of any or all of the primary statements (A, B, C, D). It shall be understood that any aspects or features of the below described embodiments may be combined with any of the embodiments or features described elsewhere herein to form still further embodiments.

A. An apparatus for measuring pressure in a media, comprising:
 a sensor providing a first signal corresponding to the pressure of the media;
 an antenna for receiving and transmitting radiowaves;
 a first circuit for receiving the first signal and providing a second signal for transmittal by said antenna;
 a second circuit for receiving radiowaves from said antenna and providing electrical power to said sensor and said second circuit.

B. An apparatus for measuring pressure in a media, comprising:
 a sensor providing a first signal corresponding to the pressure of the media;
  a circuit receiving the signal and providing an output; and
  an antenna for transmitting the output as a radiowave, said antenna being fabricated from a shape memory material;
   wherein said antenna does not have a free end.

C. A system for monitoring the response of an animal, comprising:
 a base station including a source of radiowaves, a receiver of radiowaves and an electronic controller including software;
 a sensing assembly completely implantable in the animal and adapted and configured for wireless communication with said base station, said sensing assembly being actively powered by the source and transmitting data to said receiver; and
 a platform for supporting the animal located proximate to said receiver and proximate to said source;
 wherein said controller receives the data from said receiver, and said software provides output corresponding to the data.

D. A method for monitoring the response of a non-human animal, comprising:
 providing an actively powered sensor including an antenna fabricated with an elastically deformable material;
  making an incision in an eye of the non-human animal;
  elastically collapsing the antenna;
  inserting the sensor and collapsed antenna through the incision and into a space within the eye;
  powering the sensor by radiowaves received by the antenna; and
  receiving data from the sensor by radiowaves.

The apparatus of any of statements A, B, C, or D wherein the largest dimension of the apparatus is less than about ten millimeters.

The apparatus of any of statements A, B, C, or D wherein the apparatus is adapted and configured for placement in the chamber between the iris and the cornea of an eye.

The apparatus of any of statements A, B, C, or D wherein the media is a fluid within an animal eye.

The apparatus of any of statements A, B, C, or D wherein the animal is human.

The apparatus of any of statements A, B, C, or D wherein the animal is non-human.

The apparatus of any of statements A, B, C, or D wherein the media is a fluid within a spinal cavity.

The apparatus of any of statements A, B, C, or D wherein the media is a fluid within a cranial cavity.

The apparatus of any of statements A, B, C, or D wherein the media is a fluid within a pliable container.

The apparatus of any of statements A, B, C, or D wherein the container is a breast implant.

The apparatus of any of statements A, B, C, or D which further comprises a flexible substrate, wherein said sensor, said first circuit, and said second circuit are mounted to said flexible substrate.

The apparatus of any of statements A, B, C, or D wherein said sensor and said first circuit are in electrical communication, and the communication is through said substrate.

The apparatus of any of statements A, B, C, or D wherein said antenna is adapted and configured for receipt of radiowaves having a frequency greater than about one gigahertz.

The apparatus of any of statements A, B, C, or D wherein said antenna does not have a free end.

The apparatus of any of statements A, B, C, or D wherein said sensor includes a capacitor the capacitance of which changes with pressure in the media.

The apparatus of any of statements A, B, C, or D wherein said antenna receives radiowaves at a frequency and said antenna transmits the second signal at a harmonic of the frequency.

The apparatus of any of statements A, B, C, or D wherein said antenna is in the shape of a circular loop.

The apparatus of any of statements A, B, C, or D wherein said antenna has two ends, and each said end is attached to one of said sensor or said circuit.

The apparatus of any of statements A, B, C, or D wherein the material includes Nitinol.

The apparatus of any of statements A, B, C, or D wherein said antenna is readily collapsible prior to implantation in a biological space of an animal, and expands to a generally curved shape after implantation.

The apparatus of any of statements A, B, C, or D wherein said antenna expands to a size and shape that stabilizes the apparatus at a generally fixed location in the biological space.

The apparatus of any of statements A, B, C, or D where the geometry of the antenna is adapted and configured for resonance within a biological space containing the media.

The apparatus of any of statements A, B, C, or D wherein the sensing assembly is a pressure sensor implanted in the eye of the animal.

The apparatus of any of statements A, B, C, or D wherein the data is provided in real-time and the output is provided in real-time.

The apparatus of any of statements A, B, C, or D wherein said sensing assembly includes memory that is repeatedly programmable, and the memory is programmed with information transmitted by said source.

The apparatus of any of statements A, B, C, or D wherein said source is operates at a first frequency, and said receiver operates at a harmonic of the frequency.

The system of any of statements A, B, C, or D wherein the harmonic is the third harmonic.

The system of any of statements A, B, C, or D wherein the platform includes means for restraining the animal.

The apparatus of any of statements A, B, C, or D wherein the space is between the iris and the cornea.

The apparatus of any of statements A, B, C, or D which further comprises expanding the antenna to a non-collapsed shape after said inserting.

The apparatus of any of statements A, B, C, or D which further comprises transmitting data by the antenna prior to said receiving.

The apparatus of any of statements A, B, C, or D wherein said powering is at a frequency and said transmitting is at a different frequency.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

APPENDIX A

Figure 49:
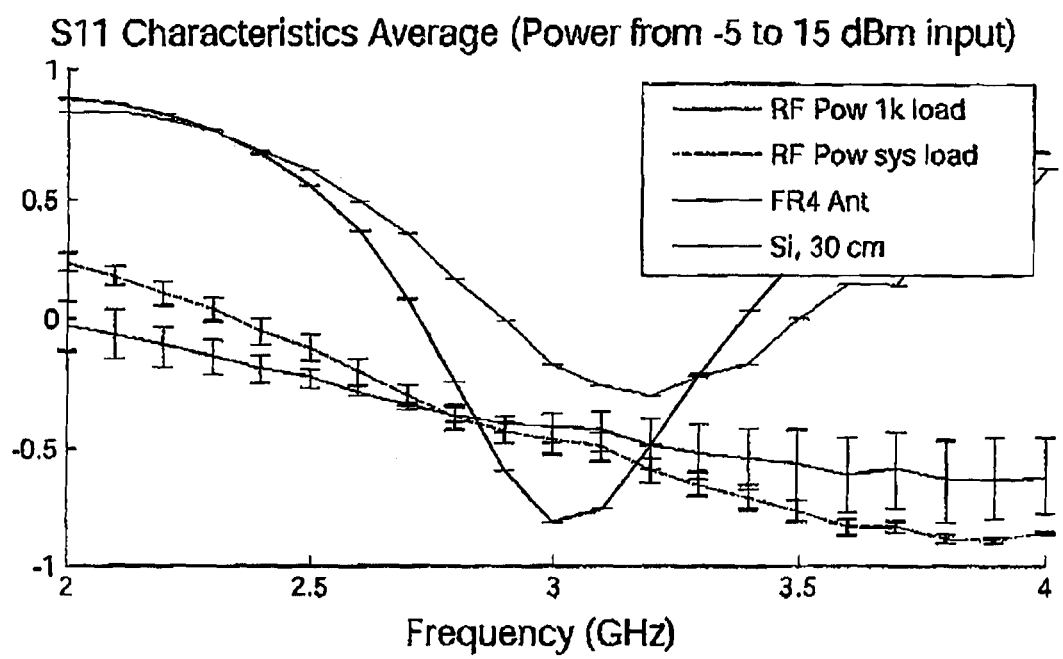
FIG. 49 shows plots of a reflection coefficient characterization of components of obtaining and harvesting RF energy (a) real and (b) imaginary, according to one embodiment.

When connecting circuitry that captures, or converts GHz waves, it is helpful that this efficiency be at a high percentage. Commonly most circuitry is matched to a 50 ohm circuit. Therefore if two systems are connected together and each system is seen as a 50 ohm load, theoretically the maximum efficiency is achieved when transferring power between the two components. When designing the antenna and rectification circuitry however, these systems were not perfectly matched to 50 ohms. This mismatch (FIG. 49) can be seen between the different type of antenna, how it is fabricated, and the loads on those systems. FIG. 49 shows the imaginary and real aspects of the S11 parameter. This S11 parameter describes the reflection coefficients of the components, and can be used to determine efficiency of a circuit.

To determine efficiency, the reflection coefficient S11 or $\Gamma$ is made up of a complex number (equation 8.1).

$$S_{11} = \Gamma = A + jB \qquad \text{Equation 8.1}$$

Using the Pythagorean theorem the magnitude of the reflection coefficient (equation 8.2) is used to determine efficiency of a power transfer (Equation 8.3).

$$\Gamma^2 = A^2 + B^2 \qquad \text{Equation 8.2}$$

$$\text{Eff} = \frac{P_{act}}{P_{in}} = (1 - |\Gamma|^2) \qquad \text{Equation 8.3}$$

As described in Table 8.2, we see that each independent block of the system has different efficiencies at a given frequency. Since 2.5 GHz is used for the powering frequency, this is reflected in the results of Table 8.3

To understand how the systems need to interact and improve efficiency, the impedance of the circuit is calculated. Since initial testing is conducted under a 50 ohm input condition, the overall impedance of each of the circuits can be calculated using equation 8.4.

$$\Gamma = \frac{Z_L - Z_0}{Z_L + Z_0} \qquad \text{Equation 8.4}$$

Where $Z_L$ is the impedance of the load (antenna, rectifier, etc.) and $Z_0$ is 50 ohms. Rearranging equation 8.4 will give an equation 8.5

$$Z_L = \frac{50(1 + \Gamma)}{(1 - \Gamma)} \qquad \text{Equation 8.5}$$

Even if the efficiency as seen in Table 8.3, is low, this is with respect to a 50 ohm load. Changes occur when the two systems are compared with each other.

TABLE 8.3

Reflection coefficients and efficiency at 2.5 GHz

| 1 k Load | | System Load | |
|---|---|---|---|
| Real | Imag | Real | Imag |
| −0.244 ± 0.039 | −0.533 ± 0.210 | −0.122 ± 0.052 | −0.951 ± 0.008 |
| 65.62% Eff | | 8.09% Eff | |
| FR4 Substrate | | LCP substrate | |
| Real | Imag | Real | Imag |
| 0.529 ± 0.001 | −0.844 ± 0.000 | 0.592 ± 0.001 | −0.718 ± 0.001 |
| 0.78% Eff | | 13.40% Eff | |

Looking at the two blocks, in this case one rectifier, and one antenna, a new reflection coefficient can be determined from the two blocks.

Understanding the initial conditions of $$\Gamma_{ANT} = C + jD \qquad \text{Equation 8.6}$$

$$\Gamma_{REC} = A + jB \qquad \text{Equation 8.7}$$

And understanding that using equation 8.5, impedance can be determined giving equations 8.8 and 8.9 from equations 8.6 and 8.7.

$$Z_{ANT} = Y + jZ = \frac{50(C + jD + 1)}{(1 - (C + jD))} \quad \text{Equation 8.8}$$

$$Z_{REC} = W + jX = \frac{50(A + jB + 1)}{(1 - (A + jB))} \quad \text{Equation 8.9}$$

Knowing these two equations, and setting them to match to the antenna (rectifier is the load), two new equations are built from rearranging (equations 8.8 and 8.9)

$$Z^*_{ANT} = Y \quad \text{Equation 8.10}$$

$$Z^*_{REC} = W + j(X - Z) \quad \text{Equation 8.11}$$

Equation 8.11 has X+Z in the imaginary due to conjugate matching of the tow systems.
Then, equations 8.10 and 8.11 can be placed into the overall equation for gamma (equation 8.4) to determine the overall efficiency using equation 8.3 of the circuit.

$$\Gamma_{NEW} = \frac{(W - Y + j(X - Z))}{(W + Y + j(X - Z))} \quad \text{Equation 8.12}$$

Using these equations the efficiencies of both rectifiers under the full system load as well as the antenna are in the single digit efficiencies. From FIG. 69 it is observed that the highest efficiencies are not in the 2.5 GHz ISM band, but between 3 and 3.5 GHz. Specifically at 2.5 GHz, there are efficiencies of 0.204%, 3.74%, 0.0172, 0.328% for a comparison of 1 kload and FR4 antenna, 1 kload and LCP antenna, full system load and FR-4 antenna, and full system load and LCP antenna respectively. Their peaks are 71% at 3.2 GHz, 85.2% at 3.3 GHz, 86.0% at 3.2 GHz, and 36.0% at 3.3 GHz for the same respective comparisons.

The data obtained on the complex impedances can be further observed on a smith chart. Using that information, it is noticed that both the impedance of the antenna and the impedance of the system lie outside the 1+jω circle. Therefore, a matching network (FIG. 70) is used to increase the efficiency between the antenna and rectifier.

FIG. 70 incorporates two extra components to match the load impedance (rectifier and system) with the source impedance (Antenna.) To determine values necessary for optimum transfer of power, one must first determine the value of the components. This starts with equation 8.13.

$$\frac{1}{Z_s} = jB + \frac{1}{R_L + j(X + jX_L)} \quad \text{Equation 8.13}$$

Using equation 8.13, the unknown variables X and B are solved to determine the correct inductances and capacitances. By rearranging equation 8.13 into equation 8.14, the equation is split into terms of real and imaginary components (equations 8.15 and 8.16).

$$R_L + j(X + X_L) = Z_S - (X + X_L)BZ_S + j(BR_L Z_S) \quad \text{Equation 8.14}$$

$$(X + X_L)BZ_S = Z_S - R_L \quad \text{Equation 8.15}$$

$$(X + X_L) = BR_L Z_S \quad \text{Equation 8.16}$$

This gives two equations with two unknowns. Rearranging equation 8.15 and placing into equation 8.16 will give one equation with one unknown. One can input data back into the second and solve for the missing parameter (equation 8.18).

$$B = \pm \frac{\sqrt{(Z_S - R_L)/R_L}}{Z_S} \quad \text{Equation 8.17}$$

$$X = \pm \sqrt{R_L(Z_S - R_L)} - X_L \quad \text{Equation 8.18}$$

Using the values for X and B, resulting values for capacitance and inductance are solved. As an example, using the reflection coefficient parameters from Table 8.4, the impedances of FR-4 and full system at 2.5 GHz are determined using equations 8.8 and 8.9 respectively.

antenna_IMP=$Z_S$=0.416−90.3$j$ rectifier_IMP=$Z_L$=1.87−44.0$j$

Then rewriting equations 8.8 and 8.9 as described in equation 8.10 and 8.11 values are solved. Then using equations 8.17 and 8.18 the unknown variables are solved, B=±2.12 and X=±46.3. Further, since B has minimal impact, no component is needed for Z1, and Z2 is solved using the equation for a capacitor and obtains a value of 1.37 pF.

Using Agilent's Advanced Design Solutions (ADS), Table 8.4 is solved to show the impedance components needed in the L-matching network. This creates a conversion of power at a given powering frequency between an FR-4 antenna and the full system load.

TABLE 8.4

Components to L-match FR-4 antenna with rectifier connected to system load

| | \multicolumn{10}{c|}{Frequency} |
|---|---|---|---|---|---|---|---|---|---|---|
| | 2 | 2.1 | 2.2 | 2.3 | 2.4 | 2.5 | 2.6 | 2.7 | 2.8 | 2.9 | 3 |
| Z1 | — | — | — | — | — | — | — | — | — | 0.50 | — |
| Unit | — | — | — | — | — | — | — | — | — | pF | — |
| Z2 | 0.50 | 0.62 | 0.73 | 0.87 | 1.06 | 1.36 | 1.90 | 3.10 | 10 | — | 1.03 |
| Unit | pF | pF | pF | pF | pF | pF | pF | pF | pF | — | nH |

| | \multicolumn{10}{c|}{Frequency} |
|---|---|---|---|---|---|---|---|---|---|---|
| | 3.1 | 3.2 | 3.3 | 3.4 | 3.5 | 3.6 | 3.7 | 3.8 | 3.9 | 4 |
| Z1 | — | 1.09 | 0.61 | 0.75 | 1.11 | 0.85 | 0.56 | 0.78 | 0.71 | 0.61 |
| Unit | — | pF | pF | pF | pF | pF | pF | pF | pF | pF |
| Z2 | 1.68 | 1.84 | 2.08 | 2.08 | 1.75 | 1.82 | 2.14 | 1.72 | 1.67 | 1.77 |
| Unit | nH | nH | nH | nH | nH | nH | nH | nH | nH | nH |

The invention claimed is:

1. A system for monitoring fluid pressure within an eye, the system comprising:
   a substrate;
   a pressure sensor coupled with the substrate;
   an integrated circuit coupled with the substrate and electrically coupled with the pressure sensor;
   an antenna coupled with the substrate and electrically coupled with the integrated circuit, the antenna and integrated circuit adapted to receive a first wireless signal for powering the system and transmit a second wireless signal, the second wireless signal providing an indication of the fluid pressure; and
   an LED coupled with the substrate and electrically coupled with the integrated circuit, wherein a maximum width of the LED is not greater than the maximum width of the substrate, wherein the light intensity of the LED output provides an indication of power being received by the system from a wireless external power source.

2. The system of claim 1, wherein the antenna transmits the second signal at a harmonic of the frequency of the first signal.

3. The system of claim 1, wherein the harmonic is the third harmonic of the first signal.

4. The system of claim 1, wherein the substrate defines a maximum width of no greater than about 0.7 millimeters;
   wherein a maximum width of the pressure sensor is no greater than the maximum width of the substrate; and
   wherein a maximum width of the integrated circuit is no greater than the maximum width of the substrate.

5. The system of claim 1 wherein the pressure sensor is placed in a non-human.

6. The system of claim 5, wherein the pressure sensor is implanted in the eye of the non-human.

7. The system of claim 1, wherein the substrate is polymeric.

8. The system of claim 1, wherein the sensitivity is substantially constant over a range of from about 0 mmHg to about 50 mmHg above atmospheric pressure.

9. The system of claim 8, wherein the pressure sensor has a sensitivity of no less than about 0.3 fF/mmHg.

10. The system of claim 1, wherein the substrate is flexible so as to be able to conform to a curved surface.

11. The system of claim 10, wherein the pressure sensor has a flat orientation and a curved orientation, and in which the pressure sensor has a sensitivity of no less than about 0.3 fF/mmHg whether the substrate is in a flat orientation or a curved orientation.

12. The system of claim 11, wherein the sensitivity is substantially constant over a range of from about 0 mmHg to about 50 mmHg above atmospheric pressure.

13. The system of claim 1, wherein the membrane has a depth of no greater than about 7 microns when the membrane is in an uncompressed position.

14. The system of claim 1, wherein a perimeter of the substrate defines an area of no greater than about 2 millimeters$^2$.

15. The system of claim 14, wherein the membrane has a depth of no greater than about 7 microns when the membrane is in an uncompressed position.

16. The system of claim 15, wherein the substrate defines a maximum width of no greater than about 0.7 millimeters;
   wherein a maximum width of the pressure sensor is no greater than the maximum width of the substrate; and
   wherein a maximum width of the integrated circuit is no greater than the maximum width of the substrate.

17. The system of claim 16, wherein the substrate is polymeric.

* * * * *